(12) United States Patent
Blackburn et al.

(10) Patent No.: US 6,391,299 B1
(45) Date of Patent: May 21, 2002

(54) ANTI-FACTOR IX/IXA ANTIBODIES

(75) Inventors: Michael Neal Blackburn, Phoenixville, PA (US); William Robert Church, Burlington, VT (US); Giora Zeev Feuerstein, Wynnewood, PA (US); Mitchell Stuart Gross, Wayne, PA (US); Andrew John Nichols, Chester Springs, PA (US); Eduardo Agustin Padlan, Kensington, MD (US); Arunbhai Haribhai Patel; Daniel Robert Sylvester, both of Phoenixville, PA (US)

(73) Assignees: SmithKline Beecham Corporation, Philadelphia, PA (US); University of Vermont and State Agricultural College, Burlington, VT (US)

( * ) Notice: Subject to any disclaimer, the term of this patent is extended or adjusted under 35 U.S.C. 154(b) by 0 days.

(21) Appl. No.: 09/344,050

(22) Filed: Jun. 25, 1999

Related U.S. Application Data

(62) Division of application No. 08/783,853, filed on Jan. 16, 1997, now Pat. No. 6,005,091.
(60) Provisional application No. 60/010,108, filed on Jan. 17, 1996, and provisional application No. 60/029,119, filed on Oct. 24, 1996, now abandoned.

(51) Int. Cl.⁷ ...................... A61K 39/395; C12P 21/08; C07K 16/00

(52) U.S. Cl. ............... 424/133.1; 424/158.1; 530/387.3; 530/388.25

(58) Field of Search .......................... 424/133.1, 134.1, 424/139.1, 141.1, 142.1, 145.1, 158.1; 530/387.1, 387.3, 387.9, 388.1, 388.15, 388.25

(56) References Cited

U.S. PATENT DOCUMENTS 5,387,581 A   2/1995  Odawara et al. ............ 514/165

FOREIGN PATENT DOCUMENTS

EP    0 388 914    9/1990    ........... C12P/21/08
WO    91/09967    * 7/1991

OTHER PUBLICATIONS

Sugo et al. Thrombosis Research, 58:603–614, 1990.*
F. Desposito and Y. Arkel, "Inhibitors of Coagulation in Children", *Critical Reviews in Oncology/Hematology*, vol. 7, No. 1, pp. 53–69 (1987).
Griffin et al., "The Production and Characterisation of a Panel of Ten Murine Monoclonal Antibodies to Human Procoagulant Factor VIII", *Thrombosis and Haemostasis*, vol. 55 (1), pp. 40–46 (1986).
S. Morrison, "In Vitro Antibodies: Strategies for Production and Application", *Annu. Rev. Immunol.*, vol. 10, pp. 239–65 (1992).

Warrier et al., "Safety of High Doses of a Monoclonal Antibody–Purified Factor IX Concentrate", *American Journal of Hematology*, vol. 49, pp. 92–94 (1995).
Lenting et al., "A Novel Antithrombotic Strategy Based on Inhibitors of Factor VIII–factor IX Complex Assemply", *Thrombosis and Hemostasis*, Jun. Supplement, p. 689 (1997).
Lenting et al., "The Sequence $Glu^{1811}$–$Lys^{1818}$ of Human Blood Coagulation Factor VIII Comprises a Binding Site for Activated Factor IX", *The Journal of Biological Chemistry*, vol. 271, No. 4, pp. 1935–1940 (1996).
Bajaj et al., "A Monoclonal Antibody to Factor IX That Inhibits the Factor VIII:Ca Potentiation of Factor X Activation", *J. Biol. Chem.*, vol. 260, No. 21, pp. 11574–11580 (1985).
Bajaj et al., "Antibody–Probed Conformational Transitions in the Protease Domain of Human Factor IX Upon Calcium Binding and Zymogen Activation: Putative High–Affinity $Ca^{2+}$–Binding Site in the Protease Domain", *Proc. Natl. Acad. Sci, USA*, vol. 89, pp. 152–156 (1992).
Cheung et al., "Localization of a Calcium–Dependent Eiptope to the Amino Terminal Region of the GLA Domain of Human Factor IX", *Thrombosis Research*, vol. 81, No. 1, pp. 65–73 (1996).
Church et al., "An Inhibitory Monoclonal Antibody to Factor X that Blocks Prothrombin Activation but not Prothrombinase Enzyme Assembly", *Blood*, vol. 72, No. 6 (Dec.), pp. 1911–1921 (1988).
Donath et al., "Kinetics of Factor VIII Light–Chain Cleavage by Thrombin and Factor Xa", *Eur. J. Biochem.*, vol. 240, 365–372 (1996).
Frazier et al., "Mapping of Monoclonal Antibodies to Human Factor IX", *Blood*, vol. 74, No. 3, pp. 971–977 (1989).
Fulcher et al., "Localization of Human Factor FVIII Inhibitor Epitopes to Two Polypeptide Fragments", *Proc. Natl. Acad. Sci. USA*, vol. 82, pp. 7728–7732 (1985).
Healey et al., "Residues 484–508 Contain a Major Determinant of the Inhibitory Epitope in the A2 Domain of Human Factor VIII", *J. Biol. Chem*, vol. 270, No. 24, pp. 14505–14509 (1995).
Hoffman et al., "Factors IXa and Xa Play Distinct Roles in Tissue Factor–Dependent Initiation of Coagulation", *Blood*, vol. 86, No. 5, pp. 1794–1801 (1995).
L. Hoyer and D. Scandella, "Factor VIII Inhibitors: Structure and Function in Autoantibody and Hemophilia A Patients", *Seminars in Hematology*, vol. 31, No. 2, Suppl. 4, pp. 1–5 (1994).
Jenny et al., "Immunochemical Techniques for Studying Coagulation Proteins", *Methods in Enzymology*, vol. 222, pp. 400–416 (1993).

(List continued on next page.)

*Primary Examiner*—Patricia A. Duffy
(74) *Attorney, Agent, or Firm*—Kirk Baumeister; William T. King

(57) ABSTRACT

Monoclonal antibodies directed against coagulation factors and their use in inhibiting thrombosis are disclosed.

13 Claims, 9 Drawing Sheets

OTHER PUBLICATIONS

Larson et al., "Structural Integrity of the γ–Carboxyglutamic Acid Domain of Human Blood Coagulation Factor IXa is Required for Its Binding to Cofactor VIIIa", *J. Biol. Chem.*, vol. 271, No. 7, pp. 3869–3876 (1996).

Leyte et al., "Inhibition of Human Coagulation Factor VIII by Monoclonal Antibodies", *J. Biochem.*, vol. 263, pp. 187–194 (1989).

Lollar et al., "Inhibition of Human Factor Villa by Anti–A2 Subunit Antibodies", *J. Clin. Invest.*, vol. 93, pp. 2497–2504 (1994).

J. Loscalzo and A. Schafer, "Factor VIII and Other Coagulation Factor Inhibitors", *Thrombosis and Hemorrhage*, Chapter 37, pp. 729–747 (1994).

Lubin et al., "Elimination of a Major Inhibitor Epitope in Factor VIII", *J. Biol. Chem.*, vol. 269, No. 12, pp. 8639–8641 (1994).

Ouelette et al., "Neutralization of Factor X Activity by Factor X–Specific Monoclonal Antibodies", *Blood Coagulation and Fibrinolysis*, vol. 3, pp. 563–574 (1992).

Saenko et al., "Slowed Release of Thrombin–Cleaved Factor VIII from von Willebrand Factor by a Monoclonal and a Human Antibody Is a Novel Mechanism for Factor VIII Inhibition", *J. Biol. Chem.*, vol. 271, No. 44, pp. 27424–27431 (1996).

D. Scandella, "Human Antibodies Which Inactivate Factor VIII: Their Epitope Specificity and Biochemical and Functional Characteristics", *International Journal of Pediatric Hematology/Oncology*, vol. 1, pp. 437–447 (1994).

D. Scandella, "Human Anti–Factor VIII Antibodies: Epitope Localization and Inhibitory Function", *Vox Sanguinis*, vol. 70 (suppl 1), pp. 9–14 (1996).

Sinha et al., "Functional Characterization of Human Blood Coagluation Factor XIa using Hybridoma Antibodies", *J. of Biol. Chem.*, vol. 260, No. 19, pp. 10714–10719 (1985).

Söhngen et al., "Acquired Factor VIII Inhibitors in Nonhemophilic Patients", *Ann Hematol*, vol. 74, pp. 89–93 (1997).

Sugahara et al., "Isolation and Characterization of Canine Factor IX", *Thrombosis and Haemostasis*, vol. 75(3), pp. 450–455 (1996).

Tiarks et al., "Factor VIII Epitopes Recognized with Inhibitory Monoclonal Antibodies", *Acta Haematol*, vol. 83, pp. 69–73 (1990).

Abstracts, "Thrombosis and Haemostasis", *J. International Society on Thrombosis and Haemostasis*, vol. 69(6), p. 1239, Abstract 2485 (1993).

Bessos et al., "The Characterization of a Panel of Monoclonal Antibodies to Human Coagulation Factor IX", *Thrombosis Research*, vol. 40, pp. 863–867 (1985).

Biemond et al., "Complete Inhibition of Endotoxin–Induced Coagulation Activation in Chimpanezees with a Monoclonal Fab Fragment against Factor VII/VIIa", *Thrombosis and Haemostasis*, vol. 73, No. 1, pp. 223–230 (1995).

Lenting et al., "Identification of a Binding Site for Blood Coagulation Factor IXa on the Light Chain of Human Factor VIII", *The Journal of Biological Chemistry*, vol. 269, No. 10, pp. 7150–7155 (1994).

L. Stryer, *Biochemistry*, W.H. Freeman and Company, San Franciso, 1981, pp. 512–513.

Kasai et al., "Molecular Cloning of Murine Monoclonal Anti–idiotypic Fab", *Journal of Immunological Methods*, vol. 155, pp. 77–89 (1992).

Fang et al., "Human Rheumatoid Factors with Restrictive Specificty for Rabbit Immunoglobulin G: Auto– and Multi–reactivity, Diverse . . . V IIIb", *J. Exp. Med.*, vol. 179, pp. 1445–1456 (1994).

Silberstein et al., "Relationship of Variable Region Genes Expressed by a Human B Cell . . . Autoantibodies", *J. Exp. Med.*, vol. 169, pp. 1631–1643, (1989).

Pascual, et al., "The Complete Nucleotide Sequences of the Heavy Chain Regions . . . Rheumatoid Arthritis", *J. Clin. Invest.*, vol. 86, pp. 1320–1328 (1990).

Roark, et al., "Breakdown of B Cell Tolerance in a Mouse Model of Systemic Lupus Erythematosus", *J. Exp. Med.*, vol. 181, pp. 1157–1167 (1995).

S. Stark and A. Caton, "Antibodies that Are Specific for a Single Amino Acid Interchange in a Protein Epitope Use Structurally Distinct Variable Regions", *J. Exp. Med.*, vol. 174, pp. 613–624 (1991).

\* cited by examiner

ANTI-FACTOR IX/IXA ANTIBODIES

This application is a divisional of application Ser. No. 08/783,853, filed Jan. 16, 1997, now U.S. Pat. No. 6,005, 091, which claims the benefit of U.S. Provisional application Serial No. 60/010,108, filed Jan. 17, 1996, now abandoned, and U.S. Provisional application Serial No. 60/029,119, filed Oct. 24, 1996, now abandoned.

FIELD OF THE INVENTION

This invention relates to monoclonal antibodies (mAbs) that bind to a human coagulation factor or cofactor and their use as self-limiting inhibitors of thrombosis.

BACKGROUND OF THE INVENTION

Under normal circumstances, an injury, be it minor or major, to vascular endothelial cells lining a blood vessel triggers a hemostatic response through a sequence of events commonly referred to as the coagulation "cascade." The cascade culminates in the conversion of soluble fibrinogen to insoluble fibrin which, together with platelets, forms a localized clot or thrombus which prevents extravasation of blood components. Wound healing can then occur followed by clot dissolution and restoration of blood vessel integrity and flow.

The events which occur between injury and clot formation are a carefully regulated and linked series of reactions. In brief, a number of plasma coagulation proteins in inactive proenzyme forms and cofactors circulate in the blood. Active enzyme complexes are assembled at an injury site and are sequentially activated to serine proteases, with each successive serine protease catalyzing the subsequent proenzyme to protease activation. This enzymatic cascade results in each step magnifying the effect of the succeeding step. For an overview of the coagulation cascade see the first chapter of "Thombosis and Hemorrhage", J. Loscalzo and A. Schafer, eds., Blackwell Scientific Publications, Oxford, England (1994).

While efficient clotting limits the loss of blood at an injury site, inappropriate formation of thrombi in veins or arteries is a common cause of disability and death. Abnormal clotting activity can result in and/or from pathologies or treatments such as myocardial infarction, unstable angina, atrial fibrillation, stroke, renal damage, percutaneous translumenal coronary angioplasty, disseminated intravascular coagulation, sepsis, pulmonary embolism and deep vein thrombosis. The formation of clots on foreign surfaces of artificial organs, shunts and prostheses such as artificial heart valves is also problematic.

Approved anticoagulant agents currently used in treatment of these pathologies and other thrombotic and embolic disorders include the sulfated heteropolysaccharides heparin and low molecular weight (LMW) heparin. These agents are administered parenterally and can cause rapid and complete inhibition of clotting by activation of the thrombin inhibitor, antithrombin III and inactivation of all of the clotting factors.

However, due to their potency, heparin and LMW heparin suffer drawbacks. Uncontrolled bleeding as a result of the simple stresses of motion and accompanying contacts with physical objects or at surgical sites is the major complication and is observed in 1 to 7% of patients receiving continuous infusion and in 8 to 14% of patients given intermittent bolus doses. To minimize this risk, samples are continuously drawn to enable ex vivo clotting times to be continuously monitored, which contributes substantially to the cost of therapy and the patient's inconvenience.

Further, the therapeutic target range to achieve the desired level of efficacy without placing the patient at risk for bleeding is narrow. The therapeutic range is approximately 1 to less than 3 ug heparin/ml plasma which results in activated partial thromboplastin time (aPTT) assay times of about 35 to about 100 seconds. Increasing the heparin concentration to 3 ug/ml exceeds the target range and at concentrations greater than 4 ug/ml, clotting activity is not detectable. Thus, great care must be taken to keep the patient's plasma concentrations within the therapeutic range.

Another approved anticoagulant with slower and longer lasting effect is warfarin, a coumarin derivative. Warfarin acts by competing with Vitamin K dependent post-translational modification of prothrombin and other Vitamin K-dependent clotting factors.

The general pattern of anticoagulant action, in which blood is rendered non-clottable at concentrations only slightly higher than the therapeutic range is seen for warfarin as well as for heparin and LMW heparin. Clearly, a need exists for an anticoagulant agent which is efficacious in controlling thrombotic and embolic disorders yet does not cause uncontrolled bleeding or its possibility.

SUMMARY OF THE INVENTION

Accordingly, one aspect of the present invention is a method for inhibiting thrombosis in an animal comprising administering an effective dose of an anti-coagulation factor monoclonal antibody having self-limiting neutralizing activity.

Another aspect of the invention is an anti-coagulation factor monoclonal antibody having self-limiting neutralizing activy against the coagulation factor.

Another aspect of the invention is a monoclonal antibody having the identifying characteristics of SB 249413, SB 249415, SB 249416, SB 249417, SB 257731, SB 257732, 9E4(2)F4 or 11G4(1)B9.

Another aspect of the invention is a hybridoma cell line having the identifying characteristics of 9E4(2)F4 or 11G4 (1)B9.

Another aspect of the invention is a neutralizing Fab fragment or F(ab')$_2$ fragment thereof, produced by deleting the Fc region of the monoclonal antibodies of the invention.

Another aspect of the invention is a neutralizing Fab fragment or F(ab')$_2$ fragment thereof, produced by chain shuffling whereby the Fd heavy chain of the monoclonal antibodies of the invention is expressed in a murine light chain filamentous phage Fab display library.

Another aspect of the invention is a neutralizing Fab fragment or F(ab')$_2$ fragment thereof, produced by chain shuffling whereby the light chain of the monoclonal antibodies of the invention is expressed in a murine heavy chain filamentous phage Fab display library.

Another aspect of the invention is an immunoglobulin heavy chain complementarity determining region having an amino acid sequence selected from the group consisting of SEQ ID NOs: 8, 9 and 10.

Another aspect of the invention is an immunoglobulin light chain complementarity determining region having an amino acid sequence selected from the group consisting of SEQ ID NOs: 12, 13 and 14.

Another aspect of the invention is an altered antibody comprising a heavy chain and a light chain, wherein the framework regions of said heavy and light chains are derived from at least one selected antibody and the amino acid sequences of the complementarity determining regions of each said chain are derived from an anti-coagulation factor monoclonal antibody having self-limiting neutralizing activity against the coagulation factor.

Another aspect of the invention is a chimeric antibody comprising a heavy chain and a light chain, said antibody characterized by inhibiting the function of intrinsic or common pathway coagulation factors in a self-limiting manner, wherein thrombosis is inhibited and limited modulation of coagulation is produced, wherein the constant regions of said heavy and light chains are derived from at least one selected antibody and the amino acid sequences of the variable regions of each said chain are derived from an anti-coagulation factor monoclonal antibody having self-limiting neutralizing activity against the coagulation factor.

Yet another aspect of the invention is a pharmaceutical composition comprising the humanized antibodies or chimeric antibody of the invention and a pharmaceutically acceptable carrier.

DETAILED DESCRIPTION OF THE INVENTION

Figure 1:
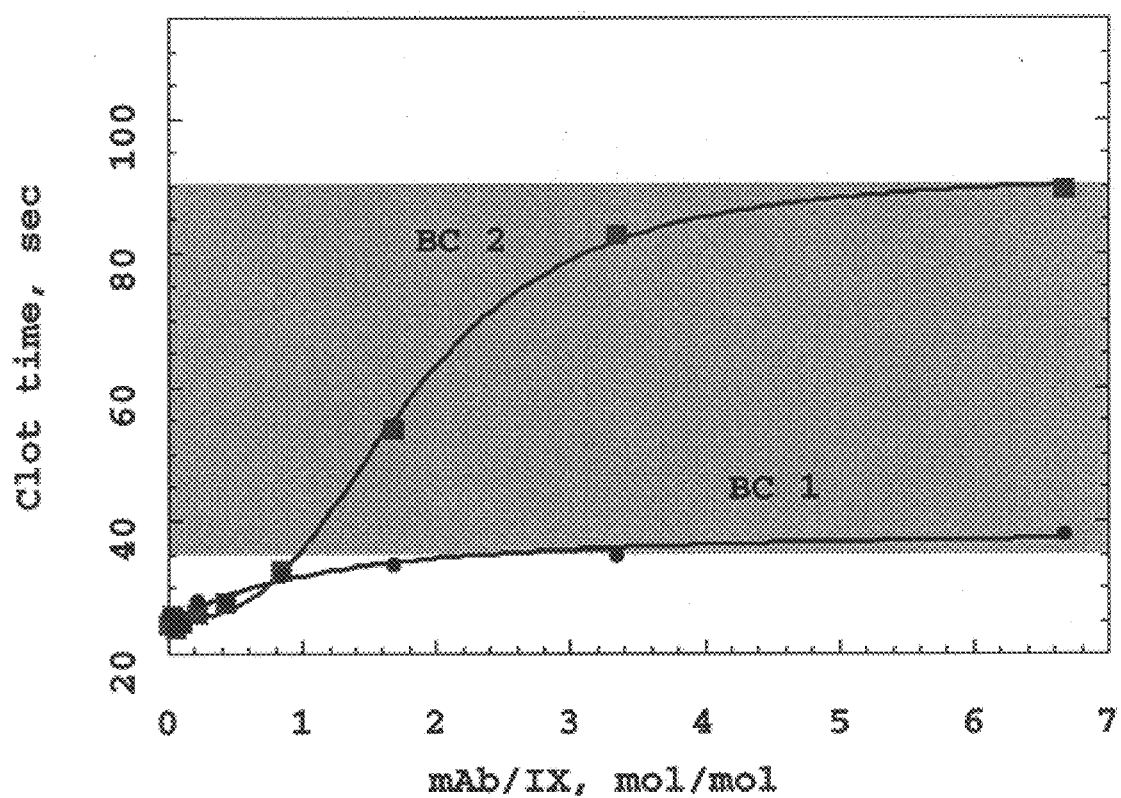
FIG. 1 is a graph of experimental results demonstrating the titration of normal human plasma with the murine anti-Factor IX mAbs BC1 and BC2.

The present invention provides a variety of antibodies, altered antibodies and fragments thereof directed against coagulation factors, which are characterized by self-limiting neutralizing activity. Preferably, the coagulation factor is from the intrinsic or common coagulation pathway. Most preferably, the anti-coagulation factor antibodies are anti-Factor IX, anti-Factor IXa, anti-Factor X, anti-Factor Xa, anti-Factor XI, anti-Factor XIa, anti-Factor VIII, anti-Factor VIIIa, anti-Factor V, anti-Factor Va, anti-Factor VII, anti-Factor VIIa or anti-thrombin. Particularly preferred are anti-Factor IX antibodies. Exemplary anti-coagulation factor antibodies are the humanized monoclonal antibodies SB 249413, SB 249415, SB 249416, SB 249417, SB 257731 and SB 257732 directed against human Factor IX, the chimeric monoclonal antibody chαFIX directed against human Factor IX, the murine monoclonal antibodies BC1, BC2, 9E4(2)F4 and 11G4(1)B9 which are directed against human Factor IX and/or Factor IXa or the murine monoclonal antibodies HFXLC and HFXI which are directed against human Factors X and XI, respectively. Particularly preferred is the anti-human Factor IX monoclonal antibody SB 249417.

The antibodies of the present invention can be prepared by conventional hybridoma techniques, phage display combinatorial libraries, immunoglobulin chain shuffling and humanization techniques to generate novel self-limiting neutralizing antibodies. Also included are fully human mAbs having self-limiting neutralizing activity. These products are useful in therapeutic and pharmaceutical compositions for thrombotic and embolic disorders associated with myocardial infarction, unstable angina, atrial fibrillation, stroke, renal damage, pulmonary embolism, deep vein thrombosis, percutaneous translumenal coronary angioplasty, disseminated intravascular coagulation, sepsis, artificial organs, shunts or prostheses.

As used herein, the term "self-limiting neutralizing activity" refers to the activity of an antibody that binds to a human coagulation factor, preferably from the intrinsic and common pathways, including Factor IX/IXa, X/Xa, XI/XIa, VIII/VIIIa and V/Va, VII/VIIa and thrombin and inhibits thrombosis in a manner such that limited modulation of coagulation is produced. "Limited modulation of coagulation" is defined as an increase in clotting time, as measured by prolongation of the activated partial thromboplastin time (aPTT), where plasma remains clottable with aPTT reaching a maximal value despite increasing concentrations of monoclonal antibody. This limited modulation of coagulation is in contrast to plasma being rendered unclottable and exhibiting an infinite aPTT in the presence of increasing concentrations of heparin. Preferably, the maximal aPTT value of the methods of the invention are within the heparin therapeutic range. Most preferably, maximal aPTT is within the range of about 35 seconds to about 100 seconds which corresponds to about 1.5 times to about 3.5 times the normal control aPTT value. In one embodiment of the invention, aPTT is prolonged without significant prolongation of prothrombin time (PT).

"Altered antibody" refers to a protein encoded by an altered immunoglobulin coding region, which may be obtained by expression in a selected host cell. Such altered antibodies are engineered antibodies (e.g., chimeric or humanized antibodies) or antibody fragments lacking all or part of an immunoglobulin constant region, e.g., Fv, Fab, Fab' or F(ab')$_2$ and the like.

"Altered immunoglobulin coding region" refers to a nucleic acid sequence encoding an altered antibody of the invention. When the altered antibody is a CDR-grafted or humanized antibody, the sequences that encode the complementarity determining regions (CDRs) from a non-human immunoglobulin are inserted into a first immunoglobulin partner comprising human variable framework sequences. Optionally, the first immunoglobulin partner is operatively linked to a second immunoglobulin partner.

"First immunoglobulin partner" refers to a nucleic acid sequence encoding a human framework or human immunoglobulin variable region in which the native (or naturally-occurring) CDR-encoding regions are replaced by the CDR-encoding regions of a donor antibody. The human variable region can be an immunoglobulin heavy chain, a light chain (or both chains), an analog or functional fragments thereof. Such CDR regions, located within the variable region of antibodies (immunoglobulins) can be determined by known methods in the art. For example Kabat et al. in "Sequences of Proteins of Immunological Interest", 4th Ed., U.S. Department of Health and Human Services, National Institutes of Health (1987) disclose rules for locating CDRs. In addition, computer programs are known which re useful for identifying CDR regions/structures.

"Second immunoglobulin partner" refers to another nucleotide sequence encoding a protein or peptide to which the first immunoglobulin partner is fused in frame or by means of an optional conventional linker sequence (i.e., operatively linked). Preferably, it is an immunoglobulin gene. The second immunoglobulin partner may include a nucleic acid sequence encoding the entire constant region for the same (i.e., homologous, where the first and second altered antibodies are derived from the same source) or an additional (i.e., heterologous) antibody of interest. It may be an immunoglobulin heavy chain or light chain (or both chains as part of a single polypeptide). The second immunoglobulin partner is not limited to a particular immunoglobulin class or isotype. In addition, the second immunoglobulin partner may comprise part of an immunoglobulin constant region, such as found in a Fab, or $F(ab)_2$ (i.e., a discrete part of an appropriate human constant region or framework region). Such second immunoglobulin partner may also comprise a sequence encoding an integral membrane protein exposed on the outer surface of a host cell, e.g., as part of a phage display library, or a sequence encoding a protein for analytical or diagnostic detection, e.g., horseradish peroxidase, β-galactosidase, etc.

The terms Fv, Fc, Fd, Fab, Fab' or $F(ab')_2$ are used with their standard meanings. See, e.g., Harlow et al. in "Antibodies A Laboratory Manual", Cold Spring Harbor Laboratory, (1988).

As used herein, an "engineered antibody" describes a type of altered antibody, i.e., a full-length synthetic antibody (e.g., a chimeric or humanized antibody as opposed to an antibody fragment) in which a portion of the light and/or heavy chain variable domains of a selected acceptor antibody are replaced by analogous parts from one or more donor antibodies which have specificity for the selected epitope. For example, such molecules may include antibodies characterized by a humanized heavy chain associated with an unmodified light chain (or chimeric light chain), or vice versa. Engineered antibodies may also be characterized by alteration of the nucleic acid sequences encoding the acceptor antibody light and/or heavy variable domain framework regions in order to retain donor antibody binding specificity. These antibodies can comprise replacement of one or more CDRs (preferably all) from the acceptor antibody with CDRs from a donor antibody described herein.

A "chimeric antibody" refers to a type of engineered antibody which contains a naturally-occurring variable region (light chain and heavy chains) derived from a donor antibody in association with light and heavy chain constant regions derived from an acceptor antibody.

A "humanized antibody" refers to a type of engineered antibody having its CDRs derived from a non-human donor immunoglobulin, the remaining immunoglobulin-derived parts of the molecule being derived from one or more human immunoglobulins. In addition, framework support residues may be altered to preserve binding affinity. See, e.g., Queen et al., *Proc. Natl Acad Sci USA*, 86, 10029–10032 (1989), Hodgson et al., *Bio/Technology*, 9, 421 (1991).

The term "donor antibody" refers to a monoclonal or recombinant antibody which contributes the nucleic acid sequences of its variable regions, CDRs or other functional fragments or analogs thereof to a first immunoglobulin partner, so as to provide the altered immunoglobulin coding region and resulting expressed altered antibody with the antigenic specificity and neutralizing activity characteristic of the donor antibody. One donor antibody suitable for use in this invention is a murine self-limiting neutralizing monoclonal antibody designated as BC2. Other suitable donor antibodies include the murine self-limiting neutralizing monoclonal antibodies designated as BC1, 9E4(2)F4, 11G4(1)B9, HFXLC and HFXI.

The term "acceptor antibody" refers to monoclonal or recombinant antibodies heterologous to the donor antibody, which contributes all, or a portion, of the nucleic acid sequences encoding its heavy and/or light chain framework regions and/or its heavy and/or light chain constant regions to the first immunoglobulin partner. Preferably, a human antibody is the acceptor antibody.

"CDRs" are defined as the complementarity determining region amino acid sequences of an antibody which are the hypervariable regions of immunoglobulin heavy and light chains. See, e.g., Kabat et al., *Sequences of Proteins of Immunological Interest,* 4th Ed., U.S. Department of Health and Human Services, National Institutes of Health (1987). There are three heavy chain and three light chain CDRs or CDR regions in the variable portion of an immunoglobulin. Thus, "CDRs" as used herein refers to all three heavy chain CDRs, or all three light chain CDRs or both all heavy and all light chain CDRs, if appropriate.

CDRs provide the majority of contact residues for the binding of the antibody to the antigen or epitope. CDRs of interest in this invention are derived from donor antibody variable heavy and light chain sequences, and include analogs of the naturally occurring CDRs, which analogs also share or retain the same antigen binding specificity and/or neutralizing ability as the donor antibody from which they were derived.

By "sharing the antigen binding specificity or neutralizing ability" is meant, for example, that although mAb BC2 may be characterized by a certain level of self-limiting neutralizing activity, a CDR encoded by a nucleic acid sequence of BC2 in an appropriate structural environment may have a lower, or higher activity. It is expected that CDRs of BC2 in such environments will nevertheless recognize the same epitope(s) as BC2.

A "functional fragment" is a partial heavy or light chain variable sequence (e.g., minor deletions at the amino or carboxy terminus of the immunoglobulin variable region) which retains the same antigen binding specificity and/or neutralizing ability as the antibody from which the fragment was derived.

An "analog" is an amino acid sequence modified by at least one amino acid, wherein said modification can be chemical or a substitution or a rearrangement of a few amino acids (i.e., no more than 10), which modification permits the amino acid sequence to retain the biological characteristics, e.g., antigen specificity and high affinity, of the unmodified sequence. Exemplary analogs include silent mutations which can be constructed, via substitutions, to create certain endonuclease restriction sites within or surrounding CDR-encoding regions.

Analogs may also arise as allelic variations. An "allelic variation or modification" is an alteration in the nucleic acid sequence encoding the amino acid or peptide sequences of the invention. Such variations or modifications may be due to degeneracy in the genetic code or may be deliberately engineered to provide desired characteristics. These variations or modifications may or may not result in alterations in any encoded amino acid sequence.

The term "effector agents" refers to non-protein carrier molecules to which the altered antibodies, and/or natural or synthetic light or heavy chains of the donor antibody or other fragments of the donor antibody may be associated by conventional means. Such non-protein carriers can include conventional carriers used in the diagnostic field, e.g., polystyrene or other plastic beads, polysaccharides, e.g., as used in the BIAcore (Pharmacia) system, or other non-protein substances useful in the medical field and safe for administration to humans and animals. Other effector agents may include a macrocycle, for chelating a heavy metal atom or radioisotopes. Such effector agents may also be useful to increase the half-life of the altered antibodies, e.g., polyethylene glycol.

For use in constructing the antibodies, altered antibodies and fragments of this invention, a non-human species such as bovine, ovine, monkey, chicken, rodent (e.g., murine and rat) may be employed to generate a desirable immunoglobulin upon presentment with a human coagulation factor, preferably factor IX/IXa, X/Xa, XI/XIa, VIII/VIIIa, V/Va, VII/VIIa or thrombin or a peptide epitope therefrom. Conventional hybridoma techniques are employed to provide a hybridoma cell line secreting a non-human mAb to the respective coagulation factor. Such hybridomas are then screened for binding using Factor IX/IXa, X/Xa, XI/XIa, VIII/VIIIa, V/Va, VII/VIIa or thrombin coated to 96-well plates, as described in the Examples section, or alternatively with biotinylated Factor IX/IXa, X/Xa, XI/XIa, VIII/VIIIa, V/Va, VII/VIIa or thrombin bound to a streptavidin-coated plate. Alternatively, fully human mAbs can be generated by techniques known to those skilled in the art and used in this invention.

One exemplary, self-limiting neutralizing mAb of this invention is mAb BC2, a murine antibody which can be used for the development of a chimeric or humanized molecule. The BC2 mAb is characterized by a self-limiting inhibitory activity on clotting time. As measured by the aPTT assay, the effect of the BC2 mAb on clot time exhibits a maximal value of about 100 seconds. The BC2 mAb also binds Factor IXa, inhibits Factor IX to IXa conversion and inhibits Factor IXa activity. Divalent metal cofactors are required for activity, with the mAb exhibiting a greater preference for $Ca^{2+}$ over $Mn^{2+}$. The observed $IC_{50}$ in the aPTT assay is approximately 50 nM. The BC2 mAb exhibits a species cross-reactivity with rat and is of isotype IgG2a.

Other desirable donor antibodies are the murine mAbs, $BC_1$, 9E4(2)F4 and 11G4(1)B9. These mAbs are characterized by a self-limiting inhibitory activity on clotting time. As measured by the aPTT assay, the effect of these mAbs on clot time exhibits a maximal value of about 90 to 100 seconds for 9E4(2)F4 and about 80 seconds for 11G4(1)B9. The BC1 mAb also binds Factor IXa, inhibits Factor IXa activity but does not inhibit Factor IX to IXa conversion. A metal cofactor is not required for its activity. The observed $IC_{50}$ for BC1 in the aPTT assay is approximately 35 nM. The BC1 mAb is of isotype IgG1.

Yet another desirable donor antibody characterized by a self-limiting inhibitory activity on clotting time is the murine mAb HFXLC. As measured by the aPTT assay, the effect of the HFXLC mAb on clot time exhibits a maximal value of about 50 to 60 seconds. The HFXLC mAb binds Factor X light chain, and inhibits Factor X/Xa activity. The observed $IC_{50}$ in the aPTT assay is approximately 20 nM.

Yet another desirable donor antibody characterized by a self-limiting inhibitory activity on clotting time is the murine mAb, HFXI. As measured by the aPTT assay, the effect of the HFXI mAb on clot time exhibits a maximal value of about 100 seconds. The HFXLC mAb binds Factor XI and inhibits Factor XI/XIa activity. The observed $IC_{50}$ in the aPTT assay is approximately 30 nM.

While not intending to be bound to any particular theory regarding the mechanism of action, these mAbs appear to regulate coagulation by a non-competitive or allosteric mechanism whereby only partial inhibition is achieved.

This invention is not limited to the use of the BC1, BC2, 9E4(2)F4, 11G4(1)B9, HFXLC, HFXI or their hypervariable (i.e., CDR) sequences. Any other appropriate high-affinity antibodies characterized by a self-limiting neutralizing activity and corresponding CDRs may be substituted therefor. Identification of the donor antibody in the following description as BC1, BC2, 9E4(2)F4, 11G4(1)B9, HFXLC or HFXI is made for illustration and simplicity of description only.

The present invention also includes the use of Fab fragments or F(ab')$_2$ fragments derived from mAbs directed against the appropriate human coagulation factor or cofactor. These fragments are useful as agents having self-limiting neutralizing activity against coagulation factors, preferably against Factor IX/IXa, X/Xa, Xi/XIa, VIII/VIIIa, V/Va, VII/VIIa or thrombin. A Fab fragment contains the entire light chain and amino terminal portion of the heavy chain. An F(ab')2 fragment is the fragment formed by two Fab fragments bound by disulfide bonds. The mAbs BC1, BC2, 9E4(2)F4, 11G4(1)B9, HFXLC and HFXI and other similar high affinity antibodies, provide sources of Fab fragments and F(ab')$_2$ fragments which can be obtained by conventional means, e.g., cleavage of the mAb with the appropriate proteolytic enzymes, papain and/or pepsin, or by recombinant methods. These Fab and F(ab')$_2$ fragments are useful themselves as therapeutic, prophylactic or diagnostic agents, and as donors of sequences including the variable regions and CDR sequences useful in the formation of recombinant or humanized antibodies as described herein.

The Fab and F(ab')$_2$ fragments can be constructed via a combinatorial phage library (see, e.g., Winter et al., *Ann. Rev. Immunol.*, 12:433–455 (1994)) or via immunoglobulin chain shuffling (see, e.g., Marks et al., *Bio/Technology*, 10:779–783 (1992), which are both hereby incorporated by reference in their entirety, wherein the Fd or $v_H$ immunoglobulin from a selected antibody (e.g., BC2) is allowed to associate with a repertoire of light chain immunoglobulins, $v_L$ (or $v_K$), to form novel Fabs. Conversely, the light chain immunoglobulin from a selected antibody may be allowed to associate with a repertoire of heavy chain immunoglobulins, $v_H$ (or Fd), to form novel Fabs. Self-limiting neutralizing Factor IX Fabs can be obtained by allowing the Fd of mAb BC2 to associate with a repertoire of light chain immunoglobulins. Hence, one is able to recover neutralizing Fabs with unique sequences (nucleotide and amino acid) from the chain shuffling technique.

The mAb BC2 or other antibodies described above may contribute sequences, such as variable heavy and/or light chain peptide sequences, framework sequences, CDR sequences, functional fragments, and analogs thereof, and the nucleic acid sequences encoding them, useful in designing and obtaining various altered antibodies which are characterized by the antigen binding specificity of the donor antibody.

The nucleic acid sequences of this invention, or fragments thereof, encoding the variable light chain and heavy chain peptide sequences are also useful for mutagenic introduction of specific changes within the nucleic acid sequences encoding the CDRs or framework regions, and for incorporation of the resulting modified or fusion nucleic acid sequence into a plasmid for expression. For example, silent substitutions in the nucleotide sequence of the framework and CDR-encoding regions can be used to create restriction enzyme sites which facilitate insertion of mutagenized CDR and/or framework regions. These CDR-encoding regions can be used in the construction of the humanized antibodies of the invention.

The nucleic and amino acid sequences of the BC2 heavy chain variable region are listed in SEQ ID NOs: 5 and 7. The CDR sequences from this region are listed in SEQ ID NOs: 8, 9 and 10.

The nucleic and amino acid sequences of the BC2 light chain variable region are listed in SEQ ID NOs: 6 and 11. The CDR sequences from this region are listed in ID NOs: 12, 13 and 14.

Taking into account the degeneracy of the genetic code, various coding sequences may be constructed which encode the variable heavy and light chain amino acid sequences and CDR sequences of the invention as well as functional fragments and analogs thereof which share the antigen specificity of the donor antibody. The isolated nucleic acid sequences of this invention, or fragments thereof, encoding the variable chain peptide sequences or CDRs can be used to produce altered antibodies, e.g., chimeric or humanized antibodies or other engineered antibodies of this invention when operatively combined with a second immunoglobulin partner.

It should be noted that in addition to isolated nucleic acid sequences encoding portions of the altered antibody and antibodies described herein, other such nucleic acid sequences are encompassed by the present invention, such as those complementary to the native CDR-encoding sequences or complementary to the modified human framework regions surrounding the CDR-encoding regions. Useful DNA sequences include those sequences which hybridize under stringent hybridization conditions to the DNA sequences. See, T. Maniatis et al., *Molecular Cloning (A Laboratory Manual)*, Cold Spring Harbor Laboratory (1982), pp. 387–389. An example of one such stringent hybridization condition is hybridization at 4×SSC at 65° C., followed by a washing in 0.1×SSC at 65° C. for one hour. Alternatively, an exemplary stringent hybridization condition is 50% formamide, 4×SSC at 42° C. Preferably, these hybridizing DNA sequences are at least about 18 nucleotides in length, i.e., about the size of a CDR.

Altered immunoglobulin molecules can encode altered antibodies which include engineered antibodies such as chimeric antibodies and humanized antibodies. A desired altered immunoglobulin coding region contains CDR-encoding regions that encode peptides having the antigen specificity of a Factor IX/IXa, X/Xa, XI/XIa, VIII/VIIIa, V/Va, VII/VIIa or thrombin antibody, preferably a high affinity antibody such as provided by the present invention, inserted into a first immunoglobulin partner such as a human framework or human immunoglobulin variable region.

Preferably, the first immunoglobulin partner is operatively linked to a second immunoglobulin partner. The second immunoglobulin partner is defined above, and may include a sequence encoding a second antibody region of interest, for example an Fc region. Second immunoglobulin partners may also include sequences encoding another immunoglobulin to which the light or heavy chain constant region is fused in frame or by means of a linker sequence. Engineered antibodies directed against functional fragments or analogs of coagulation factors may be designed to elicit enhanced binding with the same antibody.

The second immunoglobulin partner may also be associated with effector agents as defined above, including non-protein carrier molecules, to which the second immunoglobulin partner may be operatively linked by conventional means.

Fusion or linkage between the second immunoglobulin partners, e.g., antibody sequences, and the effector agent may be by any suitable means, e.g., by conventional covalent or ionic bonds, protein fusions, or hetero-bifunctional cross-linkers, e.g., carbodiimide, glutaraldehyde and the like. Such techniques are known in the art and are described in conventional chemistry and biochemistry texts.

Additionally, conventional linker sequences which simply provide for a desired amount of space between the second immunoglobulin partner and the effector agent may also be constructed into the altered immunoglobulin coding region. The design of such linkers is well known to those of skill in the art.

In addition, signal sequences for the molecules of the invention may be modified by techniques known to those skilled in the art to enhance expression.

A preferred altered antibody contains a variable heavy and/or light chain peptide or protein sequence having the antigen specificity of mAb BC2, e.g., the $V_H$ and $V_L$ chains. Still another desirable altered antibody of this invention is characterized by the amino acid sequence containing at least one, and preferably all of the CDRs of the variable region of the heavy and/or light chains of the murine antibody molecule BC2 with the remaining sequences being derived from a human source, or a functional fragment or analog thereof.

In a further embodiment, the altered antibody of the invention may have attached to it an additional agent. For example, recombinant DNA technology may be used to produce an altered antibody of the invention in which the Fc fragment or CH2 CH3 domain of a complete antibody molecule has been replaced by an enzyme or other detectable molecule (i.e., a polypeptide effector or reporter molecule).

The second immunoglobulin partner may also be operatively linked to a non-immunoglobulin peptide, protein or fragment thereof heterologous to the CDR-containing sequence having antigen specificity to a coagulation factor, preferably to Factor IX/IXa, X/Xa, XI/XIa, VIII/VIIIa, V/Va, VII/VIIa or thrombin. The resulting protein may exhibit both antigen specificity and characteristics of the non-immunoglobulin upon expression. That fusion partner characteristic may be, e.g., a functional characteristic such as another binding or receptor domain or a therapeutic characteristic if the fusion partner is itself a therapeutic protein or additional antigenic characteristics.

Another desirable protein of this invention may comprise a complete antibody molecule, having full length heavy and light chains or any discrete fragment thereof, such as the Fab or F(ab')$_2$ fragments, a heavy chain dimer or any minimal recombinant fragments thereof such as an $F_v$ or a single-chain antibody (SCA) or any other molecule with the same specificity as the selected donor mAb, e.g., mAb BC1, BC2, 9E4(2)F4, 11G4(1)B9, HFXLC or HFXI. Such protein may be used in the form of an altered antibody or may be used in its unfused form.

Whenever the second immunoglobulin partner is derived from an antibody different from the donor antibody, e.g., any isotype or class of immunoglobulin framework or constant regions, an engineered antibody results. Engineered antibodies can comprise immunoglobulin (Ig) constant regions and variable framework regions from one source, e.g., the acceptor antibody, and one or more (preferably all) CDRs from the donor antibody, e.g., the anti-Factor IX/IXa, X/Xa, XI/XIa, VIII/VIIIa, V/Va, VII/VIIa or thrombin antibodies described herein. In addition, alterations, e.g., deletions, substitutions, or additions, of the acceptor mAb light and/or heavy variable domain framework region at the nucleic acid or amino acid levels, or the donor CDR regions may be made in order to retain donor antibody antigen binding specificity.

Such engineered antibodies are designed to employ one (or both) of the variable heavy and/or light chains of the coagulation factor mAb (optionally modified as described) or one or more of the heavy or light chain CDRs. The engineered antibodies of the invention exhibit self-limiting neutralizing activity.

Such engineered antibodies may include a humanized antibody containing the framework regions of a selected human immunoglobulin or subtype or a chimeric antibody containing the human heavy and light chain constant regions fused to the coagulation factor antibody functional fragments. A suitable human (or other animal) acceptor antibody may be one selected from a conventional database, e.g., the KABAT® database, Los Alamos database, and Swiss Protein database, by homology to the nucleotide and amino acid sequences of the donor antibody. A human antibody characterized by a homology to the framework regions of the donor antibody (on an amino acid basis) may be suitable to provide a heavy chain variable framework region for insertion of the donor CDRs. A suitable acceptor antibody capable of donating light chain variable framework regions may be selected in a similar manner. It should be noted that the acceptor antibody heavy and light chains are not required to originate from the same acceptor antibody.

Preferably, the heterologous framework and constant regions are selected from human immunoglobulin classes and isotypes, such as IgG (subtypes 1 through 4), IgM, IgA, and IgE. However, the acceptor antibody need not comprise only human immunoglobulin protein sequences. For instance, a gene may be constructed in which a DNA sequence encoding part of a human immunoglobulin chain is fused to a DNA sequence encoding a non-immunoglobulin amino acid sequence such as a polypeptide effector or reporter molecule.

A particularly preferred humanized antibody contains CDRs of BC2 inserted onto the framework regions of a selected human antibody sequence. For neutralizing humanized antibodies, one, two or preferably three CDRs from the Factor IX antibody heavy and/or light chain variable regions are inserted into the framework regions of the selected human antibody sequence, replacing the native CDRs of the latter antibody.

Preferably, in a humanized antibody, the variable domains in both human heavy and light chains have been engineered by one or more CDR replacements. It is possible to use all six CDRs, or various combinations of less than the six CDRs. Preferably all six CDRs are replaced. It is possible to replace the CDRs only in the human heavy chain, using as light chain the unmodified light chain from the human acceptor antibody. Still alternatively, a compatible light chain may be selected from another human antibody by recourse to the conventional antibody databases. The remainder of the engineered antibody may be derived from any suitable acceptor human immunoglobulin.

The engineered humanized antibody thus preferably has the structure of a natural human antibody or a fragment thereof, and possesses the combination of properties required for effective therapeutic use, e.g., treatment of thrombotic and embolic diseases in man.

Most preferably, the humanized antibodies have a heavy chain amino acid sequence as set forth in SEQ ID NO: 31, 52, or 89. Also most preferred are humanized antibodies having a light chain amino acid sequence as set forth in SEQ ID NO: 44, 57, 62, 74, 78 or 99. Particularly preferred is the humanized antibody SB 249413 where the heavy chain has the amino acid sequence as set forth in SEQ ID NO: 31 and the light chain has the amino acid sequence as set forth in SEQ ID NO: 44. Also particularly preferred is the humanized antibody SB 249415 where the heavy chain has the amino acid sequence as set forth in SEQ ID NO: 52 and the light chain has the amino acid sequence as set forth in SEQ ID NO: 57. Also particularly preferred is the humanized antibody SB 249416 where the heavy chain has the amino acid sequence as set forth in SEQ ID NO: 52 and the light chain has the amino acid sequence as set forth in SEQ ID NO: 62. Also particularly preferred is the humanized antibody SB 249417 where the heavy chain has the amino acid sequence as set forth in SEQ ID NO: 52 and the light chain has the amino acid sequence as set forth in SEQ ID NO: 74. Also particularly preferred is the humanized antibody SB 257731 where the heavy chain has the amino acid sequence as set forth in SEQ ID NO: 52 and the light chain has the amino acid sequence as set forth in SEQ ID NO: 78. Also particularly preferred is the humanized antibody SB 257732 where the heavy chain has the amino acid sequence as set forth in SEQ ID NO: 89 and the light chain has the amino acid sequence as set forth in SEQ ID NO: 99.

It will be understood by those skilled in the art that an engineered antibody may be further modified by changes in variable domain amino acids without necessarily affecting the specificity and high affinity of the donor antibody (i.e., an analog). It is anticipated that heavy and light chain amino acids may be substituted by other amino acids either in the variable domain frameworks or CDRs or both. These substitutions could be supplied by the donor antibody or consensus sequences from a particular subgroup.

In addition, the constant region may be altered to enhance or decrease selective properties of the molecules of this invention. For example, dimerization, binding to Fc receptors, or the ability to bind and activate complement (see, e.g., Angal et al., Mol. Immunol, 30, 105–108 (1993), Xu et al., J. Biol. Chem, 269, 3469–3474 (1994), Winter et al., EP 307434-B).

An altered antibody which is a chimeric antibody differs from the humanized antibodies described above by providing the entire non-human donor antibody heavy chain and light chain variable regions, including framework regions, in association with human immunoglobulin constant regions for both chains. It is anticipated that chimeric antibodies which retain additional non-human sequence relative to humanized antibodies of this invention may elicit a significant immune response in humans.

Such antibodies are useful in the prevention and treatment of thrombotic and embolic disorders, as discussed below.

Preferably, the variable light and/or heavy chain sequences and the CDRs of mAb BC2 or other suitable donor mAbs, e.g., BC1, 9E4(2)F4, 11G4(1)B9, HFXLC, HFXI, and their encoding nucleic acid sequences, are utilized in the construction of altered antibodies, preferably humanized antibodies, of this invention, by the following process. The same or similar techniques may also be employed to generate other embodiments of this invention.

A hybridoma producing a selected donor mAb, e.g., the murine antibody BC2, is conventionally cloned and the DNA of its heavy and light chain variable regions obtained by techniques known to one of skill in the art, e.g., the techniques described in Sambrook et al., "Molecular Cloning: A Laboratory Manual", 2nd edition, Cold Spring Harbor Laboratory (1989). The variable heavy and light regions of BC2 containing at least the CDR-encoding regions and those portions of the acceptor mAb light and/or heavy variable domain framework regions required in order to retain donor mAb binding specificity, as well as the remaining immunoglobulin-derived parts of the antibody chain derived from a human immunoglobulin, are obtained using polynucleotide primers and reverse transcriptase. The CDR-encoding regions are identified using a known database and by comparison to other antibodies.

A mouse/human chimeric antibody may then be prepared and assayed for binding ability. Such a chimeric antibody contains the entire non-human donor antibody $V_H$ and $V_L$ regions, in association with human Ig constant regions for both chains.

Homologous framework regions of a heavy chain variable region from a human antibody are identified using computerized databases, e.g., KABAT®, and a human antibody having homology to BC2 is selected as the acceptor antibody. The sequences of synthetic heavy chain variable regions containing the BC2 CDR-encoding regions within the human antibody frameworks are designed with optional nucleotide replacements in the framework regions to incorporate restriction sites. This designed sequence is then synthesized using long synthetic oligomers. Alternatively, the designed sequence can be synthesized by overlapping oligonucleotides, amplified by polymerase chain reaction (PCR), and corrected for errors. A suitable light chain variable framework region can be designed in a similar manner.

A humanized antibody may be derived from the chimeric antibody, or preferably, made synthetically by inserting the donor mAb CDR-encoding regions from the heavy and light chains appropriately within the selected heavy and light chain framework. Alternatively, a humanized antibody of the invention may be prepared using standard mutagenesis techniques. Thus, the resulting humanized antibody contains human framework regions and donor mAb CDR-encoding regions. There may be subsequent manipulation of framework residues. The resulting humanized antibody can be expressed in recombinant host cells, e.g., COS, CHO or myeloma cells. Other humanized antibodies may be prepared using this technique on other suitable Factor IX-specific or other coagulation factor-specific, self-limiting, neutralizing, high affinity, non-human antibodies.

A conventional expression vector or recombinant plasmid is produced by placing these coding sequences for the altered antibody in operative association with conventional regulatory control sequences capable of controlling the replication and expression in, and/or secretion from, a host cell. Regulatory sequences include promoter sequences, e.g., CMV promoter, and signal sequences, which can be derived from other known antibodies. Similarly, a second expression vector can be produced having a DNA sequence which encodes a complementary antibody light or heavy chain. Preferably, this second expression vector is identical to the first except with respect to the coding sequences and selectable markers, in order to ensure, as much as possible, that each polypeptide chain is functionally expressed. Alternatively, the heavy and light chain coding sequences for the altered antibody may reside on a single vector.

A selected host cell is co-transfected by conventional techniques with both the first and second vectors (or simply transfected by a single vector) to create the transfected host cell of the invention comprising both the recombinant or synthetic light and heavy chains. The transfected cell is then cultured by conventional techniques to produce the engineered antibody of the invention. The humanized antibody which includes the association of both the recombinant heavy chain and/or light chain is screened from culture by an appropriate assay such as ELISA or RIA. Similar conventional techniques may be employed to construct other altered antibodies and molecules of this invention.

Suitable vectors for the cloning and subcloning steps employed in the methods and construction of the compositions of this invention may be selected by one of skill in the art. For example, the pUC series of cloning vectors, such as pUC19, which is commercially available from supply houses, such as Amersham or Pharmacia, may be used. Additionally, any vector which is capable of replicating readily, has an abundance of cloning sites and selectable genes (e.g., antibiotic resistance) and is easily manipulated may be used for cloning. Thus, the selection of the cloning vector is not a limiting factor in this invention.

Similarly, the vectors employed for expression of the engineered antibodies according to this invention may be selected by one of skill in the art from any conventional vector. The vectors also contain selected regulatory sequences (such as CMV promoters) which direct the replication and expression of heterologous DNA sequences in selected host cells. These vectors contain the above-described DNA sequences which code for the engineered antibody or altered immunoglobulin coding region. In addition, the vectors may incorporate the selected immunoglobulin sequences modified by the insertion of desirable restriction sites for ready manipulation.

The expression vectors may also be characterized by genes suitable for amplifying expression of the heterologous DNA sequences, e.g., the mammalian dihydrofolate reductase gene (DHFR). Other preferable vector sequences include a poly A signal sequence, such as from bovine growth hormone (BGH) and the betaglobin promoter sequence (betaglopro). The expression vectors useful herein may be synthesized by techniques well known to those skilled in this art.

The components of such vectors, e.g., replicons, selection genes, enhancers, promoters, signal sequences and the like, may be obtained from commercial or natural sources or synthesized by known procedures for use in directing the expression and/or secretion of the product of the recombinant DNA in a selected host. Other appropriate expression vectors of which numerous types are known in the art for mammalian, bacterial, insect, yeast and fungal expression may also be selected for this purpose.

The present invention also encompasses a cell line transfected with a recombinant plasmid containing the coding sequences of the engineered antibodies or altered immunoglobulin molecules thereof. Host cells useful for the cloning and other manipulations of these cloning vectors are also conventional. However, most desirably, cells from various strains of *E. coli* are used for replication of the cloning vectors and other steps in the construction of altered antibodies of this invention.

Suitable host cells or cell lines for the expression of the engineered antibody or altered antibody of the invention are preferably mammalian cells such as CHO, COS, a fibroblast cell (e.g., 3T3) and myeloid cells, and more preferably a CHO or a myeloid cell. Human cells may be used, thus enabling the molecule to be modified with human glycosylation patterns. Alternatively, other eukaryotic cell lines may be employed. The selection of suitable mammalian host cells and methods for transformation, culture, amplification, screening and product production and purification are known in the art. See, e.g., Sambrook et al., supra.

Bacterial cells may prove useful as host cells suitable for the expression of the recombinant Fabs of the present invention (see, e.g., Plückthun, A., *Immunol. Rev.,* 130, 151–188 (1992)). However, due to the tendency of proteins expressed in bacterial cells to be in an unfolded or improperly folded form or in a non-glycosylated form, any recombinant Fab produced in a bacterial cell would have to be screened for retention of antigen binding ability. If the molecule expressed by the bacterial cell was produced in a properly folded form, that bacterial cell would be a desirable host. For example, various strains of *E. coli* used for expression are well-known as host cells in the field of biotechnology. Various strains of *B. subtilis*, Streptomyces, other bacilli and the like may also be employed.

Where desired, strains of yeast cells known to those skilled in the art are also available as host cells, as well as insect cells, e.g. Drosophila and Lepidoptera and viral expression systems. See, e.g. Miller et al., *Genetic Engineering,* 8, 277–298, Plenum Press (1986) and references cited therein.

The general methods by which the vectors of the invention may be constructed, the transfection methods required to produce the host cells of the invention, and culture methods necessary to produce the altered antibody of the invention from such host cell are all conventional techniques. Likewise, once produced, the altered antibodies of the invention may be purified from the cell culture contents according to standard procedures of the art, including ammonium sulfate precipitation, affinity columns, column chromatography, gel electrophoresis and the like. Such techniques are within the skill of the art and do not limit this invention.

Yet another method of expression of the humanized antibodies may utilize expression in a transgenic animal, such as described in U.S. Pat. No. 4,873,316. This relates to an expression system using the animal's casein promoter which when transgenically incorporated into a mammal permits the female to produce the desired recombinant protein in its milk.

Once expressed by the desired method, the engineered antibody is then examined for in vitro activity by use of an appropriate assay. Presently, conventional ELISA assay formats are employed to assess qualitative and quantitative binding of the engineered antibody to Factor IX or to other appropriate coagulation factors. Additionally, other in vitro assays may also be used to verify neutralizing efficacy prior to subsequent human clinical studies performed to evaluate the persistence of the engineered antibody in the body despite the usual clearance mechanisms.

Following the procedures described for humanized antibodies prepared from BC2, one of skill in the art may also construct humanized antibodies from other donor antibodies, variable region sequences and CDR peptides described herein. Engineered antibodies can be produced with variable region frameworks potentially recognized as "self" by recipients of the engineered antibody. Minor modifications to the variable region frameworks can be implemented to effect large increases in antigen binding without appreciable increased immunogenicity for the recipient. Such engineered antibodies may effectively treat a human for coagulation factor-mediated conditions. Such antibodies may also be useful in the diagnosis of such conditions.

This invention also relates to a method for inhibiting thrombosis in an animal, particularly a human, which comprises administering an effective dose of an anti-coagulation factor monoclonal antibody having self-limiting neutralizing activity. Preferably, the coagulation factor is from the intrinsic or common coagulation pathway. Most preferably, the anti-coagulation factor monoclonal antibody is an anti-Factor IX, anti-Factor IXa, anti-Factor X, anti-Factor Xa, anti-Factor XI, anti-Factor XIa, anti-Factor VIII, anti-Factor VIIIa, anti-Factor V, anti-Factor Va, anti-Factor VII, anti-Factor VIIa or anti-thrombin. The mAb can include one or more of the engineered antibodies or altered antibodies described herein or fragments thereof.

Alternatively, acetylsalicylic acid can be administered in combination with the anti-coagulation factor monoclonal antibody. In some cases, combination therapy lowers the therapeutically effective dose of anti-coagulation factor monoclonal antibody.

The therapeutic response induced by the use of the molecules of this invention is produced by the binding to the respective coagulation factor and the subsequent self-limiting inhibition of the coagulation cascade. Thus, the molecules of the present invention, when in preparations and formulations appropriate for therapeutic use, are highly desirable for persons susceptible to or experiencing abnormal clotting activity associated with, but not limited to, myocardial infarction, unstable angina, atrial fibrillation, stroke, renal damage, pulmonary embolism, deep vein thrombosis and artificial organ and prosthetic implants.

The altered antibodies, antibodies and fragments thereof of this invention may also be used in conjunction with other antibodies, particularly human mAbs reactive with other markers (epitopes) responsible for the condition against which the engineered antibody of the invention is directed.

The therapeutic agents of this invention are believed to be desirable for treatment of abnormal clotting conditions from about 1 day to about 3 weeks, or as needed. This represents a considerable advance over the currently used anticoagulants heparin and warfarin. The dose and duration of treatment relates to the relative duration of the molecules of the present invention in the human circulation, and can be adjusted by one of skill in the art depending upon the condition being treated and the general health of the patient.

The mode of administration of the therapeutic agent of the invention may be any suitable route which delivers the agent to the host. The altered antibodies, antibodies, engineered antibodies, and fragments thereof, and pharmaceutical compositions of the invention are particularly useful for parenteral administration, i.e., subcutaneously, intramuscularly, intravenously or intranasally.

Therapeutic agents of the invention may be prepared as pharmaceutical compositions containing an effective amount of the engineered (e.g., humanized) antibody of the invention as an active ingredient in a pharmaceutically acceptable carrier. Alternatively, the pharmaceutical compositions of the invention could also contain acetysalicylic acid. In the prophylactic agent of the invention, an aqueous suspension or solution containing the engineered antibody, preferably buffered at physiological pH, in a form ready for injection is preferred. The compositions for parenteral administration will commonly comprise a solution of the engineered antibody of the invention or a cocktail thereof dissolved in an pharmaceutically acceptable carrier, preferably an aqueous carrier. A variety of aqueous carriers may be employed, e.g., 0.4% saline, 0.3% glycine and the like. These solutions are sterile and generally free of particulate matter. These solutions may be sterilized by conventional, well known sterilization techniques (e.g., filtration). The compositions may contain pharmaceutically acceptable auxiliary substances as required to approximate physiological conditions such as pH adjusting and buffering agents, etc. The concentration of the antibody of the invention in such pharmaceutical formulation can vary widely, i.e., from less than about 0.5%, usually at or at least about 1% to as much as 15 or 20% by weight and will be selected primarily based on fluid volumes, viscosities, etc., according to the particular mode of administration selected.

Thus, a pharmaceutical composition of the invention for intramuscular injection could be prepared to contain 1 mL sterile buffered water, and between about 1 ng to about 100 mg, e.g. about 50 ng to about 30 mg or more preferably, about 5 mg to about 25 mg, of an engineered antibody of the invention. Similarly, a pharmaceutical composition of the invention for intravenous infusion could be made up to contain about 250 ml of sterile Ringer's solution, and about 1 mg to about 30 mg and preferably 5 mg to about 25 mg of an engineered antibody of the invention. Actual methods for preparing parenterally administrable compositions are well known or will be apparent to those skilled in the art and are described in more detail in, for example, "Remington's Pharmaceutical Science", 15th ed., Mack Publishing Company, Easton, Pa.

It is preferred that the therapeutic agent of the invention, when in a pharmaceutical preparation, be present in unit dose forms. The appropriate therapeutically effective dose can be determined readily by those of skill in the art. To effectively treat a thrombotic or embolic disorder in a human or other animal, one dose of approximately 0.1 mg to approximately 20 mg per kg body weight of a protein or an antibody of this invention should be administered parenterally, preferably i.v. or i.m. Such dose may, if necessary, be repeated at appropriate time intervals selected as appropriate by a physician during the thrombotic response.

The antibodies, altered antibodies or fragments thereof described herein can be lyophilized for storage and reconstituted in a suitable carrier prior to use. This technique has been shown to be effective with conventional immunoglobulins and art-known lyophilization and reconstitution techniques can be employed.

The present invention will now be described with reference to the following specific, non-limiting examples.

EXAMPLE 1

Preparation and Screening of Anti-Factor IX Monoclonal Antibodies

Female Balb/C mice were injected with human factor IX purified as described in Jenny, R. et al., *Prep.Biochem.* 16, 227–245 (1986). Typically, each mouse received an initial injection of 100 ug protein dissolved in 0.15 mL phosphate-buffered saline (PBS) and mixed with 0.15 mL complete Freund's adjuvant. Booster immunizations of 50 ug protein in 0.15 mL PBS with 0.15. mL incomplete Freund's adjuvant were given approximately biweekly over a 2–3 month period. After the final boost, the mouse received 50 ug of Factor IX in PBS three days before spleen/myeloma cell fusions. Spleen cells were isolated from an immunized mouse and fused with NS-1 myeloma cells (Kohler, G. et al.,*Eur. J. Immunol.* 6, 292–295 (1976)) using polyethylene glycol as described by Oi, V. T. et al. in "Selected Methods in Cellular Immunology," Mishell, B. B. and Shigii, S. M., eds., Freeman Press, San Francisco. Following the fusion, the cells were resuspended in RPMI 1640 media containing 10% fetal calf sera and aliquots were placed in each well of four 24-well plates containing 0.5 mL of peritoneal lavage cell-conditioned media. On the following day, each well received 1.0 mL of $2\times10^{-4}$ M hypoxanthine, $8\times10^{-7}$ M aminopterin and $3.2\times10^{-5}$ M thymidine in RPMI 1640 media containing 10% fetal calf sera. The cells were fed every 3–4 days by removing half of the media and replacing it with fresh media containing $1\times10^{-4}$ M hypoxanthine and $1.6\times10^{-5}$ M thymidine.

Approximately two weeks later, 1.0 mL of hybridoma medium was removed from each well and tested for anti-Factor IX antibodies using an ELISA assay as described by Jenny, R. J. et al. in *Meth. Enzymol.* 222, 400–416 (1993). Briefly, factor IX was immmobilized onto plastic wells of 96-well microtiter plates. Hybridoma supernatants or dilutions of purified antibody were then incubated in the wells. The wells were washed and the presence of antibody-antigen complexes detected with a goat anti-murine immunoglobulin second antibody conjugated to horseradish peroxidase and the chromogenic substrate o-dianisidine.

Wells containing anti-Factor IX antibodies were subcloned by limiting dilution and grown in 96-well plates. Supernatant from the cloned hybridoma cell cultures were screened for antibody to Factor IX by the ELISA assay described above and cells from positive hybridomas were expanded, frozen, stored in liquid nitrogen and then grown as ascitic tumors in mice.

EXAMPLE 2

Self-Limiting Effect of Anti-Coagulation Factor Antibodies in Coagulation

The effect of increasing concentrations of anti-coagulation factor antibodies on activated partial thromboplastin time (aPTT) of human plasma was determined in a fibrometer (Becton-Dickinson Microbiology Systems, Cockeysville, Md.) using Baxter reference procedure LIB0293-J, 3/93 revision (Baxter Scientific, Edison, N.J.).

Prior to the start of the experiment, 2 to 3 mL of 0.02 M $CaCl_2$ in a 5 mL tube were placed into the heating chamber of the fibrometer. Human plasma samples were either freshly drawn and kept on ice or reconstituted per the manufacturer's recommendation from Hemostasis Reference Plasma (American Diagnostics, Greenwich, Conn.).

Unfractionated heparin from porcine intestinal mucosa (Sigma Chemical, St. Louis, Mo.), low molecular weight heparin from porcine intestinal mucosa (Lovenox®, enoxaparin sodium, Rhone-Poulenc Rorer Pharmaceuticals, Collegeville, Pa.) or mAb anticoagulants were prepared as approximately 50 uM stock solutions and serially diluted directly into the test plasma. A blank containing plasma without anticoagulant was included as a reference.

Two fibroTube® fibrometer cups were filled with 100 ul test plasma or 100 ul test plasma with anticoagulant and 125 ul of actin activated cephaloplastin reagent (Actin reagent, from rabbit brain cephalin in ellagic acid, available from Baxter Scientific), respectively and placed in the fibrometer wells at 37° C.

After one minute, 100 ul of actin reagent was transferred to a plasma-containing cup and the contents mixed several times with a pipette. After a 3 minute incubation, 100 ul of $CaCl_2$, prewarmed at 37° C., was added to the plasma-actin reagent mixture using a Automatic Pipette/Timer-trigger (Becton-Dickinson). The clotting times were noted and the results in FIG. 1 are presented as clotting times as a function of final concentrations of anticoagulant in the total assay volume of 300 ul. The nominal concentration of Factor IX in the assay is 30–40 nM.

The results shown in FIG. 1 demonstrate the effect of increasing concentrations of the murine anti-Factor IX mAbs BC1 and BC2 on aPTT clotting times. Both mAbs inhibit clotting by prolonging the aPTT and both mAbs reach a final saturating effect on the aPTT. The $IC_{50}$ values are similar at ~35 nM and ~50 nM for BC1 and BC2, respectively, but the difference in the maximum response to the two antibodies is marked. Saturating concentrations of BC1 increases the aPTT by about 50% to ~40 sec. BC2, on the other hand, increases the aPTT by 3.5-fold to about 90 sec. The therapeutic target zone used in anticoagulant therapy with heparin is highlighted. The results indicate that the two mAbs racket the heparin therapeutic aPTT range.

The properties of mabs BC1 and BC2 are summarized in Table I. Each of the BC mAbs recognizes both the zymogen, Factor IX, as well as the active protease, Factor IXa, but only BC2 is capable of blocking both zymogen activation as well as protease activity. BC1 and BC2 were found to cross-react with Cynomologous monkey Factor IX. Additionally, BC2 also cross-reacted with rat Factor IX.

TABLE I

Summary of in vitro Properties of Anti-Factor IX mAbs

|  | BC1 | BC2 |
| --- | --- | --- |
| Binds Factor IX | yes | yes |
| Binds Factor IXa | yes | yes |
| Inhibits IX to IXa conversion | no | yes |
| Inhibits IXa activity in Xase complex | yes | yes |
| Cofactor requirement | none | divalent metals $Ca^{2+} > Mn^{2-}$ |
| $\frac{aPTTmax}{aPTTnormal} \times 100\%$ | 150 | 350 |
| $IC_{50}$, nM | ~35 | ~50 |
| Species cross-reactivity | monkey | rat, monkey |
| Isotype | IgG1 | IgG2a |

Figure 2:
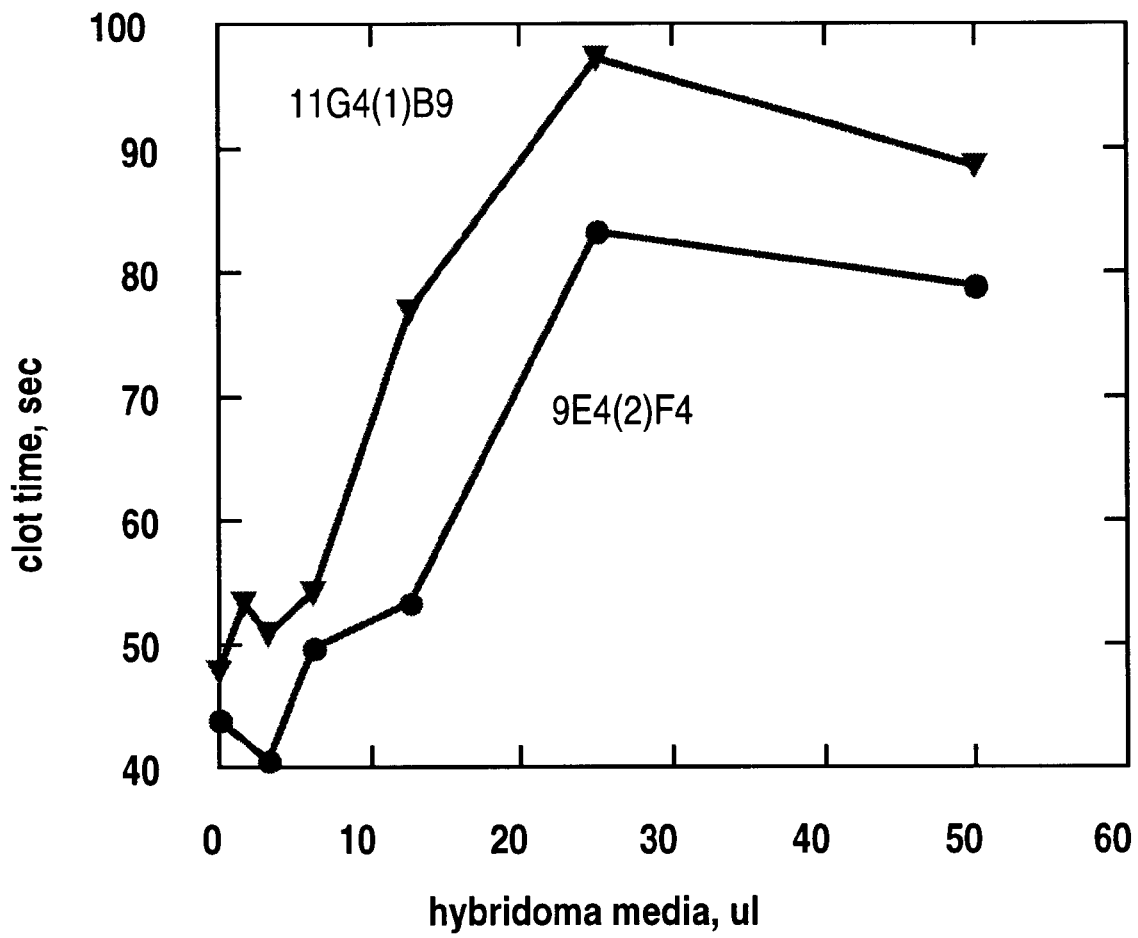
FIG. 2 is a graph of experimental results demonstrating the titration of normal human plasma with the murine anti-Factor IX mAbs 9E4(2)F4 and 11G4(1)B9.

The results shown in FIG. 2 demonstrate the effect of increasing concentrations of the anti-Factor IX mAbs 9E4(2)F4 and 11G4(1)B9 on aPTT clotting times. The plasma for the assay was diluted to one-half the normal concentration, giving an initial aPTT of 45 seconds. Both mAbs inhibit clotting by prolonging the aPTT and both mAbs reach a final saturating effect on the aPTT. Saturating concentrations of 9E4(2)F4 and 11G4(1)B9 increases the aPTT to ~90 to 100 seconds for 9E4(2)F4 and to ~80 seconds for 11G4(1)B9. The results indicate that the two mAbs are at the upper end of the heparin therapeutic aPTT range.

Figure 3:
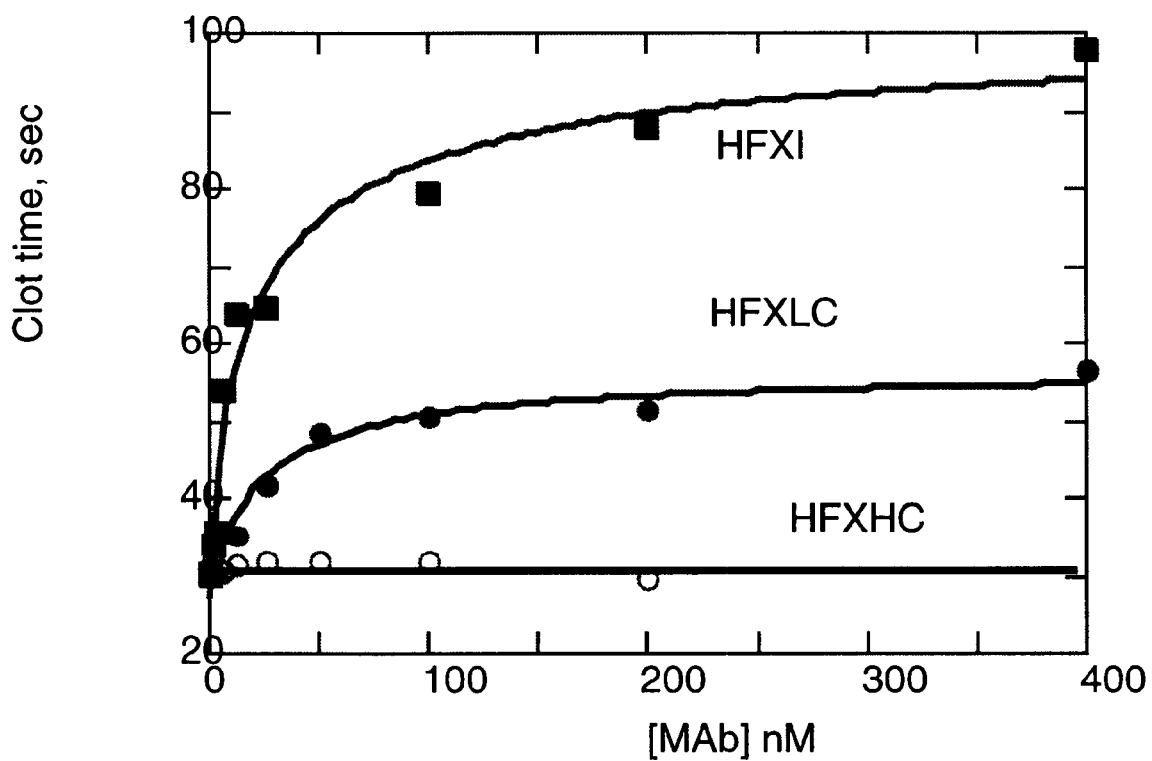
FIG. 3 is a graph of experimental results demonstrating the titration of normal human plasma with the murine anti-Factor X mAbs HFXHC and HFXLC and the murine anti-Factor XI mAb HFXI.

The results shown in FIG. 3 demonstrate the effect of increasing concentrations of the anti-Factor X mAbs HFXLC (vs. light chain epitope), HFXHC (vs. heavy chain epitope) and the anti-Factor XI mab HFXI on aPTT clotting times. These mAbs were obtained from Enzyme Research Laboratories (South Bend, Ind.). The mAbs HFXLC and HFXI inhibit clotting by prolonging the aPTT and both mAbs reach a final saturating effect on the aPTT. The IC50 value for HFXLC is ~40 nM; saturating concentrations increase the aPTT to ~60 seconds. The $IC_{50}$ value for HFXI is ~20 nM; saturating concentrations increase the aPTT to ~100 seconds. The results indicate that HFXLC is within the heparin therapeutic aPTT range while HFXI falls at the upper end of the heparin therapeutic range. The mAb HFXHC had no effect on aPTT clotting times.

Self-limiting prolongation of the aPTT was also observed with antibodies to Factor VIII, the cofactor to Factor IXa. For example, the anti-human Factor VIII antibody, SAF8C-IG, purchased from Affinity Biologicals, Inc., increased the aPTT to a maximum of about 65 sec. Half-maximal prolongation of the aPTT was achieved with about 100 nM antibody.

EXAMPLE 3

Efficacy of Murine Factor IX mAbs in Rat Thrombus Model

In order to evaluate the efficacy of anti-Factor IX antibodies in prevention of arterial thrombosis, the rat carotid artery thrombosis model as reported by Schumacher et al. in J. Cardio. Pharm. 22, 526–533 (1993) was adapted. This model consists of segmental injury to the carotid endothelium by oxygen radicals generated by $FeCl_3$ solution applied on the surface of the carotid artery.

In brief, rats were anesthetized with pentobarbitone sodium, the jugular vein cannulated for intravenous injections and the left femoral artery cannulated for blood pressure and heart rate monitoring. The carotid artery was isolated by aseptic technique via a surgical incision in the neck and equipped with a magnetic flow probe for blood flow measurement. After a period of stabilization, baseline parameters were established for the following variables: carotid blood flow, arterial pressure, heart rate, activated partial thromboplastin time (aPTT) and prothrombin time (PT). Thereafter, a premeasured Whatman filter paper soaked in 50% $FeCl_3$ solution was placed on the carotid artery for 15 minutes for complete injury of the underlying endothelial cells. After removal of the $FeCl_3$ soaked paper, the experiment was followed to completion over 60 minutes. At the end of the experiment, the carotid thrombus was extracted from the carotid artery and weighed.

All agents were administered 15 minutes prior to the onset of carotid injury. The following treatments were examined and compared to the Factor IX mAb BC2.

Figure 4:
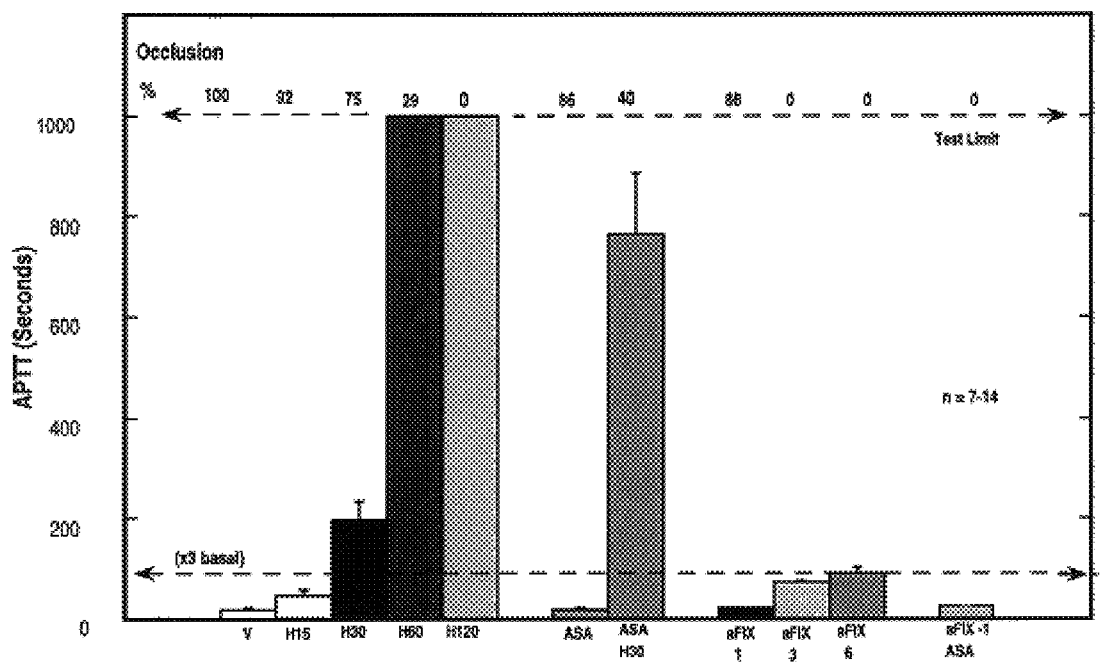
FIG. 4 is a histogram of experimental results demonstrating the effect of heparin, acetylsalicylic acid and murine Factor IX mabs on activated partial thromboplastin time (aPTT) at 60 minutes in a rat carotid thrombosis model.

1. Heparin: 15, 30, 60 or 120 U/kg bolus, followed by infusion of 0.5, 1, 2 or 4 U/kg/min, respectively over 60 minutes
2. Acetylsalicylic acid (ASA, aspirin): 5 mg/kg bolus
3. Anti-Factor IX mAb BC2: 1, 3 or 6 mg/kg bolus, followed by infusion 0.3, 1, or 2 ug/kg/min, respectively over 60 minutes
4. Heparin: 30 U/kg bolus+1 U/kg/min+ASA at 5 mg/kg
5. Anti-Factor IX mAb BC2: 1 mg/kg+0.3 ug/kg/min+ASA at 5 mg/kg FIGS. 4 and 5 demonstrate the comparative pharmacology of the anti-coagulant/thrombotic regimens by showing the effect of heparin, ASA and Factor IX mAb BC2 on aPTT (FIG. 4) and PT (FIG. 5).

The key index for bleeding diathesis, aPTT, was used as the primary criterion for evaluation of efficacy versus bleeding liabilities of the anti-coagulant/thrombotic agents used in the study. The results in FIG. 4 demonstrate the dose-dependent prolongation of aPTT by heparin with maximal prolongation of the clotting time, beyond the test limit, at the two higher doses. ASA alone did not significantly increase aPTT but in combination with heparin, a marked synergistic effect was observed. The Factor IX mAbs had a modest effect on aPTT and even at the highest dose, the increase in clotting time did not exceed the 3-fold limit of standard anti-coagulant practiced clinically. Most notably, the low dose of Factor IX mAb BC2 in combination with ASA did not change the aPTT.

Figure 5:
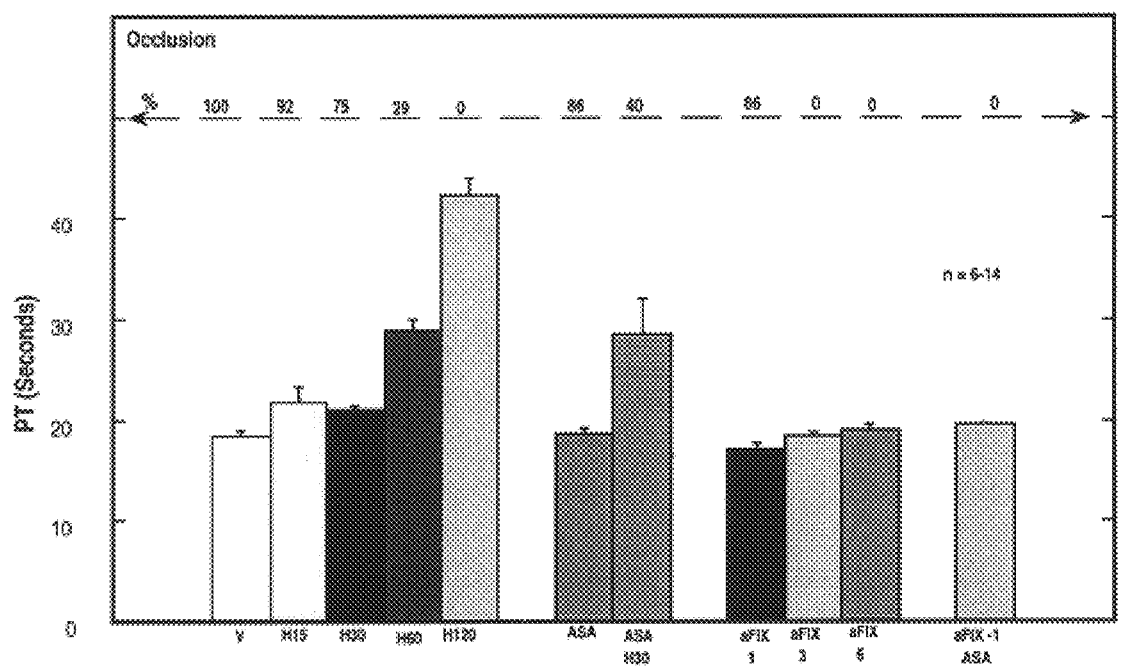
FIG. 5 is a histogram of experimental results demonstrating the effect of heparin, acetylsalicylic acid and murine Factor IX mabs on prothrombin time at 60 minutes in a rat carotid thrombosis model.

In FIG. 5, the data indicate that PT was also significantly prolonged by heparin, at the two higher doses, and by the ASA+heparin combination, but not by any of the Factor IX mAb doses alone or in combination with ASA.

Figure 6:
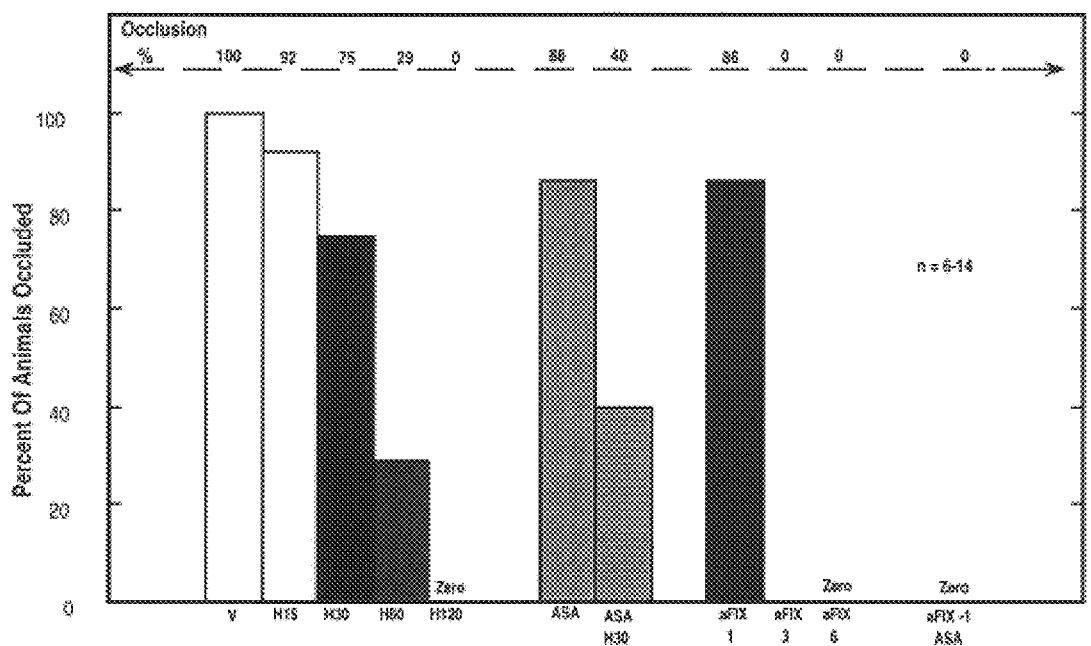
FIG. 6 is a histogram of experimental results demonstrating the effect of heparin, acetylsalicylic acid and murine Factor IX mabs on occlusion of carotid artery flow in a rat carotid thrombosis model.

The effect of heparin, ASA and Factor IX mAb on carotid artery occlusion is shown in FIG. 6. The results indicate that the carotid arteries of all of the vehicle-treated animals occlude in response to the injury. Heparin dose dependently inhibited the occlusion of the carotid artery. At the highest dose, heparin completely prevented the occlusion of the carotid artery; at this dose however, no coagulation could be initiated. ASA alone had only a minor effect on carotid occlusion. ASA in combination with heparin also failed to completely prevent carotid occlusion. Factor IX mAb completely blocked carotid occlusion at the two higher doses, which have not prolonged coagulation beyond the clinically desired target. The lower dose of Factor IX mAb, that largely failed to secure patency alone, demonstrated complete inhibition of carotid occlusion when administered in combination with ASA.

Figure 7:
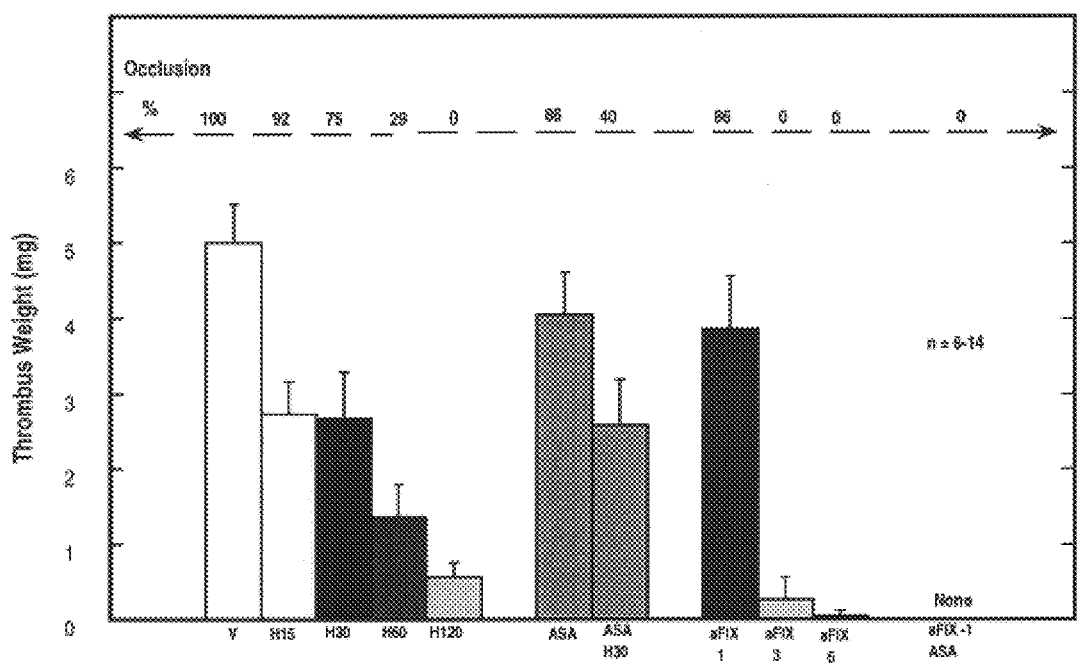
FIG. 7 is a histogram of experimental results demonstrating the effect of heparin, acetylsalicylic acid and murine Factor IX mabs on thrombus weight in a rat carotid thrombosis model.

The effect of heparin, ASA and Factor IX mAb on thrombus weight is shown in FIG. 7. Heparin dose-dependently reduced thrombus mass in the carotid artery. However, some residual thrombus was still found in the carotid artery in spite of complete blockade of coagulation. ASA alone or in combination with heparin (30 U/kg regimen) had only a partial effect on thrombus weight. Factor IX mAb dose-dependently reduced thrombus mass and the high dose virtually prevented completely thrombus formation. Moreover, the combination of the low dose anti-Factor IX mAb and ASA, a regimen that completely prevented carotid occlusion without adversely affecting the coagulation indices, completely prevented thrombus formation.

The studies conducted in the rat carotid thrombosis model clearly demonstrate the efficacy of Factor IX mAb in prevention of thrombosis in a highly thrombogenic arterial injury model. Most notably, the efficacy of the Factor IX mAb was demonstrated within the desired therapeutic anti-coagulant target defined by the aPTT. Furthermore, heparin, the current standard anticoagulant, reached efficacy comparable to Factor IX mAb only at doses that severely compromised coagulation to the extent of producing non-coagulable blood. Interestingly, the observed potentiation and synergy acquired by ASA joint treatment with heparin was also demonstrated when ASA was given with anti-Factor IX mAb. However, unlike the combination of heparin and ASA which resulted in potentiation of both the anti-thrombotic and anti-coagulant effects, the combination of Factor IX mAb and ASA resulted in potentiation of the anti-thrombotic efficacy with no consistent effect on ex vivo blood coagulation parameters. Taken together, the data show a superior antithrombotic capacity of Factor IX mAb compared to heparin, ASA or a combination of heparin and ASA.

EXAMPLE 4

Scanning Electron Microscopy of Rat Thrombosis Model

Segments of rat carotid artery were collected from sham, ferric chloride only and ferric chloride+6 mg/kg Factor IX antibody, 3/group, 15 minutes after application of ferric chloride. The arteries were fixed by perfusion with formaldehyde and ligated above and below the lesioned area. Fixed arteries were dehydrated, incubated in hexamethyldisilazane and dried in a desiccator. Dried arteries were opened lengthwise, placed on Scanning Electron Microscopy (SEM) stubs and sputter coated with gold.

SEM of sham arteries revealed an essentially normal endothelium with rare scattered platelets. There were a few breaks in the endothelium, probably as a result of mechanical damage during surgery and the underlying basement membrane was covered by a carpet of platelets. No evidence of thrombus formation was observed in the sham rats.

SEM of the arteries treated with ferric chloride revealed large mural thrombi which occupied a large portion of the lumen of the vessel. The thrombi were composed of aggregated platelets, red blood cells and amorphous and fibrillar proteinaceous material. The proteinaceous material is consistent with fibrin. The endothelium of the arteries was mostly obscured by the large thrombi. Where visible, the endothelium overlying the region treated with ferric chloride was covered by numerous adherent platelets and amorphous proteinaceous material.

SEM of the arteries treated with ferric chloride from rats also treated with Factor IX antibody, revealed the lumen of the vessels to be largely free of thrombus. The endothelium overlying the region treated with ferric chloride showed extensive damage and some areas were covered by adherent platelets and platelet aggregates but there was little or no proteinaceous material.

EXAMPLE 5

Anti-Factor IX mAb BC2 Heavy and Light Chain cDNA Sequence Analysis

Total RNA was purified by using TriReagent (Molecular Research Center, Inc., Cincinnati, Ohio) according to the manufacturer's protocol. RNA was precipitated with isopropanol and dissolved in 0.5% SDS and adjusted to 0.5M NaCl. Poly $A^+$ RNA was isolated with Dynabeads Oligo $(dT)_{25}$ (Dynal A. S., Lake Success, N.Y.) according to the manufacturer's protocol. Poly $A^+$ RNA was eluted from the beads and resuspended in TE buffer. Twelve aliquots of 100 ng of RNA were reverse transcribed with a RT-PCR kit per the manufacturer's instructions (Boehringer Mannheim Cat. No. 1483–188) using a dT oligo for priming. For the heavy chain, PCR amplifications of 6 RNA/DNA hybrids were carried out for 25 cycles using a murine IgG2a hinge primer (SEQ ID NO: 1) and a heavy chain signal sequence primer (SEQ ID NO: 2). Similarly, for the light chain, PCR amplificatons of 6 RNA/DNA hybrids were carried out for 25 cycles using a murine kappa primer (SEQ ID NO: 3) and a degenerate light chain signal sequence primer (SEQ ID NO: 4). The PCR products from each of the 12 amplifications were ligated in a PCR2000 vector (TA cloning Kit, Invitrogen, Cat. No. K2000-01). Colonies of recombinant clones were randomly picked and minipreparations of plasmid DNA were prepared using an alkaline extraction procedure described by Birnboim and Doly in *Nucl. Acids Res.* 7, 1513 (1979). The isolated plasmid DNA was digested with EcoRI and analyzed on a 0.8% agarose gel. Double-stranded cDNA inserts of the appropriate size, i.e., ~700 bp for the heavy chain and ~700 bp for the light chain, were sequenced by a modification of the Sanger method. The sequence of all 12 of the heavy and light chains were compared to generate a consensus BC2 heavy chain variable region sequence (SEQ ID NO: 5)and consensus BC2 light chain variable region sequence (SEQ ID NO: 6).

Sequence analysis of the BC2 heavy chain variable region cDNA revealed a 363 nucleotide open reading frame encoding a 121 amino acid sequence (SEQ ID NO: 7). The heavy chain CDR1, 2 and 3 sequences are listed in SEQ ID NOs: 8, 9 and 10, respectively.

Sequence analysis of the BC2 light chain variable region cDNA revealed a 321 nucleotide open reading frame encoding a 107 amino acid sequence (SEQ ID NO: 11). The light chain CDR1, 2 and 3 sequences are listed in SEQ ID NOs: 12, 13 and 14, respectively.

EXAMPLE 6

Humanized Antibodies

Six humanized antibodies designated SB 249413, SB 249415, SB 249416, SB249417, SB 257731 and SB 257732 were designed to contain the murine CDRs described above in a human antibody framework.

SB 249413

SB 249413 contains the heavy chain F9HZHC 1-0 and the light chain F9HZLC 1-0. The synthetic variable region humanized heavy chain F9HZHC 1-0 was designed using the first three framework regions of the heavy chain obtained from immunoglobulin RF-TS3'CL (Capra, J. D. et al., *J. Clin. Invest.* 86, 1320–1328 (1990) identified in the Kabat database as Kabpro:Hhc10w) and the BC2 heavy chain CDRs described previously. No framework amino acids substitutions which might influence CDR presentation were made. Four overlapping synthetic oligonucleotides were generated (SEQ ID NOs: 15, 16, 17 and 18) which, when annealed and extended, code for the amino acids representing the heavy chain variable region through and including CDR3 (SEQ ID NOs: 19 and 20). This synthetic gene was then amplified using PCR primers (SEQ ID NOs: 21 and 22) and ligated into the pCR2000 vector (TA cloning Kit, Invitrogen, Cat. No. K2000-01) and isolated from a SpeI, KpnI restriction digest. A second DNA fragment coding for the campath signal sequence including the first five amino acids of the variable region (SEQ ID NOs: 23 and 24) was made by PCR amplification of the appropriate region of a construct encoding a humanized anti-Respiratory Syncitial Virus heavy chain (SEQ ID NO: 25) with two primers (SEQ ID NOs: 26 and 27) and digesting with the restriction enzymes EcoRI and SpeI. The two fragments generated were ligated into an EcoRI, KpnI digested pFHZHC2-6pCD mammalian cell expression vector which contained the remainder of a human consensus framework 4 and IgG1 constant region. The vector contained a single amino acid mutation of the pFHZHC2-3pCD vector described in published International Patent Application No. WO94/05690. The final residue of framework 2 (residue 49) was mutated from Ser to Ala by digesting pFHZHC2-3pCD with XbaI and EcoR5 and inserting a linker generated from two synthetic oligonucleotides (SEQ ID NOs: 28 and 29). The sequence of the F9HZHC 1-0 insert is shown in SEQ ID NOs: 30 and 31.

The synthetic variable region humanized light chain F9HZLC 1-0 was designed using the framework regions of the human light chain obtained from immunoglobulin LS8' CL (Carmack et al., *J. Exp. Med.* 169, 1631–1643 (1989) identified in the Kabat database as Kabpro:Hk1318) and the BC2 light chain CDRs described previously. No framework amino acids substitutions which might influence CDR presentation were made. Two overlapping synthetic oligonucleotides were generated (SEQ ID NOs: 32 and 33) which, when annealed and extended, code for amino acids representing the light chain variable region (SEQ ID NOs: 34 and 35). This synthetic gene was then amplified using PCR primers (SEQ ID NOs: 36 and 37) and ligated into the pCR2000 vector (TA cloning Kit, Invitrogen, Cat. No. K2000-01), and isolated from a ScaI, SacII restriction digest. A second DNA fragment coding for the campath signal sequence including the first two amino acids of the variable region (SEQ ID NOs: 38 and 39) was made by PCR amplification of the the appropriate region of a construct encoding a humanized anti-Respiratory Syncitial Virus heavy chain (SEQ ID NO: 25) with the two primers (SEQ ID NOs: 26 and 40) and digesting with the restriction enzymes EcoRI and ScaI. The two fragments generated were ligated into an EcoRI, SacII digested pFHzLC1-2pCN mammalian cell expression vector which contained the remainder of a human framework 4 and kappa constant region. The vector contained a single amino acid mutation of the pFHZLC1-1pCN vector described in published International Patent Application No. WO94/05690. A framework 2 residue was mutated from Ser to Pro by digesting pFHZLC1-pCN with SmaI and Kpn1 and inserting a linker generated from two synthetic oligonucleotides (SEQ ID NOs: 41 and 42). The sequence of the F9HZLC 1-0 insert is shown in SEQ ID NOs: 43 and 44.

SB 249415

SB 249415 contains the heavy chain F9HZHC 1-1 and the light chain F9HZLC 1-1. These heavy and light chain constructs are based on F9HZHC 1-0 and F9HZLC 1-0, respectively, however, they have framework amino acid substitutions which can influence CDR presentation.

F9HZHC 1-1 has three framework amino acid substitutions which might influence CDR presentation. Two overlapping synthetic oligonucleotides were generated (SEQ ID NOs: 45 and 46), which when annealed and extended, code for amino acids representing the altered portion of the heavy chain variable region altered (SEQ ID NOs: 47 and 48). This synthetic gene was then amplified using PCR primers (SEQ ID NOs: 49 and 50), ligated into the pCR2000 vector (TA cloning Kit, Invitrogen, Cat. No. K2000-01) and isolated from a EcoNI, KpnI restriction digest. This fragment was ligated into EcoNI, KpnI digested F9HZHC1-0 (SEQ ID NO: 30) vector. The sequence of the F9HZHC 1-1 insert is shown in SEQ ID NOs: 51 and 52.

F9HZLC 1-1 has four framework amino acids substitutions which can influence CDR presentation. Two synthetic oligonucleotides were generated (SEQ ID NOs: 53 and 54), which when annealed, have KpnI and BamHI cohesive ends, and code for amino acids representing the altered portion of the light chain variable region (SEQ ID NO: 55). F9HZLC 1-0 (SEQ ID NO: 43) was digested with the restriction enzymes KpnI and BamHI and ligated to the synthetic DNA. The sequence of the F9HZLC 1-1 insert is shown in SEQ ID NOs: 56 and 57.

SB 249416

SB 249416 contains the heavy chain F9HZHC 1-1 (described above) (SEQ ID NO: 52) and the light chain F9HZLC 1-2. The light chain construct is based on F9HZLC 1-1, however, it has one additional framework amino acid substitution which can influence CDR presentation.

Two synthetic oligonucleotides were generated (SEQ ID NOs: 58 and 59), which when annealed, have BamHI and XbaI cohesive ends and code for amino acids representing the altered portion of the light chain variable region (SEQ ID NO: 60). F9HZLC 1-1 (SEQ ID NO: 56) vector was digested with the restriction enzymes BamHI and XbaI and ligated to the synthetic DNA. The sequence of the F9HZLC 1-2 insert is shown in SEQ ID NOs: 61 and 62.

SB 249417

SB 249417 contains the heavy chain F9HZHC 1-1 (described above) (SEQ ID NO: 52) and the light chain F9HZLC 2-0. A F9HZLC 2-0 synthetic variable region humanized light chain was designed using the framework regions of the human light chain obtained from immunoglobulin REI (Palm and Hilschmann, Z. Physiol. Chem. 354, 1651–1654 (1973) identified in the Kabat database as Kabpro: HKL111) and the BC2 light chain CDRs described previously. Five amino acid consensus human substitutions were introduced. Six framework amino acids murine substitutions which can influence CDR presentation were made. Two overlapping synthetic oligonucleotides were generated (SEQ ID NOs: 63 and 64) which, when annealed and extended, code for amino acids representing the light chain variable region (SEQ ID NOs: 65 and 66). This synthetic gene was then amplified using PCR primers (SEQ ID NOs: 67 and 68), ligated into the pCR2000 vector (TA cloning Kit, Invitrogen, Cat. No. K2000-01) and isolated from a ScaI, SacII restriction digest. A second DNA fragment coding for the campath signal sequence including the first two amino acids of the variable region (SEQ ID NO: 38) was made by PCR amplification of the the appropriate region of a construct encoding a humanized anti-Respiratory Syncitial Virus heavy chain (SEQ ID NO: 25) with two primers (SEQ ID NOs: 26 and 69) and digesting with the restriction enzymes EcoRI and ScaI. A third DNA fragment encoding the remainder of a human framework 4 (SEQ ID NO: 70) and having SacII and NarI cohesive ends was generated by annealing two synthetic oligonucleotides (SEQ ID NOs: 71 and 72). F9HZLC 1-0 (SEQ ID NO: 43) was digested with the restriction enzymes EcoRI and NarI and ligated to the three DNA fragments. The sequence of the F9HZLC 2-0 insert is shown in SEQ ID NOs: 73 and 74.

SB 257731

SB 257731 contains the heavy chain F9HZHC 1-1 (SEQ ID NO: 52) and the light chain F9HZLC 1-3, a single amino acid mutation of F9HZLC 1-2 (SEQ ID NO: 62). F9HZLC 1-2 was PCR amplified with two primers (SEQ ID NOs: 26 and 69) and digested with the restriction enzymes EcoRI and ScaI. A 94 bp fragment (SEQ ID NOs: 75 and 76) was isolated. The fragment was ligated into EcoRI, ScaI digested F9HZLC 1-2 vector to produce the light chain construct F9HZLC 1-3. The sequence of the F9HZLC 1-3 insert is shown in SEQ ID NOs: 77 and 78.

SB 257732

SB 257732 contains the synthetic variable region humanized heavy chain F9HZHC 3-0 and light chain F9HZLC 3-0. Four overlapping synthetic oligonucleotides were generated (SEQ ID NOs: 79, 80, 81 and 82) which, when annealed and extended, code for the amino acids representing the heavy chain variable region being altered (SEQ ID NOs: 83 and 84). This synthetic gene was then amplified using PCR primers (SEQ ID NOs: 85 and 86), ligated into the pCR2000 vector (TA cloning Kit, Invitrogen, Cat. No. K2000-01) and isolated from a StuI, KpnI restriction digest. The isolated fragment was ligated into StuI, KpnI digested F9HZHC1-1 (SEQ ID NO: 52) vector. This vector was then digested with EcoRI, SpeI to remove the signal sequence. A DNA fragment coding for the campath signal sequence (SEQ ID NO: 23) including the first five amino acids of the variable region was made by PCR amplification of F9HZHC1-0 with two primers (SEQ ID NOs: 26 and 87) and digesting with the restriction enzymes EcoRI and SpeI. The fragment generated was ligated into the vector. The sequence of the F9HZHC3-0 insert is shown in SEQ ID NOs: 88 and 89.

Four overlapping synthetic oligonucleotides were generated (SEQ ID NOs: 90, 91, 92 and 93) which, when annealed and extended, code for amino acids representing the light chain variable region (SEQ ID NOs: 94 and 95). This synthetic gene was then amplified using PCR primers (SEQ ID NOs: 96 and 97) and ligated into the pCR2000 vector (TA cloning Kit, Invitrogen, Cat. No. K2000-01), and isolated from a ScaI, NarI restriction digest. The isolated fragment was ligated into ScaI, NarI digested F9HZLC1-3 (SEQ ID NO: 77) vector. The sequence of the F9HZLC3-0 insert is shown in SEQ ID NOs: 98 and 99.

The humanized anti-Factor IX mAbs were expressed in CHO cells. A DG-44 cell line adapted for suspension growth in serum-free medium was grown in 100 ml of protein-free medium containing 1×nucleosides and 0.05% F68 in 250 ml disposable sterile erlenmeyer flasks (Corning) on a Innova 2100 platform shaker (New Brunswick Scientific) at 150 rpm at 37° C. in a 5% $CO_2$, 95% air humidified incubator. These cells were passaged at $4 \times 10^5$ cells/ml twice weekly. 15 ug each of the pCN-Lc-Light Chain and pCD-Hc-heavy chain vectors were linearized by digestion with Not1, co-precipitated under sterile conditions and resuspended in 50 ul of 1×TE buffer (10 mM Tris, 1 mM EDTA, pH 7.5). The DNA was electroporated using a Bio-Rad Gene Pulser (Bio-Rad Laboratories) into the Acc-098 cells using the technique of Hensley et al. in *J. Biol. Chem.* 269, 23949–23958 (1994). $1.2 \times 10^7$ cells were washed once in 12.5 ml of ice cold PBSucrose (PBS, 272 mM sucrose, 7 mM sodium phosphate pH 7.4, 1 mM $MgCl_2$), resuspended in 0.8 ml of PBS, added to 50 ul of the DNA solution and incubated on ice for 15 min. The cells were pulsed at 380 V and 25 microfarads, then incubated on ice for 10 min. Cells were plated into 96 well culture plates at $5 \times 10^5$ cells/plate in maintenance medium for 24 hr prior to selection. Cells were selected for resistance to 400 ug/ml G418 (Geneticin, Life Technologies, Inc.) in maintenance medium. 24 hr prior to assay, the cells were fed with 150 ul of the maintenance medium.

Conditioned medium from individual colonies was assayed using an electrochemiluminescence (ECL) detection method on an Origen analyzer (IGEN, Inc.). See Yang et al., *Biotechnology* 12, 193–194 (1994).

All solutions necessary for the performance of the assays (assay buffer) and for the operation of the analyzer (cell cleaner) were obtained from IGEN. The antibodies (anti-human IgG (g-chain specific), Sigma Chemicals and F(ab')$_2$ Fragment to Human IgG (H+L), Kirkegaard & Perry Laboratories Inc.) were labelled with TAG-NHS-ester (IGEN, Inc.) at a 7:1 molar ratio of TAG:protein, while the Protein A (Sigma) was labelled with Biotin-LC-Sulfo-NHS-ester (IGEN, Inc.) at a 20:1 molar ratio Biotin:protein, both according to IGEN's recommendations. Streptavidin-coated magnetic beads (M-280) were obtained from Dynal.

Immunoassays were performed using the following protocol: per sample, 50 ul of the Streptavidin-coated beads (final concentration 600 ug/ml diluted in PBS, pH7.8, with 1.25% Tween) were mixed with 50 ul Biotin-Protein A (final concentration 1ug/diluted in PBS, pH7.8, with 1.25%

Tween) and incubated at room temperature for 15 min with agitation, 50 ul of the TAG antibodies (a mixture with a final concentration of 1.25 ug/ml F(ab')$_2$ Fragment to Human IgG (H+L) and 0.25 ug/ml Anti-Human IgG (g-chain specific) diluted in PBS, pH7.8, with 1.25% Tween) were added, the solution was then added to 50 ul of conditioned medium and incubated with agitation at room temperature for 1 hr. 200 ul of assay buffer was added to the reaction mix and the sample analyzed on the origen I analyzer to measure ECL. The results indicated that approximately 20–37% of the colonies assayed secrete over 15 ng/ml of the antibody with an average expression of about 150 ng/ml.

Humanized anti-Factor IX mAbs were purified from the conditioned media using a Procep A capture step followed by ion-exchange chromatography to reduce the DNA burden. Procep A sorbent material (Bioprocessing Ltd., Durham, England) was used to prepare a column with a 1:1 diameter to height ratio. Clarified conditioned media was loaded onto the column at about 150 cm/hr. The column was washed sequentially with phosphate buffered saline (PBS), PBS containing 1 M NaCl, and finally with PBS. The bound material was recovered with 0.1 M acetic acid elution. The eluate was adjusted to pH 5.5 and was diluted (1:4) with water. The diluted solution was loaded onto an S-Sepharose column (2.5×13 cm) which was pre-equilibrated with 20 mM sodium acetate, pH 5.5 at 80 cm/hr. The column was washed with the acetate buffer until a steady baseline was obtained and the bound protein was eluted with 20 mM sodium phosphate, pH 7.4 at 25 cm/hr. The eluted material was filtered with a 0.4 micron membrane and stored at 4° C.

EXAMPLE 7

Mouse-Human Chimeric Antibody 100 ng of BC2 RNA were reverse transcribed with a RT-PCR kit per the manufacturer's instructions (Boehringer Mannheim Cat. No. 1483-188) using a dT oligo for priming, and PCR amplified with synthetic ScaI (SEQ ID NO: 100) and NarI (SEQ ID NO: 101) primers to produce the BC2 light chain variable region with Sca1, Nar1 ends (SEQ ID NOs: 102 and 103). This DNA was ligated into ScaI, NarI digested F9HZHC1-3 (SEQ ID 77) and digested with ScaI, NarI to produce a mouse-human chimeric light chain F9CHLC (SEQ ID NOs: 104 and 105).

100 ng of BC2 RNA were reverse transcribed with a RT-PCR kit per the manufacturer's instructions (Boehringer Mannheim Cat. No. 1483-188) using a dT oligo for priming, and PCR amplified with synthetic SpeI (SEQ ID NO: 106) and NheI (SEQ ID NO: 107) primers to produce the BC2 heavy chain variable region with Spe1, Nhe1 ends (SEQ ID NOs: 108 and 109). The campath signal sequence was PCR amplified from the RSVHZ19 heavy chain (SEQ ID NO: 25) with EcoRI (SEQ ID 26) and SpeI (SEQ ID 87) primers. These two DNA fragments were ligated into a EcoRI, NheI digested IL4CHHCpcd vector described in published International Patent Application No. WO95/07301, replacing the IL4 variable region with the BC2 Factor IX mouse variable region, to produce a mouse-human chimeric heavy chain F9CHHC (SEQ ID Nos: 110 and 111).

Co-transfection and purification of the mouse-human chimeric antibody chαFIX was accomplished as described above for the humanized constructs.

EXAMPLE 8

Efficacy of Humanized Factor IX mAbs in Rat Thrombus Model

In order to evaluate the efficacy of humanized anti-Factor IX antibodies in prevention of arterial thrombosis, the rat carotid artery thrombosis model as described above in Example 3 was used. Baseline parameters were established for carotid blood flow, arterial pressure, heart rate, vessel patency and activated partial thromboplastin time (aPTT). Fifteen minutes thereafter, carotid injury was effected for 10 minutes. The parameters were determined 60 minutes after onset of carotid injury. Carotid thrombus was also extracted from the carotid artery and weighed.

All agents were administered intravenously 15 minutes before the onset of carotid injury. The following treatments were examined and compared to the anti-Factor IX mAb BC2.

1. Vehicle
2. chαFIX: 3 mg/kg bolus
3. SB 249413: 3 mg/kg bolus
4. SB 249415: 3 mg/kg bolus
5. SB 249416: 3 mg/kg bolus
6. SB 249417: 3 mg/kg bolus
7. SB 257731: 3 mg/kg bolus
8. Heparin: 60 units/kg bolus+2 units/kg/min infusion.

Figure 8:
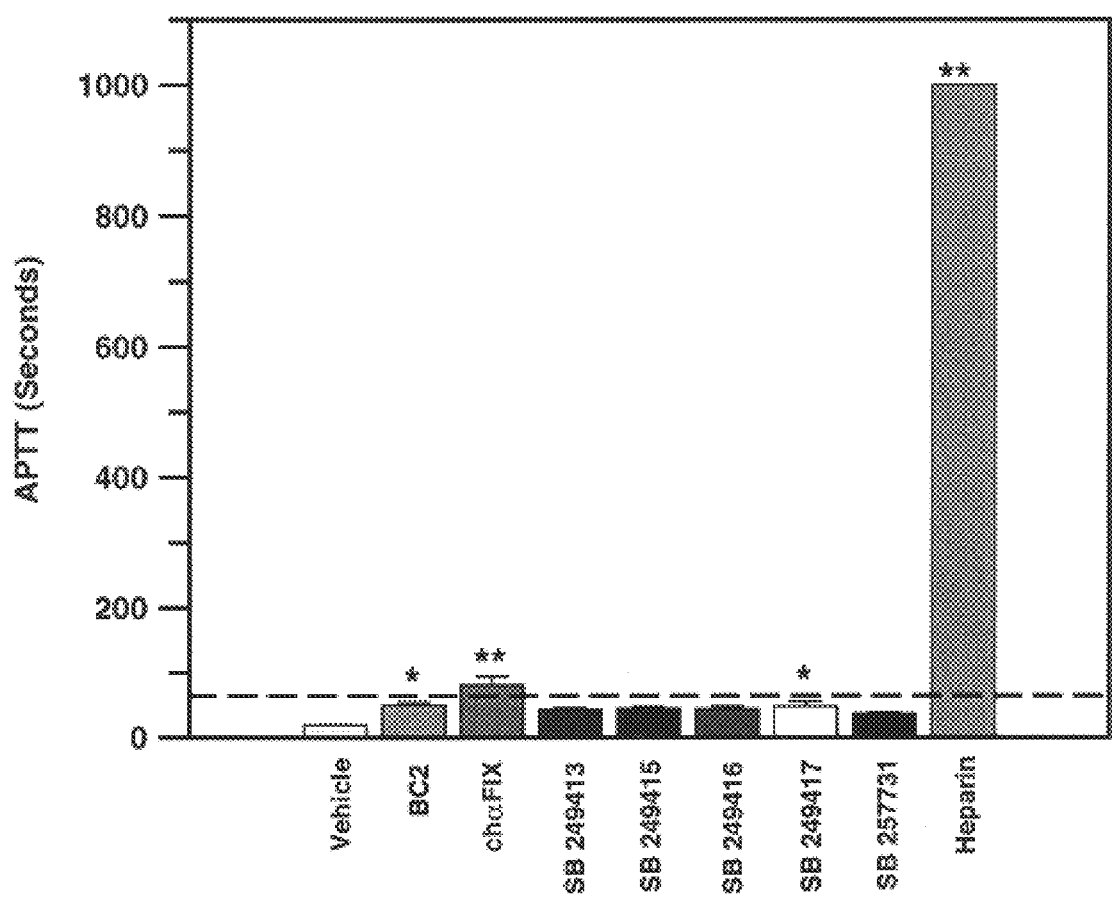
FIG. 8 is a histogram of experimental results demonstrating the effect of heparin, the murine Factor IX mab BC2, a chimeric Factor IX mab and humanized factor IX mAbs on aPTT at 60 minutes in a rat carotid thrombosis model.

The aPTT was used as the primary criterion for evaluation of efficacy versus bleeding liabilities of the anti-coagulant/thrombotic agents used in the study. The results in FIG. 8 demonstrate that the humanized Factor IX mabs SB 249413, SB 249415, SB 249416, SB 249417 and SB 257731 had a modest effect on aPTT at 3.0 mg/kg which is within the clinical accepted range.

Figure 9:
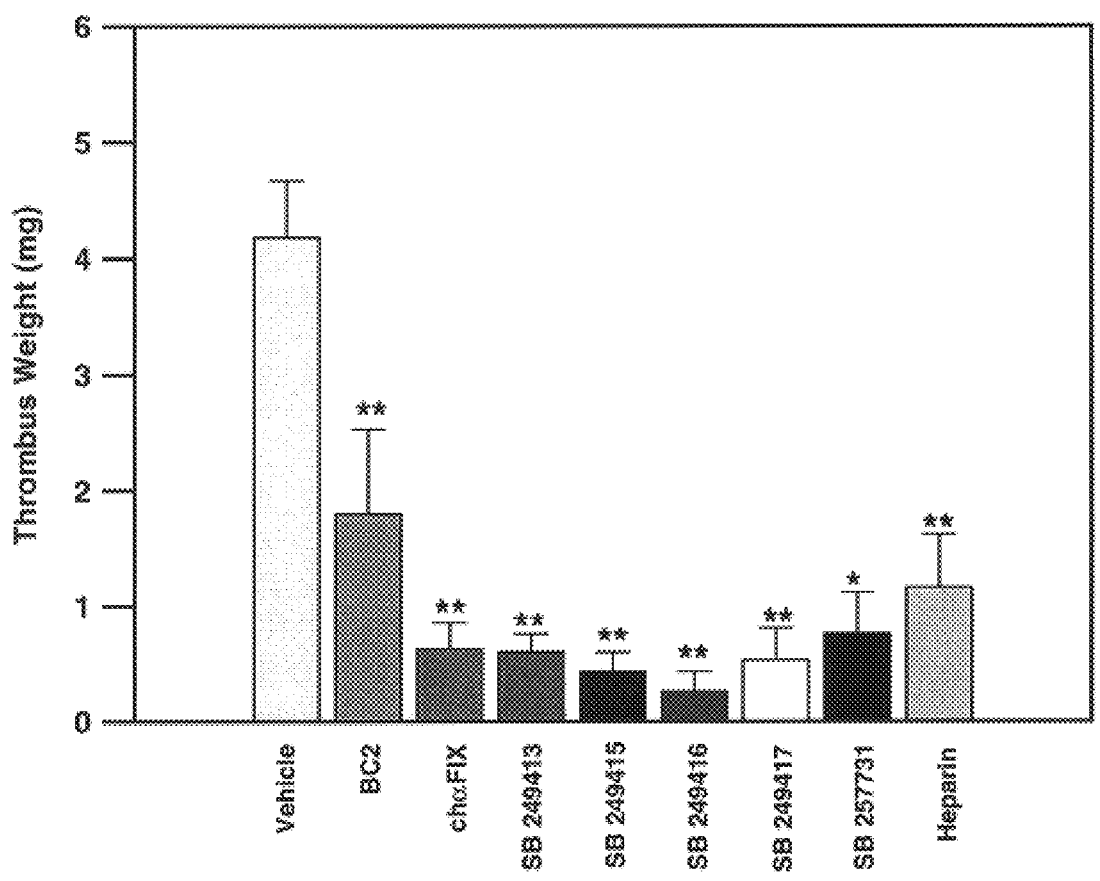
FIG. 9 is a histogram of experimental results demonstrating the effect of heparin, the murine Factor IX mab BC2, a chimeric Factor IX mab and humanized factor IX mAbs on thrombus weight in a rat carotid thrombosis model.

The effect of the Factor IX mAbs on thrombus mass is shown in FIG. 9. The results indicate that all of the humanized mAbs are equally effective in reducing thrombus mass.

The studies conducted in the rat carotid thrombosis model clearly demonstrate the efficacy of the humanized Factor IX mAbs in prevention of thrombosis in a highly thrombogenic arterial injury model. Most notably, the efficacy of all of the humanized Factor IX mAbs was demonstrated within the desired therapeutic anticoagulant target defined by the aPTT.

EXAMPLE 9

Antibody Biochemical and Biophysical Properties

The molecular mass of SB 249417 was determined by MALD-MS to be 148,000 Da. Analytical ultracentrifugation of SB 249417 gave an identical value. In the presence of Factor IX plus $Ca^{2+}$, the antibodies derived from BC 2 sedimented with a mass of 248,000 Da corresponding to the combined mass of the mAb and two molecules of Factor IX. No evidence of higher ordered aggregates was observed in the presence or absence of Factor IX.

The kinetics of Factor IX binding to SB 249417 was assessed by BIAcore analysis with antibody bound to an immobilized protein A surface. Recombinant human Factor IX (rhFIX, Genetics Institute) at 49 nM was used and measurements performed in the presence of 5 mM $Ca^{2+}$. The interaction was characterized by rapid association, kass= $2.0 \times 10^5$ $M^{-1}$ $s^{-1}$ and relatively slow off-rate, kdiss=$4.1 \times 10^{-4}$ $s^{-1}$. The calculated $K_d$ for Factor IX binding was 1.9 nM.

Table 1 summarizes the biophysical properties of SB 249417.

TABLE 1

Summary of the Biophysical Properties of SB 249417

| | |
|---|---|
| Isotype | IgG1, kappa |
| Purity by SDS-PAGE | >95% (under reducing conditions) |
| Molecular Weight | |
| Mass Spectrometry | 148,000 Da |
| Analytical Ultracentrifugation | 148,000 Da |
| Stoichiometry of Factor IX Binding | |
| Isothermal Titration Calorimetry | 1.5 moles Factor IX: 1 mole mAb |
| Factor IX Binding Affinity | |
| Isothermal Titration Calorimetry | Kd = 4 nM at 25° C. |
| Biosensor | Kd = 2 nM |
| Factor IX Binding Kinetics | |
| Biosensor | $k_{ass} = 2.0 \times 10^5 \, M^{-1} \, s^{-1}$ |
| | $k_{diss} = 4 \times 10^{-4} \, s^{-1}$ |

Table 2 summarizes the factor IX binding properties of mAbs of the present invention. The calculated dissociation constants were essentially identical within experimental error.

TABLE 2

Kinetics of Factor IX Binding to Anti-Factor IX mAbs

| mAb | $k_{ass}$ $(M^{-1}s^{-1})$ | $k_{diss}$ $(s^{-1})$ | calc. $K_D$ (nM) |
|---|---|---|---|
| SB 249417 | $2.0 \times 10^5$ | $4.1 \times 10^{-4}$ | 1.9 |
| BC2 | $4.8 \times 10^5$ | $9.1 \times 10^{-4}$ | 1.9 |
| Chf9 | $2.4 \times 10^5$ | $3.0 \times 10^{-4}$ | 1.3 |
| SB 249413 | $6.5 \times 10^5$ | $2.8 \times 10^{-3}$ | 3.7–5.1 |
| SB 249415 | $7.5 \times 10^5$ | $1.8 \times 10^{-4}$ | 1.1–2.3 |
| SB 249416 | $5.2 \times 10^5$ | $4.1 \times 10^{-4}$ | 0.8 |
| SB 257731 | $9.2 \times 10^5$ | $9.9 \times 10^{-4}$ | 1.1 |
| SB 257732 | $1.1 \times 10^6$ | $1.2 \times 10^{-3}$ | 1.5 |

The interactions between rhFIX and SB 249417, BC2 and other humanized constructs were characterized by titration microcalorimetry, which measures binding interactions in solution from the intrinsic heat of binding. Nine injections of 106 uM FIX were made into the calorimeter containing 2 uM mAb SB 249417. Binding was detected in the first 4 injections as exothermic heats. At the last 5 injections the mAb binding sites were saturated with FIX and only background heats of mixing were observed. The results indicated that the equivalence point occurred at a molar binding ratio near 2 FIX per mAb, as expected. Nonlinear least squares analysis of the data yield the binding affinity.

The rhFIX affinities of the mAbs were measured over a range of temperature from 34–44° C. in 10 mM HEPES, 10 mM $CaCl_2$, 150 mM NaCl, pH 7.4. These data allow the affinity at 37° C. to be determined directly and the affinity at 25° C. to be calculated from the van't Hoff equation. The data in Table 3 indicate that the affinities of SB 249417, BC2 and its other humanized constructs are within error (a factor of 2) the same.

TABLE 3

Titration Calorimetry Results for Anti-FIX mAbs

| mAb | Kd, nM at 25° C. | Kd, nM at 37° C. | Molar Binding Ratio FIX/mAb |
|---|---|---|---|
| BC2 | 10 | 20 | 1.4 |
| SB 249413 | 6 | 12 | 1.9 |
| SB 249415 | 3 | 7 | 1.7 |
| SB 249417 | 4 | 12 | 1.5 |
| SB 257732 | 4 | 9 | 1.8 |

The mAbs SB 249413, SB 249415, SB 249417 and SB 257732 all exhibited very similar thermal stabilities by differential scanning calorimetry. Their unfolding Tms ranged from 70–75° C. indicating high stability against thermally induced denaturation.

EXAMPLE 10

Mechanism of Antibody-Mediated Inhibition of Factor IX

A library of chimeric constructs composed of sequences of Factor IX spliced into the framework of the homologous protein Factor VII was constructed and used to map the epitope for the Factor IX BC2 mAb. See Cheung et al., Thromb. Res. 80, 419–427 (1995). Binding was measured using a BiaCore 2000 surface plasmon resonance device. The BC2 antibody was coupled directly to the chip using the NHS/EDC reaction. Binding was measured by 2 min of contact time at 20 uL/min with 200 nM of each of the given constructs in 25 mM MOPS, pH 7.4, 0.15 M NaCl, 5 mM $CaCl_2$. Dissociation was monitored for 3 min using the same buffer with no protein. No binding was detected to the wild type construct in the presence of 50 mM EDTA. The data are presented in Table 4.

TABLE 4

Summmary of Binding of Factor IX Constructs to BC2 Antibody

| Construct | Degree of Binding |
|---|---|
| Plasma IXa | Binds |
| r-IX | Binds |
| Plasma VII | No Binding |
| IX LC/VII HC | Binds |
| IX-A/VII | Binds |
| VII gla/IX | No Binding |
| VII-A/IX | No Binding |
| VII gla (IX 3-11)/IX | Binds |
| VII gla (IX 3-6)/IX | Very Low Binding |
| VII gla (IX 9-11)/IX | Very Low Binding |
| IX K5A | Binds |

These data indicate that the constructs containing the Factor IX light chain and Factor VII heavy chain (IX LC/VII HC); the Factor IX gla and aromatic stack domains (IX-A/VII); residues 3–11 of Factor IX gla domain within the Factor VII gla domain (VII gla (IX 3–11)/IX); and Factor IX having a lysine to alanine substitution at residue 5 (IX K5A)

exhibit binding to BC2. The VII gla (IX 3–11)/IX construct exhibited BC2 binding equivalent to wild type Factor IX (plasma IXa and r-IX). Thus, the BC2 antibody binds to an epitope contained within residues 3–11 of the Factor IX gla domain.

The present invention may be embodied in other specific forms without departing from the spirit or essential attributes thereof, and, accordingly, reference should be made to the appended claims, rather than to the foregoing specification, as indicating the scope of the invention.

What is claimed is:

1. An altered antibody comprising a heavy chain and a light chain, wherein the framework regions of said heavy and light chains are derived from at least one selected antibody and the amino acid sequences of the heavy chain complementarity determining regions (CDRs) are as set forth in SEQ ID NOs: 8, 9 and 10 and the amino acid sequences of the light chain CDRs are as set forth in SEQ ID NOs: 12, 13 and 14.

2. The altered antibody of claim 1 which is humanized.

3. The humanized antibody of claim 2 wherein the heavy chain has the amino acid sequences set forth in SEQ ID NOs: 31, 52 or 89 or of functional fragments thereof.

4. The humanized antibody of claim 2 wherein the light chain has the amino acid sequence set forth in SEQ ID NOs: 44, 57, 62, 74, 78 or 99 or of functional fragments thereof.

5. The humanized antibody of claim 2 wherein the heavy chain has the amino acid sequence set forth in SEQ ID NO: 31 and the light chain has the amino acid sequence set forth in SEQ ID NO: 44.

6. The humanized antibody of claim 2 wherein the heavy chain has the amino acid sequence set forth in SEQ ID NO: 52 and the light chain has the amino acid sequence set forth in SEQ ID NO: 57.

7. The humanized antibody of claim 2 wherein the heavy chain has the amino acid sequence set forth in SEQ ID NO: 52 and the light chain has the amino acid sequence set forth in SEQ ID NO: 62.

8. The humanized antibody of claim 2 wherein the heavy chain has the amino acid sequence set forth in SEQ ID NO: 52 and the light chain has the amino acid sequence set forth in SEQ ID NO: 74.

9. The humanized antibody of claim 2 wherein the heavy chain has the amino acid sequence set forth in SEQ ID NO: 52 and the light chain has the amino acid sequence set forth in SEQ ID NO: 78.

10. The humanized antibody of claim 2 wherein the heavy chain has the amino acid sequence set forth in SEQ ID NO: 89 and the light chain has the amino acid sequence set forth in SEQ ID NO: 99.

11. A pharmaceutical composition comprising the altered antibody of claim 2 and a pharmaceutically acceptable carrier.

12. The pharmaceutical composition of claim 11 further comprising acetylsalicylic acid.

13. A humanized antibody comprising a heavy chain having the amino acid sequence set forth in SEQ ID NO: 52 and a light chain having the amino acid sequence set forth in SEQ ID NO: 74.

* * * * *

```
                              SEQUENCE LISTING (1) GENERAL INFORMATION:

(iii) NUMBER OF SEQUENCES: 111

(2) INFORMATION FOR SEQ ID NO:1:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(xi) SEQUENCE DESCRIPTION: SEQ ID NO:1:

CATCCTAGAG TCACCGAGGA                                                    20

(2) INFORMATION FOR SEQ ID NO:2:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(xi) SEQUENCE DESCRIPTION: SEQ ID NO:2:

AGCTGCCCAA AGTGCCCAAG C                                                  21

(2) INFORMATION FOR SEQ ID NO:3:

(i) SEQUENCE CHARACTERISTICS:
          (A) LENGTH: 36 base pairs
          (B) TYPE: nucleic acid
          (C) STRANDEDNESS: single
          (D) TOPOLOGY: linear (ii) MOLECULE TYPE: cDNA (iii) HYPOTHETICAL: NO (iv) ANTISENSE: NO (v) FRAGMENT TYPE:
```

(vi) ORIGINAL SOURCE:

(xi) SEQUENCE DESCRIPTION: SEQ ID NO:3:

CTAACACTCA TTCCTGTTGA AGCTCTTGAC AATGGG         36

(2) INFORMATION FOR SEQ ID NO:4:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(xi) SEQUENCE DESCRIPTION: SEQ ID NO:4:

GATTTTCARG TGCAGATTTT C         21

(2) INFORMATION FOR SEQ ID NO:5:

(i) SEQUENCE CHARACTERISTICS:
            (A) LENGTH: 363 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(xi) SEQUENCE DESCRIPTION: SEQ ID NO:5:

CAGATCCAGT TGGTGCAGTC TGGACCTGAG CTGAAGAAGC CTGGAGAGAC AGTCAAGATC         60

TCCTGCAAGG CTTCTGGGTA CACCTTCACA AACTATGGAA TGAACTGGGT GAAGCAGGCT        120

CCAGGAAAGG GTTTAAAGTG GATGGGCTGG ATAAACACCA GAAATGGAAA GTCAACATAT        180

GTTGATGACT TCAAGGGACG GTTTGCCTTC TCTTTGGAAA GCTCTGCCAG CACTGCCAAT        240

TTGCAGATCG ACAACCTCAA AGATGAGGAC ACGGCTACAT ATTTCTGTAC AAGAGAAGGG        300

AATATGGATG GTTACTTCCC TTTTACTTAC TGGGGCCAAG GGACTCTGGT CACTGTCTCT        360

GCA        363

(2) INFORMATION FOR SEQ ID NO:6:

(i) SEQUENCE CHARACTERISTICS:
            (A) LENGTH: 321 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(xi) SEQUENCE DESCRIPTION: SEQ ID NO:6:

CAAATTGTTC TCTCCCAGTC TCCAGCAATC CTGTCTGCAT CTCCAGGGGA GAAGGTCACA      60

ATGACTTGCA GGGCCAGCTC AAGTGTAAAT TACATGCACT GGTACCAGCA GAAGCCAGGA     120

TCCTCCCCCA AACCCTGGAT TTATGCCACA TCCAACCTGG CTTCTGGAGT CCCTGCTCGC     180

TTCAGTGGCA GTGGGTCTGG GACCTCTTAC TCTCTCACAA TCAGCAGAGT GGAGGCTGAA     240

GATGCTGCCA CTTATTACTG CCAGCAGTGG AGTATTAACC CACGGACGTT CGGTGGAGGC     300

ACCAAGCTGG AAATCAAACG G                                              321

(2) INFORMATION FOR SEQ ID NO:7:

(i) SEQUENCE CHARACTERISTICS:
            (A) LENGTH: 121 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTISENSE: NO (v) FRAGMENT TYPE: internal (vi) ORIGINAL SOURCE:

(xi) SEQUENCE DESCRIPTION: SEQ ID NO:7:

Gln Ile Gln Leu Val Gln Ser Gly Pro Glu Leu Lys Lys Pro Gly Glu
  1               5                  10                  15

Thr Val Lys Ile Ser Cys Lys Ala Ser Gly Tyr Thr Phe Thr Asn Tyr
                 20                  25                  30

Gly Met Asn Trp Val Lys Gln Ala Pro Gly Lys Gly Leu Lys Trp Met
             35                  40                  45

Gly Trp Ile Asn Thr Arg Asn Gly Lys Ser Thr Tyr Val Asp Asp Phe
     50                  55                  60

Lys Gly Arg Phe Ala Phe Ser Leu Glu Ser Ser Ala Ser Thr Ala Asn
 65                  70                  75                  80

Leu Gln Ile Asp Asn Leu Lys Asp Glu Asp Thr Ala Thr Tyr Phe Cys
                 85                  90                  95

Thr Arg Glu Gly Asn Met Asp Gly Tyr Phe Pro Phe Thr Tyr Trp Gly
            100                 105                 110

Gln Gly Thr Leu Val Thr Val Ser Ala
            115                 120

(2) INFORMATION FOR SEQ ID NO:8:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTISENSE: NO (v) FRAGMENT TYPE: internal (vi) ORIGINAL SOURCE:

(xi) SEQUENCE DESCRIPTION: SEQ ID NO:8:

Asn Tyr Gly Met Asn
1               5

(2) INFORMATION FOR SEQ ID NO:9:

(i) SEQUENCE CHARACTERISTICS:
            (A) LENGTH: 17 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTISENSE: NO (v) FRAGMENT TYPE: internal (vi) ORIGINAL SOURCE:

(xi) SEQUENCE DESCRIPTION: SEQ ID NO:9:

Trp Ile Asn Thr Arg Asn Gly Lys Ser Thr Tyr Val Asp Asp Phe Lys
1               5                   10                  15
Gly (2) INFORMATION FOR SEQ ID NO:10:

(i) SEQUENCE CHARACTERISTICS:
            (A) LENGTH: 12 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTISENSE: NO (v) FRAGMENT TYPE: internal (vi) ORIGINAL SOURCE:

(xi) SEQUENCE DESCRIPTION: SEQ ID NO:10:

Glu Gly Asn Met Asp Gly Tyr Phe Pro Phe Thr Tyr
1               5                   10

(2) INFORMATION FOR SEQ ID NO:11:

(i) SEQUENCE CHARACTERISTICS:
            (A) LENGTH: 107 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTISENSE: NO (v) FRAGMENT TYPE: internal (vi) ORIGINAL SOURCE:

(xi) SEQUENCE DESCRIPTION: SEQ ID NO:11:

```
Gln Ile Val Leu Ser Gln Ser Pro Ala Ile Leu Ser Ala Ser Pro Gly
 1               5                  10                  15

Glu Lys Val Thr Met Thr Cys Arg Ala Ser Ser Val Asn Tyr Met
                 20                  25                  30

His Trp Tyr Gln Gln Lys Pro Gly Ser Ser Pro Lys Pro Trp Ile Tyr
             35                  40                  45

Ala Thr Ser Asn Leu Ala Ser Gly Val Pro Ala Arg Phe Ser Gly Ser
         50                  55                  60

Gly Ser Gly Thr Ser Tyr Ser Leu Thr Ile Ser Arg Val Glu Ala Glu
 65                  70                  75                  80

Asp Ala Ala Thr Tyr Tyr Cys Gln Gln Trp Ser Ile Asn Pro Arg Thr
                 85                  90                  95

Phe Gly Gly Gly Thr Lys Leu Glu Ile Lys Arg
                100                 105
```

(2) INFORMATION FOR SEQ ID NO:12:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTISENSE: NO (v) FRAGMENT TYPE: internal (vi) ORIGINAL SOURCE:

(xi) SEQUENCE DESCRIPTION: SEQ ID NO:12:

```
Arg Ala Ser Ser Ser Val Asn Tyr Met His
 1               5                  10
```

(2) INFORMATION FOR SEQ ID NO:13:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTISENSE: NO (v) FRAGMENT TYPE: internal (vi) ORIGINAL SOURCE:

(xi) SEQUENCE DESCRIPTION: SEQ ID NO:13:

```
Ala Thr Ser Asn Leu Ala Ser
 1               5
```

(2) INFORMATION FOR SEQ ID NO:14:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTISENSE: NO (v) FRAGMENT TYPE: internal (vi) ORIGINAL SOURCE:

(xi) SEQUENCE DESCRIPTION: SEQ ID NO:14:

Gln Gln Trp Ser Ile Asn Pro Arg Thr
  1               5

(2) INFORMATION FOR SEQ ID NO:15:

(i) SEQUENCE CHARACTERISTICS:
           (A) LENGTH: 104 base pairs
           (B) TYPE: nucleic acid
           (C) STRANDEDNESS: single
           (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(xi) SEQUENCE DESCRIPTION: SEQ ID NO:15:

```
CAACTAGTGC AATCTGGGTC TGAGTTGAAG AAGCCTGGGG CCTCAGTGAA GGTTTCCTGC      60

AAGGCCTCTG GATACACCTT CACTAACTAT GGAATGAACT GGGT                     104
```

(2) INFORMATION FOR SEQ ID NO:16:

(i) SEQUENCE CHARACTERISTICS:
           (A) LENGTH: 108 base pairs
           (B) TYPE: nucleic acid
           (C) STRANDEDNESS: single
           (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(xi) SEQUENCE DESCRIPTION: SEQ ID NO:16:

```
TTGAAGTCAT CAACATATGT TGACTTTCCA TTTCTGGTGT TTATCCATCC CATCCACTCG      60

AGCCCTTGTC CAGGGGCCTG TCGCACCCAG TTCATTCCAT AGTTAGTG                 108
```

(2) INFORMATION FOR SEQ ID NO:17:

(i) SEQUENCE CHARACTERISTICS:
           (A) LENGTH: 107 base pairs
           (B) TYPE: nucleic acid
           (C) STRANDEDNESS: single
           (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(xi) SEQUENCE DESCRIPTION: SEQ ID NO:17:

```
GTCAACATAT GTTGATGACT TCAAGGGGCG GTTTGTCTTC CCTCTGTCAG CACGGCATAT    60
CTACAGATCA GCAGCCTAAA GGCTGACGAC ACTGCAGTGT ATTACTG                 107
```

(2) INFORMATION FOR SEQ ID NO:18:

(i) SEQUENCE CHARACTERISTICS:
        (A) LENGTH: 91 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(xi) SEQUENCE DESCRIPTION: SEQ ID NO:18:

```
GGTACCCTGG CCCCAGTAAG TAAAAGGGAA GTAACCATCC ATATTCCCTT CTCTCGCACA    60
GTAATACACT GCAGTGTCGT CAGCCTTTAG G                                   91
```

(2) INFORMATION FOR SEQ ID NO:19:

(i) SEQUENCE CHARACTERISTICS:
        (A) LENGTH: 337 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(ix) FEATURE:

(A) NAME/KEY: Coding S equence
       (B) LOCATION: 2...337
       (D) OTHER INFORMATION:

(xi) SEQUENCE DESCRIPTION: SEQ ID NO:19:

```
A CTA GTG CAA TCT GGG TCT GAG TTG AAG AAG CCT GGG GCC TCA GTG AAG     49
  Leu Val Gln Ser Gly Ser Glu Leu Lys Lys Pro Gly Ala Ser Val Lys
   1               5                  10                  15

GTT TCC TGC AAG GCC TCT GGA TAC ACC TTC ACT AAC TAT GGA ATG AAC       97
Val Ser Cys Lys Ala Ser Gly Tyr Thr Phe Thr Asn Tyr Gly Met Asn
             20                  25                  30

TGG GTG CGA CAG GCC CCT GGA CAA GGG CTC GAG TGG ATG GGA TGG ATA      145
Trp Val Arg Gln Ala Pro Gly Gln Gly Leu Glu Trp Met Gly Trp Ile
         35                  40                  45

AAC ACC AGA AAT GGA AAG TCA ACA TAT GTT GAT GAC TTC AAG GGG CGG      193
Asn Thr Arg Asn Gly Lys Ser Thr Tyr Val Asp Asp Phe Lys Gly Arg
     50                  55                  60

TTT GTC TTC TCC TTG GAC ACC TCT GTC AGC ACG GCA TAT CTA CAG ATC      241
```

```
Phe Val Phe Ser Leu Asp Thr Ser Val Ser Thr Ala Tyr Leu Gln Ile
65                  70                  75                  80

AGC AGC CTA AAG GCT GAC GAC ACT GCA GTG TAT TAC TGT GCG AGA GAA    289
Ser Ser Leu Lys Ala Asp Asp Thr Ala Val Tyr Tyr Cys Ala Arg Glu
                85                  90                  95

GGG AAT ATG GAT GGT TAC TTC CCT TTT ACT TAC TGG GGC CAG GGT ACC    337
Gly Asn Met Asp Gly Tyr Phe Pro Phe Thr Tyr Trp Gly Gln Gly Thr
            100                 105                 110
```

(2) INFORMATION FOR SEQ ID NO:20:

(i) SEQUENCE CHARACTERISTICS:
        (A) LENGTH: 112 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTISENSE: NO (v) FRAGMENT TYPE: internal (vi) ORIGINAL SOURCE:

(xi) SEQUENCE DESCRIPTION: SEQ ID NO:20:

```
Leu Val Gln Ser Gly Ser Glu Leu Lys Lys Pro Gly Ala Ser Val Lys
1               5                   10                  15

Val Ser Cys Lys Ala Ser Gly Tyr Thr Phe Thr Asn Tyr Gly Met Asn
                20                  25                  30

Trp Val Arg Gln Ala Pro Gly Gln Gly Leu Glu Trp Met Gly Trp Ile
            35                  40                  45

Asn Thr Arg Asn Gly Lys Ser Thr Tyr Val Asp Asp Phe Lys Gly Arg
        50                  55                  60

Phe Val Phe Ser Leu Asp Thr Ser Val Ser Thr Ala Tyr Leu Gln Ile
65                  70                  75                  80

Ser Ser Leu Lys Ala Asp Asp Thr Ala Val Tyr Tyr Cys Ala Arg Glu
                85                  90                  95

Gly Asn Met Asp Gly Tyr Phe Pro Phe Thr Tyr Trp Gly Gln Gly Thr
            100                 105                 110
```

(2) INFORMATION FOR SEQ ID NO:21:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(xi) SEQUENCE DESCRIPTION: SEQ ID NO:21:

GCTACTAGTG CAATCTGGGT CTGAGTTGAA GCC                              33

(2) INFORMATION FOR SEQ ID NO:22:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(xi) SEQUENCE DESCRIPTION: SEQ ID NO:22:

TGGGTACCCT GGCCCCAGTA AGTAAAAGGG                                            30

(2) INFORMATION FOR SEQ ID NO:23:

(i) SEQUENCE CHARACTERISTICS:
        (A) LENGTH: 97 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(ix) FEATURE:

(A) NAME/KEY: Coding Sequence
        (B) LOCATION: 27...95
        (D) OTHER INFORMATION:

(xi) SEQUENCE DESCRIPTION: SEQ ID NO:23:

GAATTCTGAG CACACAGGAC CTCACC ATG GGA TGG AGC T GT ATC ATC CTC TTC           53
                            Met Gly Trp Se r Cys Ile Ile Leu Phe
                              1               5

TTG GTA GCA ACA GCT ACA GGT GTC CAC TCC CAG GTC CAA CTA GT                  97
Leu Val Ala Thr Ala Thr Gly Val His Ser Gln Val Gln Leu
 10              15                  20

(2) INFORMATION FOR SEQ ID NO:24:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTISENSE: NO (v) FRAGMENT TYPE: internal (vi) ORIGINAL SOURCE:

(xi) SEQUENCE DESCRIPTION: SEQ ID NO:24:

Met Gly Trp Ser Cys Ile Ile Leu Phe Leu Val Ala Thr Ala Thr Gly
  1               5                  10                  15

```
Val His Ser Gln Val Gln Leu
            20

(2) INFORMATION FOR SEQ ID NO:25:

(i) SEQUENCE CHARACTERISTICS:
        (A) LENGTH: 110 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(xi) SEQUENCE DESCRIPTION: SEQ ID NO:25:

GGAGACGCCA TCGAATTCTG AGCACACAGG ACCTCACCAT GGGATGGAGC TGTATCATCC            60

TCTTCTTGGT AGCAACAGCT ACAGGTGTCC ACTCCCAGGT CCAACTGCAG                     110

(2) INFORMATION FOR SEQ ID NO:26:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(xi) SEQUENCE DESCRIPTION: SEQ ID NO:26:

GGAGACGCCA TCGAATTCTG A                                                     21

(2) INFORMATION FOR SEQ ID NO:27:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(xi) SEQUENCE DESCRIPTION: SEQ ID NO:27:

GATTGCACTA GTTGGACCTG GGAGTGGACA                                            30

(2) INFORMATION FOR SEQ ID NO:28:

(i) SEQUENCE CHARACTERISTICS:
        (A) LENGTH: 77 base pairs
```

(B) TYPE: nucleic acid
            (C) STRANDEDNESS: single
            (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(xi) SEQUENCE DESCRIPTION: SEQ ID NO:28:

CTAGAGTGGG TCGCAGAGAT CTCTGATGGT GGTAGTTACA CCTACTATCC AGACACTGTG    60

ACGGGCCGGT TCACGAT    77

(2) INFORMATION FOR SEQ ID NO:29:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(xi) SEQUENCE DESCRIPTION: SEQ ID NO:29:

ATCGTGAACC GGCCCGTCAC AGTGTCTGGA TAGTAGGTGT AACTACCACC ATCAGAGATC    60

TCTGCGACCC ACT    73

(2) INFORMATION FOR SEQ ID NO:30:

(i) SEQUENCE CHARACTERISTICS:
        (A) LENGTH: 363 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(ix) FEATURE:

(A) NAME/KEY: Coding S equence
        (B) LOCATION: 1...363
        (D) OTHER INFORMATION: F9HZHC 1-0

(xi) SEQUENCE DESCRIPTION: SEQ ID NO:30:

```
CAG GTG CAA CTA GTG CAA TCT GGG TCT GAG TTG AAG AAG CCT GGG GCC    48
Gln Val Gln Leu Val Gln Ser Gly Ser Glu Leu Lys Lys Pro Gly Ala
 1               5                  10                  15

TCA GTG AAG GTT TCC TGC AAG GCC TCT GGA TAC ACC TTC ACT AAC TAT    96
Ser Val Lys Val Ser Cys Lys Ala Ser Gly Tyr Thr Phe Thr Asn Tyr
             20                  25                  30
```

```
GGA ATG AAC TGG GTG CGA CAG GCC CCT GGA CAA GGG CTC GAG TGG ATG      144
Gly Met Asn Trp Val Arg Gln Ala Pro Gly Gln Gly Leu Glu Trp Met
        35                  40                  45

GGA TGG ATA AAC ACC AGA AAT GGA AAG TCA ACA TAT GTT GAT GAC TTC      192
Gly Trp Ile Asn Thr Arg Asn Gly Lys Ser Thr Tyr Val Asp Asp Phe
 50                  55                  60

AAG GGA CGG TTT GTC TTC TCC TTG GAC ACC TCT GTC AGC ACG GCA TAT      240
Lys Gly Arg Phe Val Phe Ser Leu Asp Thr Ser Val Ser Thr Ala Tyr
 65              70                  75                  80

CTA CAG ATC AGC AGC CTA AAG GCT GAC GAC ACT GCA GTG TAT TAC TGT      288
Leu Gln Ile Ser Ser Leu Lys Ala Asp Asp Thr Ala Val Tyr Tyr Cys
                 85                  90                  95

GCG AGA GAA GGG AAT ATG GAT GGT TAC TTC CCT TTT ACT TAC TGG GGC      336
Ala Arg Glu Gly Asn Met Asp Gly Tyr Phe Pro Phe Thr Tyr Trp Gly
            100                 105                 110

CAG GGT ACC CTG GTC ACC GTC TCC TCA                                   363
Gln Gly Thr Leu Val Thr Val Ser Ser
            115                 120
```

(2) INFORMATION FOR SEQ ID NO:31:

(i) SEQUENCE CHARACTERISTICS:
        (A) LENGTH: 121 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTISENSE: NO (v) FRAGMENT TYPE: internal (vi) ORIGINAL SOURCE:

(xi) SEQUENCE DESCRIPTION: SEQ ID NO:31:

```
Gln Val Gln Leu Val Gln Ser Gly Ser Glu Leu Lys Lys Pro Gly Ala
 1               5                  10                  15

Ser Val Lys Val Ser Cys Lys Ala Ser Gly Tyr Thr Phe Thr Asn Tyr
                 20                  25                  30

Gly Met Asn Trp Val Arg Gln Ala Pro Gly Gln Gly Leu Glu Trp Met
            35                  40                  45

Gly Trp Ile Asn Thr Arg Asn Gly Lys Ser Thr Tyr Val Asp Asp Phe
 50                  55                  60

Lys Gly Arg Phe Val Phe Ser Leu Asp Thr Ser Val Ser Thr Ala Tyr
 65              70                  75                  80

Leu Gln Ile Ser Ser Leu Lys Ala Asp Asp Thr Ala Val Tyr Tyr Cys
                 85                  90                  95

Ala Arg Glu Gly Asn Met Asp Gly Tyr Phe Pro Phe Thr Tyr Trp Gly
            100                 105                 110

Gln Gly Thr Leu Val Thr Val Ser Ser
            115                 120
```

(2) INFORMATION FOR SEQ ID NO:32:

(i) SEQUENCE CHARACTERISTICS:
        (A) LENGTH: 165 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(xi) SEQUENCE DESCRIPTION: SEQ ID NO:32:

```
AGTACTGACA CAGTCTCCAG CCACCCTGTC TTTGTCTCCA GGGGAAAGAG CCACCCTCTC      60

CTGCAGGGCC AGCTCAAGTG TAAATTACAT GCACTGGTAC CAACAGAGAC CTGGCCAGGC     120

TCCCAGGCTC CTCATCTATG CCACTAGTAA CCTGGCTTCT GGCAT                     165
```

(2) INFORMATION FOR SEQ ID NO:33:

(i) SEQUENCE CHARACTERISTICS:
        (A) LENGTH: 146 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(xi) SEQUENCE DESCRIPTION: SEQ ID NO:33:

```
CCGCGGGTTA ATACTCCACT GCTGACAGTA ATAAACCGCA AAATCTTCAG GCTCTAGACT      60

GCTGATGGTG AGAGTGAAAT CTGTCCCAGA CCCGGATCCA CTGAACCTGG CTGGGATGCC     120

AGAAGCCAGG TTACTAGTGG CATAGA                                          146
```

(2) INFORMATION FOR SEQ ID NO:34:

(i) SEQUENCE CHARACTERISTICS:
        (A) LENGTH: 280 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(ix) FEATURE:

(A) NAME/KEY: Coding S equence
        (B) LOCATION: 2...280
        (D) OTHER INFORMATION:

(xi) SEQUENCE DESCRIPTION: SEQ ID NO:34:

```
A GTA CTG ACA CAG TCT CCA GCC ACC CTG TCT TTG TCT CCA GGG GAA AGA      49
  Val Leu Thr Gln Ser Pro Ala Thr Leu  Ser Leu Ser Pro Gly Glu Arg
   1               5                  10                  15

GCC ACC CTC TCC TGC AGG GCC AGC TCA AGT GTA AAT TAC ATG CAC TGG        97
Ala Thr Leu Ser Cys Arg Ala Ser Ser Ser Val Asn Tyr Met His Trp
         20                  25                  30
```

```
TAC CAA CAG AGA CCT GGC CAG GCT CCC AGG CTC CTC ATC TAT GCC ACT    145
Tyr Gln Gln Arg Pro Gly Gln Ala Pro Arg Leu Leu Ile Tyr Ala Thr
         35                  40                  45

AGT AAC CTG GCT TCT GGC ATC CCA GCC AGG TTC AGT GGA TCC GGG TCT    193
Ser Asn Leu Ala Ser Gly Ile Pro Ala Arg Phe Ser Gly Ser Gly Ser
 50                  55                  60

GGG ACA GAT TTC ACT CTC ACC ATC AGC AGT CTA GAG CCT GAA GAT TTT    241
Gly Thr Asp Phe Thr Leu Thr Ile Ser Ser Leu Glu Pro Glu Asp Phe
65                  70                  75                  80

GCG GTT TAT TAC TGT CAG CAG TGG AGT ATT AAC CCG CGG                280
Ala Val Tyr Tyr Cys Gln Gln Trp Ser Ile Asn Pro Arg
             85                  90
```

(2) INFORMATION FOR SEQ ID NO:35:

(i) SEQUENCE CHARACTERISTICS:
        (A) LENGTH: 93 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTISENSE: NO (v) FRAGMENT TYPE: internal (vi) ORIGINAL SOURCE:

(xi) SEQUENCE DESCRIPTION: SEQ ID NO:35:

```
Val Leu Thr Gln Ser Pro Ala Thr Leu Ser Leu Ser Pro Gly Glu Arg
 1               5                  10                  15

Ala Thr Leu Ser Cys Arg Ala Ser Ser Val Asn Tyr Met His Trp
                 20                  25                  30

Tyr Gln Gln Arg Pro Gly Gln Ala Pro Arg Leu Leu Ile Tyr Ala Thr
             35                  40                  45

Ser Asn Leu Ala Ser Gly Ile Pro Ala Arg Phe Ser Gly Ser Gly Ser
 50                  55                  60

Gly Thr Asp Phe Thr Leu Thr Ile Ser Ser Leu Glu Pro Glu Asp Phe
65                  70                  75                  80

Ala Val Tyr Tyr Cys Gln Gln Trp Ser Ile Asn Pro Arg
             85                  90
```

(2) INFORMATION FOR SEQ ID NO:36:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(xi) SEQUENCE DESCRIPTION: SEQ ID NO:36:

TCGAGTACTG ACACAGTCTC CAGCCAC                                      27

```
(2) INFORMATION FOR SEQ ID NO:37:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(xi) SEQUENCE DESCRIPTION: SEQ ID NO:37:

GACCGCGGGT TAATACTCCA CTGCTGA                                        27

(2) INFORMATION FOR SEQ ID NO:38:

(i) SEQUENCE CHARACTERISTICS:
        (A) LENGTH: 94 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(ix) FEATURE:

(A) NAME/KEY: Coding S equence
        (B) LOCATION: 27...92
        (D) OTHER INFORMATION:

(xi) SEQUENCE DESCRIPTION: SEQ ID NO:38:

GAATTCTGAG CACACAGGAC CTCACC ATG GGA TGG AGC T GT ATC ATC CTC TTC    53
                            Met Gly Trp Se r Cys Ile Ile Leu Phe
                             1               5

TTG GTA GCA ACA GCT ACA GGT GTC CAC TCC GAG ATA GTA CT               94
Leu Val Ala Thr Ala Thr Gly Val His Ser Glu Ile Val
10                  15                  20

(2) INFORMATION FOR SEQ ID NO:39:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTISENSE: NO (v) FRAGMENT TYPE: internal (vi) ORIGINAL SOURCE:

(xi) SEQUENCE DESCRIPTION: SEQ ID NO:39:

Met Gly Trp Ser Cys Ile Ile Leu Phe Leu Val Ala Thr Ala Thr Gly
```

```
        1               5              10              15
Val His Ser Glu Ile Val
            20
```

(2) INFORMATION FOR SEQ ID NO:40:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(xi) SEQUENCE DESCRIPTION: SEQ ID NO:40:

```
GACTGTGTCA GTACTATCTC GGAGTGGACA                                     30
```

(2) INFORMATION FOR SEQ ID NO:41:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(xi) SEQUENCE DESCRIPTION: SEQ ID NO:41:

```
GGGCAGCCTC CTAAGTTGCT CATTTACTGG GCGTCGACTA GGGAATCTGG GGTAC          55
```

(2) INFORMATION FOR SEQ ID NO:42:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(xi) SEQUENCE DESCRIPTION: SEQ ID NO:42:

```
CCCAGATTCC CTAGTCGACG CCCAGTAAAT GAGCAACTTA GGAGGCTGCC C              51
```

(2) INFORMATION FOR SEQ ID NO:43:

(i) SEQUENCE CHARACTERISTICS:
        (A) LENGTH: 321 base pairs (B) TYPE: nucleic acid
        (C) STRANDEDNESS: single
        (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(ix) FEATURE:

(A) NAME/KEY: Coding S equence
        (B) LOCATION: 1...321
        (D) OTHER INFORMATION: F9HZLC1-0

(xi) SEQUENCE DESCRIPTION: SEQ ID NO:43:

```
GAA ATA GTA CTG ACA CAG TCT CCA GCC ACC CTG TCT TTG TCT CCA GGG        48
Glu Ile Val Leu Thr Gln Ser Pro Ala Thr Leu Ser Leu Ser Pro Gly
 1               5                  10                  15

GAA AGA GCC ACC CTC TCC TGC AGG GCC AGC TCA AGT GTA AAT TAC ATG        96
Glu Arg Ala Thr Leu Ser Cys Arg Ala Ser Ser Ser Val Asn Tyr Met
                20                  25                  30

CAC TGG TAC CAA CAG AGA CCT GGC CAG GCT CCC AGG CTC CTC ATC TAT       144
His Trp Tyr Gln Gln Arg Pro Gly Gln Ala Pro Arg Leu Leu Ile Tyr
         35                  40                  45

GCC ACT AGT AAC CTG GCT TCT GGC ATC CCA GCC AGG TTC AGT GGA TCC       192
Ala Thr Ser Asn Leu Ala Ser Gly Ile Pro Ala Arg Phe Ser Gly Ser
 50                  55                  60

GGG TCT GGG ACA GAT TTC ACT CTC ACC ATC AGC AGT CTA GAG CCT GAA       240
Gly Ser Gly Thr Asp Phe Thr Leu Thr Ile Ser Ser Leu Glu Pro Glu
 65                  70                  75                  80

GAT TTT GCG GTT TAT TAC TGT CAG CAG TGG AGT ATT AAC CCG CGG ACG       288
Asp Phe Ala Val Tyr Tyr Cys Gln Gln Trp Ser Ile Asn Pro Arg Thr
                 85                  90                  95

TTC GGC GGA GGG ACC AAG GTG GAG ATC AAA CGA                           321
Phe Gly Gly Gly Thr Lys Val Glu Ile Lys Arg
                100                 105
```

(2) INFORMATION FOR SEQ ID NO:44:

(i) SEQUENCE CHARACTERISTICS:
        (A) LENGTH: 107 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTISENSE: NO (v) FRAGMENT TYPE: internal (vi) ORIGINAL SOURCE:

(xi) SEQUENCE DESCRIPTION: SEQ ID NO:44:

```
Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Ser Ser Val Asn Tyr Met
                20                  25                  30

His Trp Tyr Gln Gln Arg Pro Gly Gln Ala Pro Arg Leu Leu Ile Tyr
         35                  40                  45
```

```
Ala Thr Ser Asn Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Trp Ser Ile Asn Pro Arg Thr
                85                  90                  95

Phe Gly Gly Gly Thr Lys Val Glu Ile Lys Arg
            100                 105
```

(2) INFORMATION FOR SEQ ID NO:45:

(i) SEQUENCE CHARACTERISTICS:
        (A) LENGTH: 134 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(xi) SEQUENCE DESCRIPTION: SEQ ID NO:45:

```
CCTGGACAAG GGCTCAAGTG GATGGGATGG ATAAACACCA GAAATGGAAA GTCAACATAT      60

GTTGATGACT TCAAGGGACG GTTTGTCTTC TCTCTAGACT CCTCTGTCAG CACGGCATAT     120

CTACAGATCA GCAG                                                      134
```

(2) INFORMATION FOR SEQ ID NO:46:

(i) SEQUENCE CHARACTERISTICS:
        (A) LENGTH: 134 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(xi) SEQUENCE DESCRIPTION: SEQ ID NO:46:

```
GGTACCCTGG CCCCAGTAAG TAAAAGGGAA GTAACCATCC ATATTCCCTT CTCTCGTACA      60

GTAATACACT GCAGTGTCGT CAGCCTTTAG GCTGCTGATC TGTAGATATG CCGTGCTGAC     120

AGAGGAGTCT AGAG                                                      134
```

(2) INFORMATION FOR SEQ ID NO:47:

(i) SEQUENCE CHARACTERISTICS:
        (A) LENGTH: 225 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(ix) FEATURE:

(A) NAME/KEY: Coding S equence
    (B) LOCATION: 1...225
    (D) OTHER INFORMATION:

(xi) SEQUENCE DESCRIPTION: SEQ ID NO:47:

```
CCT GGA CAA GGG CTC AAG TGG ATG GGA TGG ATA AAC ACC AGA AAT GGA      48
Pro Gly Gln Gly Leu Lys Trp Met Gly Trp Ile Asn Thr Arg Asn Gly
 1               5                  10                  15

AAG TCA ACA TAT GTT GAT GAC TTC AAG GGA CGG TTT GTC TTC TCT CTA      96
Lys Ser Thr Tyr Val Asp Asp Phe Lys Gly Arg Phe Val Phe Ser Leu
            20                  25                  30

GAC TCC TCT GTC AGC ACG GCA TAT CTA CAG ATC AGC AGC CTA AAG GCT     144
Asp Ser Ser Val Ser Thr Ala Tyr Leu Gln Ile Ser Ser Leu Lys Ala
        35                  40                  45

GAC GAC ACT GCA GTG TAT TAC TGT ACG AGA GAA GGG AAT ATG GAT GGT     192
Asp Asp Thr Ala Val Tyr Tyr Cys Thr Arg Glu Gly Asn Met Asp Gly
 50                  55                  60

TAC TTC CCT TTT ACT TAC TGG GGC CAG GGT ACC                         225
Tyr Phe Pro Phe Thr Tyr Trp Gly Gln Gly Thr
 65                  70                  75
```

(2) INFORMATION FOR SEQ ID NO:48:

(i) SEQUENCE CHARACTERISTICS:
        (A) LENGTH: 75 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTISENSE: NO (v) FRAGMENT TYPE: internal (vi) ORIGINAL SOURCE:

(xi) SEQUENCE DESCRIPTION: SEQ ID NO:48:

```
Pro Gly Gln Gly Leu Lys Trp Met Gly Trp Ile Asn Thr Arg Asn Gly
 1               5                  10                  15

Lys Ser Thr Tyr Val Asp Asp Phe Lys Gly Arg Phe Val Phe Ser Leu
            20                  25                  30

Asp Ser Ser Val Ser Thr Ala Tyr Leu Gln Ile Ser Ser Leu Lys Ala
        35                  40                  45

Asp Asp Thr Ala Val Tyr Tyr Cys Thr Arg Glu Gly Asn Met Asp Gly
 50                  55                  60

Tyr Phe Pro Phe Thr Tyr Trp Gly Gln Gly Thr
 65                  70                  75
```

(2) INFORMATION FOR SEQ ID NO:49:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(xi) SEQUENCE DESCRIPTION: SEQ ID NO:49:

TTTCCTGGAC AAGGGCTCAA GTGGATG                                             27

(2) INFORMATION FOR SEQ ID NO:50:

(i) SEQUENCE CHARACTERISTICS:
             (A) LENGTH: 24 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(xi) SEQUENCE DESCRIPTION: SEQ ID NO:50:

TTTGGTACCC TGGCCCCAGT AAGT                                                24

(2) INFORMATION FOR SEQ ID NO:51:

(i) SEQUENCE CHARACTERISTICS:
             (A) LENGTH: 363 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(ix) FEATURE:

(A) NAME/KEY: Coding S equence
             (B) LOCATION: 1...363
             (D) OTHER INFORMATION: F9HZHC 1-1

(xi) SEQUENCE DESCRIPTION: SEQ ID NO:51:

CAG GTG CAA CTA GTG CAA TCT GGG TCT GAG TTG AAG AAG CCT GGG GCC            48
Gln Val Gln Leu Val Gln Ser Gly Ser Glu Leu Lys Lys Pro Gly Ala
 1               5                  10                  15

TCA GTG AAG GTT TCC TGC AAG GCC TCT GGA TAC ACC TTC ACT AAC TAT            96
Ser Val Lys Val Ser Cys Lys Ala Ser Gly Tyr Thr Phe Thr Asn Tyr
             20                  25                  30

GGA ATG AAC TGG GTG CGA CAG GCC CCT GGA CAA GGG CTC AAG TGG ATG           144
Gly Met Asn Trp Val Arg Gln Ala Pro Gly Gln Gly Leu Lys Trp Met
         35                  40                  45

GGA TGG ATA AAC ACC AGA AAT GGA AAG TCA ACA TAT GTT GAT GAC TTC           192
Gly Trp Ile Asn Thr Arg Asn Gly Lys Ser Thr Tyr Val Asp Asp Phe

```
            50                      55                      60
AAG GGA CGG TTT GTC TTC TCT CTA GAC TCC TCT GTC AGC ACG GCA TAT    240
Lys Gly Arg Phe Val Phe Ser Leu Asp Ser Ser Val Ser Thr Ala Tyr
 65                      70                      75                      80

CTA CAG ATC AGC AGC CTA AAG GCT GAC GAC ACT GCA GTG TAT TAC TGT    288
Leu Gln Ile Ser Ser Leu Lys Ala Asp Asp Thr Ala Val Tyr Tyr Cys
                         85                      90                      95

ACG AGA GAA GGG AAT ATG GAT GGT TAC TTC CCT TTT ACT TAC TGG GGC    336
Thr Arg Glu Gly Asn Met Asp Gly Tyr Phe Pro Phe Thr Tyr Trp Gly
                        100                     105                     110

CAG GGT ACC CTG GTC ACC GTC TCC TCA                                363
Gln Gly Thr Leu Val Thr Val Ser Ser
                        115                     120
```

(2) INFORMATION FOR SEQ ID NO:52:

(i) SEQUENCE CHARACTERISTICS:
        (A) LENGTH: 121 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTISENSE: NO (v) FRAGMENT TYPE: internal (vi) ORIGINAL SOURCE:

(xi) SEQUENCE DESCRIPTION: SEQ ID NO:52:

```
Gln Val Gln Leu Val Gln Ser Gly Ser Glu Leu Lys Lys Pro Gly Ala
 1               5                  10                  15

Ser Val Lys Val Ser Cys Lys Ala Ser Gly Tyr Thr Phe Thr Asn Tyr
                20                  25                  30

Gly Met Asn Trp Val Arg Gln Ala Pro Gly Gln Gly Leu Lys Trp Met
            35                  40                  45

Gly Trp Ile Asn Thr Arg Asn Gly Lys Ser Thr Tyr Val Asp Asp Phe
        50                  55                  60

Lys Gly Arg Phe Val Phe Ser Leu Asp Ser Ser Val Ser Thr Ala Tyr
 65                  70                  75                  80

Leu Gln Ile Ser Ser Leu Lys Ala Asp Asp Thr Ala Val Tyr Tyr Cys
                85                  90                  95

Thr Arg Glu Gly Asn Met Asp Gly Tyr Phe Pro Phe Thr Tyr Trp Gly
            100                 105                 110

Gln Gly Thr Leu Val Thr Val Ser Ser
        115                 120
```

(2) INFORMATION FOR SEQ ID NO:53:

(i) SEQUENCE CHARACTERISTICS:
        (A) LENGTH: 82 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(xi) SEQUENCE DESCRIPTION: SEQ ID NO:53:

CAACAGAGAC CTGGCCAGGC TCCCAAGCCC TGGATCTATG CCACGAGTAA CCTGGCTAGC    60

GGCGTCCCAG CCAGGTTCAG TG    82

(2) INFORMATION FOR SEQ ID NO:54:

(i) SEQUENCE CHARACTERISTICS:
        (A) LENGTH: 90 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(xi) SEQUENCE DESCRIPTION: SEQ ID NO:54:

GATCCACTGA ACCTGGCTGG GACGCCGCTA GCCAGGTTAC TCGTGGCATA GATCCAGGGC    60

TTGGGAGCCT GGCCAGGTCT CTGTTGGTAC    90

(2) INFORMATION FOR SEQ ID NO:55:

(i) SEQUENCE CHARACTERISTICS:
        (A) LENGTH: 27 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTISENSE: NO (v) FRAGMENT TYPE: internal (vi) ORIGINAL SOURCE:

(xi) SEQUENCE DESCRIPTION: SEQ ID NO:55:

Gln Gln Arg Pro Gly Gln Ala Pro Lys Pro Trp Ile Tyr Ala Thr Ser
 1               5                  10                  15

Asn Leu Ala Ser Gly Val Pro Ala Arg Phe Ser
            20                  25

(2) INFORMATION FOR SEQ ID NO:56:

(i) SEQUENCE CHARACTERISTICS:
        (A) LENGTH: 321 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(ix) FEATURE:
  (A) NAME/KEY: Coding Sequence
  (B) LOCATION: 1...321
  (D) OTHER INFORMATION: F9HZLC 1-1

(xi) SEQUENCE DESCRIPTION: SEQ ID NO:56:

```
GAA ATA GTA CTG ACA CAG TCT CCA GCC ACC CTG TCT TTG TCT CCA GGG         48
Glu Ile Val Leu Thr Gln Ser Pro Ala Thr Leu Ser Leu Ser Pro Gly
1               5                   10                  15

GAA AGA GCC ACC CTC TCC TGC AGG GCC AGC TCA AGT GTA AAT TAC ATG         96
Glu Arg Ala Thr Leu Ser Cys Arg Ala Ser Ser Ser Val Asn Tyr Met
                20                  25                  30

CAC TGG TAC CAA CAG AGA CCT GGC CAG GCT CCC AAG CCC TGG ATC TAT        144
His Trp Tyr Gln Gln Arg Pro Gly Gln Ala Pro Lys Pro Trp Ile Tyr
            35                  40                  45

GCC ACG AGT AAC CTG GCT AGC GGC GTC CCA GCC AGG TTC AGT GGA TCC        192
Ala Thr Ser Asn Leu Ala Ser Gly Val Pro Ala Arg Phe Ser Gly Ser
50                  55                  60

GGG TCT GGG ACA GAT TTC ACT CTC ACC ATC AGC AGT CTA GAG CCT GAA        240
Gly Ser Gly Thr Asp Phe Thr Leu Thr Ile Ser Ser Leu Glu Pro Glu
65                  70                  75                  80

GAT TTT GCG GTT TAT TAC TGT CAG CAG TGG AGT ATT AAC CCG CGG ACG        288
Asp Phe Ala Val Tyr Tyr Cys Gln Gln Trp Ser Ile Asn Pro Arg Thr
                85                  90                  95

TTC GGC GGA GGG ACC AAG GTG GAG ATC AAA CGA                            321
Phe Gly Gly Gly Thr Lys Val Glu Ile Lys Arg
                100                 105
```

(2) INFORMATION FOR SEQ ID NO:57:

(i) SEQUENCE CHARACTERISTICS:
    (A) LENGTH: 107 amino acids
    (B) TYPE: amino acid
    (C) STRANDEDNESS: single
    (D) TOPOLOGY: linear (ii) MOLECULE TYPE: protein (iii) HYPOTHETICAL: NO (iv) ANTISENSE: NO (v) FRAGMENT TYPE: internal (vi) ORIGINAL SOURCE:

(xi) SEQUENCE DESCRIPTION: SEQ ID NO:57:

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Asn Tyr Met
                20                  25                  30

His Trp Tyr Gln Gln Arg Pro Gly Gln Ala Pro Lys Pro Trp Ile Tyr
            35                  40                  45

Ala Thr Ser Asn Leu Ala Ser Gly Val Pro Ala Arg Phe Ser Gly Ser
50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Trp Ser Ile Asn Pro Arg Thr
                85                  90                  95

Phe Gly Gly Gly Thr Lys Val Glu Ile Lys Arg
                100                 105
```

(2) INFORMATION FOR SEQ ID NO:58:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(xi) SEQUENCE DESCRIPTION: SEQ ID NO:58:

GATCCGGGTC TGGGACAGAT TACACTCTCA CGATATCCAG T          41

(2) INFORMATION FOR SEQ ID NO:59:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(xi) SEQUENCE DESCRIPTION: SEQ ID NO:59:

CTAGACTGGA TATCGTGAGA GTGTAATCTG TCCCAGACCC G          41

(2) INFORMATION FOR SEQ ID NO:60:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTISENSE: NO (v) FRAGMENT TYPE: internal (vi) ORIGINAL SOURCE:

(xi) SEQUENCE DESCRIPTION: SEQ ID NO:60:

Ser Gly Ser Gly Thr Asp Tyr Thr Leu Thr Ile Ser Ser
  1             5                 10

(2) INFORMATION FOR SEQ ID NO:61:

(i) SEQUENCE CHARACTERISTICS:
        (A) LENGTH: 321 base pairs
        (B) TYPE: nucleic acid
        (C) STRANDEDNESS: single
        (D) TOPOLOGY: linear

```
   (ii) MOLECULE TYPE: cDNA (iii) HYPOTHETICAL: NO (iv) ANTISENSE: NO (v) FRAGMENT TYPE:

(vi) ORIGINAL SOURCE:

(ix) FEATURE:

(A) NAME/KEY: Coding S equence
        (B) LOCATION: 1...321
        (D) OTHER INFORMATION: F9HZLC 1-2

(xi) SEQUENCE DESCRIPTION: SEQ ID NO:61:

GAA ATA GTA CTG ACA CAG TCT CCA GCC ACC CTG TCT TTG TCT CCA GGG      48
Glu Ile Val Leu Thr Gln Ser Pro Ala Thr Leu Ser Leu Ser Pro Gly
  1               5                  10                  15

GAA AGA GCC ACC CTC TCC TGC AGG GCC AGC TCA AGT GTA AAT TAC ATG      96
Glu Arg Ala Thr Leu Ser Cys Arg Ala Ser Ser Ser Val Asn Tyr Met
                 20                  25                  30

CAC TGG TAC CAA CAG AGA CCT GGC CAG GCT CCC AAG CCC TGG ATC TAT     144
His Trp Tyr Gln Gln Arg Pro Gly Gln Ala Pro Lys Pro Trp Ile Tyr
             35                  40                  45

GCC ACG AGT AAC CTG GCT AGC GGC GTC CCA GCC AGG TTC AGT GGA TCC     192
Ala Thr Ser Asn Leu Ala Ser Gly Val Pro Ala Arg Phe Ser Gly Ser
 50                  55                  60

GGG TCT GGG ACA GAT TAC ACT CTC ACG ATA TCC AGT CTA GAG CCT GAA     240
Gly Ser Gly Thr Asp Tyr Thr Leu Thr Ile Ser Ser Leu Glu Pro Glu
 65                  70                  75                  80

GAT TTT GCG GTT TAT TAC TGT CAG CAG TGG AGT ATT AAC CCG CGG ACG     288
Asp Phe Ala Val Tyr Tyr Cys Gln Gln Trp Ser Ile Asn Pro Arg Thr
                 85                  90                  95

TTC GGC GGA GGG ACC AAG GTG GAG ATC AAA CGA                         321
Phe Gly Gly Gly Thr Lys Val Glu Ile Lys Arg
                100                 105

(2) INFORMATION FOR SEQ ID NO:62:

(i) SEQUENCE CHARACTERISTICS:
        (A) LENGTH: 107 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTISENSE: NO (v) FRAGMENT TYPE: internal (vi) ORIGINAL SOURCE:

(xi) SEQUENCE DESCRIPTION: SEQ ID NO:62:

Glu Ile Val Leu Thr Gln Ser Pro Ala Thr Leu Ser Leu Ser Pro Gly
  1               5                  10                  15

Glu Arg Ala Thr Leu Ser Cys Arg Ala Ser Ser Ser Val Asn Tyr Met
                 20                  25                  30

His Trp Tyr Gln Gln Arg Pro Gly Gln Ala Pro Lys Pro Trp Ile Tyr
             35                  40                  45

Ala Thr Ser Asn Leu Ala Ser Gly Val Pro Ala Arg Phe Ser Gly Ser
 50                  55                  60
```

```
Gly Ser Gly Thr Asp Tyr Thr Leu Thr Ile Ser Ser Leu Glu Pro Glu
 65                  70                  75                  80

Asp Phe Ala Val Tyr Tyr Cys Gln Gln Trp Ser Ile Asn Pro Arg Thr
                 85                  90                  95

Phe Gly Gly Gly Thr Lys Val Glu Ile Lys Arg
            100                 105
```

(2) INFORMATION FOR SEQ ID NO:63:

(i) SEQUENCE CHARACTERISTICS:
        (A) LENGTH: 165 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(xi) SEQUENCE DESCRIPTION: SEQ ID NO:63:

```
AGTACTCACC CAGAGCCCAA GCAGCCTGAG CGCCAGCGTG GGTGACAGAG TGACCATCAC      60

CTGCAGGGCC AGCTCAAGTG TAAATTACAT GCACTGGTAC CAGCAGAAGC CAGGTAAGGC     120

TCCAAAGCCT TGGATCTACG CCACTAGTAA CCTGGCTTCT GGTGT                    165
```

(2) INFORMATION FOR SEQ ID NO:64:

(i) SEQUENCE CHARACTERISTICS:
        (A) LENGTH: 161 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(xi) SEQUENCE DESCRIPTION: SEQ ID NO:64:

```
CCGCGGGTTA ATACTCCACT GCTGGCAGTA GTAGGTGGCG ATATCCTCTG GCTGGAGGCT      60

GCTGATGGTG AAGGTGTAGT CTGTACCGCT ACCGGATCCG CTGAATCTGC TTGGCACACC     120

AGAAGCCAGG TTACTAGTGG CGTAGATCCA AGGCTTTGGA G                        161
```

(2) INFORMATION FOR SEQ ID NO:65:

(i) SEQUENCE CHARACTERISTICS:
        (A) LENGTH: 280 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(ix) FEATURE:
        (A) NAME/KEY: Coding Sequence
        (B) LOCATION: 2...280
        (D) OTHER INFORMATION:

(xi) SEQUENCE DESCRIPTION: SEQ ID NO:65:

```
A GTA CTC ACC CAG AGC CCA AGC AGC CTG AGC GCC AGC GTG GGT GAC AGA        49
  Val Leu Thr Gln Ser Pro Ser Ser Leu Ser Ala Ser Val Gly Asp Arg
   1               5                  10                  15

GTG ACC ATC ACC TGC AGG GCC AGC TCA AGT GTA AAT TAC ATG CAC TGG          97
Val Thr Ile Thr Cys Arg Ala Ser Ser Ser Val Asn Tyr Met His Trp
             20                  25                  30

TAC CAG CAG AAG CCA GGT AAG GCT CCA AAG CCT TGG ATC TAC GCC ACT         145
Tyr Gln Gln Lys Pro Gly Lys Ala Pro Lys Pro Trp Ile Tyr Ala Thr
         35                  40                  45

AGT AAC CTG GCT TCT GGT GTG CCA AGC AGA TTC AGC GGA TCC GGT AGC         193
Ser Asn Leu Ala Ser Gly Val Pro Ser Arg Phe Ser Gly Ser Gly Ser
     50                  55                  60

GGT ACA GAC TAC ACC TTC ACC ATC AGC AGC CTC CAG CCA GAG GAT ATC         241
Gly Thr Asp Tyr Thr Phe Thr Ile Ser Ser Leu Gln Pro Glu Asp Ile
 65                  70                  75                  80

GCC ACC TAC TAC TGC CAG CAG TGG AGT ATT AAC CCG CGG                     280
Ala Thr Tyr Tyr Cys Gln Gln Trp Ser Ile Asn Pro Arg
                 85                  90
```

(2) INFORMATION FOR SEQ ID NO:66:

(i) SEQUENCE CHARACTERISTICS:
        (A) LENGTH: 93 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTISENSE: NO (v) FRAGMENT TYPE: internal (vi) ORIGINAL SOURCE:

(xi) SEQUENCE DESCRIPTION: SEQ ID NO:66:

```
Val Leu Thr Gln Ser Pro Ser Ser Leu Ser Ala Ser Val Gly Asp Arg
 1               5                  10                  15

Val Thr Ile Thr Cys Arg Ala Ser Ser Ser Val Asn Tyr Met His Trp
             20                  25                  30

Tyr Gln Gln Lys Pro Gly Lys Ala Pro Lys Pro Trp Ile Tyr Ala Thr
         35                  40                  45

Ser Asn Leu Ala Ser Gly Val Pro Ser Arg Phe Ser Gly Ser Gly Ser
     50                  55                  60

Gly Thr Asp Tyr Thr Phe Thr Ile Ser Ser Leu Gln Pro Glu Asp Ile
 65                  70                  75                  80

Ala Thr Tyr Tyr Cys Gln Gln Trp Ser Ile Asn Pro Arg
                 85                  90
```

(2) INFORMATION FOR SEQ ID NO:67:

(i) SEQUENCE CHARACTERISTICS:
        (A) LENGTH: 27 base pairs

```
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(xi) SEQUENCE DESCRIPTION: SEQ ID NO:67:

TTTAGTACTC ACCCAGAGCC CAAGCAG                                         27

(2) INFORMATION FOR SEQ ID NO:68:

(i) SEQUENCE CHARACTERISTICS:
         (A) LENGTH: 27 base pairs
         (B) TYPE: nucleic acid
         (C) STRANDEDNESS: single
         (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(xi) SEQUENCE DESCRIPTION: SEQ ID NO:68:

TTCCGCGGGT TAATACTCCA CTGCTGG                                         27

(2) INFORMATION FOR SEQ ID NO:69:

(i) SEQUENCE CHARACTERISTICS:
         (A) LENGTH: 33 base pairs
         (B) TYPE: nucleic acid
         (C) STRANDEDNESS: single
         (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(xi) SEQUENCE DESCRIPTION: SEQ ID NO:69:

CTCGAGCAGT ACTATCTGGG AGTGGACACC TGT                                  33

(2) INFORMATION FOR SEQ ID NO:70:

(i) SEQUENCE CHARACTERISTICS:
         (A) LENGTH: 17 amino acids
         (B) TYPE: amino acid
         (C) STRANDEDNESS: single
         (D) TOPOLOGY: linear (ii) MOLECULE TYPE: peptide (iii) HYPOTHETICAL: NO (iv) ANTISENSE: NO
```

(v) FRAGMENT TYPE: N-terminal (vi) ORIGINAL SOURCE:

(xi) SEQUENCE DESCRIPTION: SEQ ID NO:70:

Arg Thr Phe Gly Gln Gly Thr Lys Val Glu Ile Lys Arg Thr Val Ala
 1               5                  10                  15

Ala (2) INFORMATION FOR SEQ ID NO:71:

(i) SEQUENCE CHARACTERISTICS:
            (A) LENGTH: 48 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(xi) SEQUENCE DESCRIPTION: SEQ ID NO:71:

GGACGTTCGG CCAAGGGACC AAGGTGGAAA TCAAACGGAC TGTGGCGG                48

(2) INFORMATION FOR SEQ ID NO:72:

(i) SEQUENCE CHARACTERISTICS:
            (A) LENGTH: 52 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(xi) SEQUENCE DESCRIPTION: SEQ ID NO:72:

CGCCGCCACA GTCCGTTTGA TTTCCACCTT GGTCCCTTGG CCGAACGTCC GC          52

(2) INFORMATION FOR SEQ ID NO:73:

(i) SEQUENCE CHARACTERISTICS:
            (A) LENGTH: 321 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(ix) FEATURE:

(A) NAME/KEY: Coding S equence (B) LOCATION: 1...321
(D) OTHER INFORMATION: F9HZLC 2-0

(xi) SEQUENCE DESCRIPTION: SEQ ID NO:73:

| | | | | | | | | | | | | | | | | |
|---|---|---|---|---|---|---|---|---|---|---|---|---|---|---|---|---|
| CAG | ATA | GTA | CTC | ACC | CAG | AGC | CCA | AGC | AGC | CTG | AGC | GCC | AGC | GTG | GGT | 48 |
| Gln | Ile | Val | Leu | Thr | Gln | Ser | Pro | Ser | Ser | Leu | Ser | Ala | Ser | Val | Gly | |
| 1 | | | | 5 | | | | | 10 | | | | | 15 | | |
| GAC | AGA | GTG | ACC | ATC | ACC | TGC | AGG | GCC | AGC | TCA | AGT | GTA | AAT | TAC | ATG | 96 |
| Asp | Arg | Val | Thr | Ile | Thr | Cys | Arg | Ala | Ser | Ser | Ser | Val | Asn | Tyr | Met | |
| | | | 20 | | | | | 25 | | | | | 30 | | | |
| CAC | TGG | TAC | CAG | CAG | AAG | CCA | GGT | AAG | GCT | CCA | AAG | CCT | TGG | ATC | TAC | 144 |
| His | Trp | Tyr | Gln | Gln | Lys | Pro | Gly | Lys | Ala | Pro | Lys | Pro | Trp | Ile | Tyr | |
| | | 35 | | | | | 40 | | | | | 45 | | | | |
| GCC | ACT | AGT | AAC | CTG | GCT | TCT | GGT | GTG | CCA | AGC | AGA | TTC | AGC | GGA | TCC | 192 |
| Ala | Thr | Ser | Asn | Leu | Ala | Ser | Gly | Val | Pro | Ser | Arg | Phe | Ser | Gly | Ser | |
| 50 | | | | | 55 | | | | | 60 | | | | | | |
| GGT | AGC | GGT | ACA | GAC | TAC | ACC | TTC | ACC | ATC | AGC | AGC | CTC | CAG | CCA | GAG | 240 |
| Gly | Ser | Gly | Thr | Asp | Tyr | Thr | Phe | Thr | Ile | Ser | Ser | Leu | Gln | Pro | Glu | |
| 65 | | | | 70 | | | | | 75 | | | | | 80 | | |
| GAT | ATC | GCC | ACC | TAC | TAC | TGC | CAG | CAG | TGG | AGT | ATT | AAC | CCG | CGG | ACG | 288 |
| Asp | Ile | Ala | Thr | Tyr | Tyr | Cys | Gln | Gln | Trp | Ser | Ile | Asn | Pro | Arg | Thr | |
| | | | 85 | | | | | 90 | | | | | 95 | | | |
| TTC | GGC | CAA | GGG | ACC | AAG | GTG | GAA | ATC | AAA | CGG | | | | | | 321 |
| Phe | Gly | Gln | Gly | Thr | Lys | Val | Glu | Ile | Lys | Arg | | | | | | |
| | | 100 | | | | | 105 | | | | | | | | | |

(2) INFORMATION FOR SEQ ID NO:74:

(i) SEQUENCE CHARACTERISTICS:
        (A) LENGTH: 107 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTISENSE: NO (v) FRAGMENT TYPE: internal (vi) ORIGINAL SOURCE:

(xi) SEQUENCE DESCRIPTION: SEQ ID NO:74:

| | | | | | | | | | | | | |
|---|---|---|---|---|---|---|---|---|---|---|---|---|
| Gln | Ile | Val | Leu | Thr | Gln | Ser | Pro | Ser | Ser | Leu | Ser | Ala | Ser | Val | Gly |
| 1 | | | | 5 | | | | | 10 | | | | | 15 | |

| Asp | Arg | Val | Thr | Ile | Thr | Cys | Arg | Ala | Ser | Ser | Ser | Val | Asn | Tyr | Met |
| | | | 20 | | | | | 25 | | | | | 30 | | |

| His | Trp | Tyr | Gln | Gln | Lys | Pro | Gly | Lys | Ala | Pro | Lys | Pro | Trp | Ile | Tyr |
| | | 35 | | | | | 40 | | | | | 45 | | | |

| Ala | Thr | Ser | Asn | Leu | Ala | Ser | Gly | Val | Pro | Ser | Arg | Phe | Ser | Gly | Ser |
| 50 | | | | | 55 | | | | | 60 | | | | | |

| Gly | Ser | Gly | Thr | Asp | Tyr | Thr | Phe | Thr | Ile | Ser | Ser | Leu | Gln | Pro | Glu |
| 65 | | | | 70 | | | | | 75 | | | | | 80 | |

| Asp | Ile | Ala | Thr | Tyr | Tyr | Cys | Gln | Gln | Trp | Ser | Ile | Asn | Pro | Arg | Thr |
| | | | 85 | | | | | 90 | | | | | 95 | | |

| Phe | Gly | Gln | Gly | Thr | Lys | Val | Glu | Ile | Lys | Arg |
| | | 100 | | | | | 105 | | | |

(2) INFORMATION FOR SEQ ID NO:75:

(i) SEQUENCE CHARACTERISTICS:

(A) LENGTH: 94 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(ix) FEATURE:

(A) NAME/KEY: Coding S equence
        (B) LOCATION: 27...94
        (D) OTHER INFORMATION:

(xi) SEQUENCE DESCRIPTION: SEQ ID NO:75:

```
GAATTCTGAG CACACAGGAC CTCACC ATG GGA TGG AGC T GT ATC ATC CTC TTC      53
                            Met Gly Trp Se r Cys Ile Ile Leu Phe
                             1               5

TTG GTA GCA ACA GCT ACA GGT GTC CAC TCC CAG ATA GTA CT                 94
Leu Val Ala Thr Ala Thr Gly Val His Ser Gln Ile Val Leu
 10          15                  20
```

(2) INFORMATION FOR SEQ ID NO:76:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTISENSE: NO (v) FRAGMENT TYPE: internal (vi) ORIGINAL SOURCE:

(xi) SEQUENCE DESCRIPTION: SEQ ID NO:76:

```
Met Gly Trp Ser Cys Ile Ile Leu Phe Leu Val Ala Thr Ala Thr Gly
 1               5                  10                  15

Val His Ser Gln Ile Val Leu
                20
```

(2) INFORMATION FOR SEQ ID NO:77:

(i) SEQUENCE CHARACTERISTICS:
        (A) LENGTH: 401 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(ix) FEATURE:

(A) NAME/KEY: Coding Sequence
(B) LOCATION: 27...401
(D) OTHER INFORMATION: F9HZLC 1-3

(xi) SEQUENCE DESCRIPTION: SEQ ID NO:77:

```
GAATTCTGAG CACACAGGAC CTCACC ATG GGA TGG AGC T GT ATC ATC CTC TTC          53
                             Met Gly Trp Ser Cys Ile Ile Leu Phe
                              1               5

TTG GTA GCA ACA GCT ACA GGT GTC CAC TCC CAG ATA GTA CTG ACA CAG            101
Leu Val Ala Thr Ala Thr Gly Val His Ser Gln Ile Val Leu Thr Gln
 10              15                  20                  25

TCT CCA GCC ACC CTG TCT TTG TCT CCA GGG GAA AGA GCC ACC CTC TCC            149
Ser Pro Ala Thr Leu Ser Leu Ser Pro Gly Glu Arg Ala Thr Leu Ser
                 30                  35                  40

TGC AGG GCC AGC TCA AGT GTA AAT TAC ATG CAC TGG TAC CAA CAG AGA            197
Cys Arg Ala Ser Ser Ser Val Asn Tyr Met His Trp Tyr Gln Gln Arg
             45                  50                  55

CCT GGC CAG GCT CCC AAG CCC TGG ATC TAT GCC ACG AGT AAC CTG GCT            245
Pro Gly Gln Ala Pro Lys Pro Trp Ile Tyr Ala Thr Ser Asn Leu Ala
         60                  65                  70

AGC GGC GTC CCA GCC AGG TTC AGT GGA TCC GGG TCT GGG ACA GAT TAC            293
Ser Gly Val Pro Ala Arg Phe Ser Gly Ser Gly Ser Gly Thr Asp Tyr
 75                  80                  85

ACT CTC ACG ATA TCC AGT CTA GAG CCT GAA GAT TTT GCG GTT TAT TAC            341
Thr Leu Thr Ile Ser Ser Leu Glu Pro Glu Asp Phe Ala Val Tyr Tyr
 90                  95                 100                 105

TGT CAG CAG TGG AGT ATT AAC CCG CGG ACG TTC GGC GGA GGG ACC AAG            389
Cys Gln Gln Trp Ser Ile Asn Pro Arg Thr Phe Gly Gly Gly Thr Lys
                110                 115                 120

GTG GAG ATC AAA                                                             401
Val Glu Ile Lys
        125
```

(2) INFORMATION FOR SEQ ID NO:78:

(i) SEQUENCE CHARACTERISTICS:
        (A) LENGTH: 125 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTISENSE: NO (v) FRAGMENT TYPE: internal (vi) ORIGINAL SOURCE:

(xi) SEQUENCE DESCRIPTION: SEQ ID NO:78:

```
Met Gly Trp Ser Cys Ile Ile Leu Phe Leu Val Ala Thr Ala Thr Gly
 1               5                  10                  15

Val His Ser Gln Ile Val Leu Thr Gln Ser Pro Ala Thr Leu Ser Leu
             20                  25                  30

Ser Pro Gly Glu Arg Ala Thr Leu Ser Cys Arg Ala Ser Ser Ser Val
         35                  40                  45

Asn Tyr Met His Trp Tyr Gln Gln Arg Pro Gly Gln Ala Pro Lys Pro
 50                  55                  60

Trp Ile Tyr Ala Thr Ser Asn Leu Ala Ser Gly Val Pro Ala Arg Phe
 65                  70                  75                  80

Ser Gly Ser Gly Ser Gly Thr Asp Tyr Thr Leu Thr Ile Ser Ser Leu
```

```
                85                  90                  95
Glu Pro Glu Asp Phe Ala Val Tyr Tyr Cys Gln Gln Trp Ser Ile Asn
            100                 105                 110
Pro Arg Thr Phe Gly Gly Gly Thr Lys Val Glu Ile Lys
        115                 120                 125
```

(2) INFORMATION FOR SEQ ID NO:79:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(xi) SEQUENCE DESCRIPTION: SEQ ID NO:79:

```
AGGCCTCTGG ATACACCTTC ACTAACTATG GAATGAACTG GGTGCGACAG GCCCCTGGAC      60
AAGGGCTCGA GTGGATGGGA T                                                81
```

(2) INFORMATION FOR SEQ ID NO:80:

(i) SEQUENCE CHARACTERISTICS:
        (A) LENGTH: 99 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(xi) SEQUENCE DESCRIPTION: SEQ ID NO:80:

```
TGTCTAGAGA GAAGACAAAC CGTCCCTTGA AGTCATCAAC ATATGTTGAC TTTCCATTTC      60
TGGTGTTTAT CCATCCCATC CACTCGAGCC CTTGTCCAG                             99
```

(2) INFORMATION FOR SEQ ID NO:81:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(xi) SEQUENCE DESCRIPTION: SEQ ID NO:81:

```
GGTTTGTCTT CTCTCTAGAC ACCTCTGTCA GCACGGCATA TCTACAGATC AGCAGCCTAA    60

AGGCTGAGGA CACTGCAGTG TATTTCT                                       87
```

(2) INFORMATION FOR SEQ ID NO:82:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(xi) SEQUENCE DESCRIPTION: SEQ ID NO:82:

```
GGTACCCTGG CCCCAGTAAG TAAAAGGGAA GTAACCATCC ATATTCCCTT CTCTCGTACA    60

GAAATACACT GCAGTGTCCT CAGCCT                                        86
```

(2) INFORMATION FOR SEQ ID NO:83:

(i) SEQUENCE CHARACTERISTICS:
        (A) LENGTH: 278 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(ix) FEATURE:

(A) NAME/KEY: Coding S equence
        (B) LOCATION: 3...278
        (D) OTHER INFORMATION:

(xi) SEQUENCE DESCRIPTION: SEQ ID NO:83:

```
AG GCC TCT GGA TAC ACC TTC ACT AAC TAT GGA ATG AAC TGG GTG CGA      47
   Ala Ser Gly Tyr Thr Phe Thr Asn Tyr Gly Met Asn Trp Val Arg
   1               5                  10                  15

CAG GCC CCT GGA CAA GGG CTC GAG TGG ATG GGA TGG ATA AAC ACC AGA     95
Gln Ala Pro Gly Gln Gly Leu Glu Trp Met Gly Trp Ile Asn Thr Arg
            20                  25                  30

AAT GGA AAG TCA ACA TAT GTT GAT GAC TTC AAG GGA CGG TTT GTC TTC    143
Asn Gly Lys Ser Thr Tyr Val Asp Asp Phe Lys Gly Arg Phe Val Phe
                35                  40                  45

TCT CTA GAC ACC TCT GTC AGC ACG GCA TAT CTA CAG ATC AGC AGC CTA    191
Ser Leu Asp Thr Ser Val Ser Thr Ala Tyr Leu Gln Ile Ser Ser Leu
            50                  55                  60

AAG GCT GAG GAC ACT GCA GTG TAT TTC TGT ACG AGA GAA GGG AAT ATG    239
Lys Ala Glu Asp Thr Ala Val Tyr Phe Cys Thr Arg Glu Gly Asn Met
65                  70                  75

GAT GGT TAC TTC CCT TTT ACT TAC TGG GGC CAG GGT ACC                278
Asp Gly Tyr Phe Pro Phe Thr Tyr Trp Gly Gln Gly Thr
80                  85                  90
```

(2) INFORMATION FOR SEQ ID NO:84:

(i) SEQUENCE CHARACTERISTICS:
        (A) LENGTH: 92 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTISENSE: NO (v) FRAGMENT TYPE: internal (vi) ORIGINAL SOURCE:

(xi) SEQUENCE DESCRIPTION: SEQ ID NO:84:

```
Ala Ser Gly Tyr Thr Phe Thr Asn Tyr Gly Met Asn Trp Val Arg Gln
 1               5                  10                  15

Ala Pro Gly Gln Gly Leu Glu Trp Met Gly Trp Ile Asn Thr Arg Asn
                20                  25                  30

Gly Lys Ser Thr Tyr Val Asp Asp Phe Lys Gly Arg Phe Val Phe Ser
                35                  40                  45

Leu Asp Thr Ser Val Ser Thr Ala Tyr Leu Gln Ile Ser Ser Leu Lys
    50                  55                  60

Ala Glu Asp Thr Ala Val Tyr Phe Cys Thr Arg Glu Gly Asn Met Asp
65                  70                  75                  80

Gly Tyr Phe Pro Phe Thr Tyr Trp Gly Gln Gly Thr
                85                  90
```

(2) INFORMATION FOR SEQ ID NO:85:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(xi) SEQUENCE DESCRIPTION: SEQ ID NO:85:

AGGCCTCTGG ATACACCTTC ACTAACTATG                        30

(2) INFORMATION FOR SEQ ID NO:86:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(xi) SEQUENCE DESCRIPTION: SEQ ID NO:86:

GGTACCCTGG CCCCAGTAAG TAAAAG                                                26

(2) INFORMATION FOR SEQ ID NO:87:

(i) SEQUENCE CHARACTERISTICS:
              (A) LENGTH: 37 base pairs
              (B) TYPE: nucleic acid
              (C) STRANDEDNESS: single
              (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(xi) SEQUENCE DESCRIPTION: SEQ ID NO:87:

CCAGACTCGA CTAGTTGGAT CTGGGAGTGG ACACCTG                                    37

(2) INFORMATION FOR SEQ ID NO:88:

(i) SEQUENCE CHARACTERISTICS:
              (A) LENGTH: 446 base pairs
              (B) TYPE: nucleic acid
              (C) STRANDEDNESS: single
              (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(ix) FEATURE:

(A) NAME/KEY: Coding S equence
              (B) LOCATION: 27...446
              (D) OTHER INFORMATION: F9HZHC 3-0

(xi) SEQUENCE DESCRIPTION: SEQ ID NO:88:

GAATTCTGAG CACACAGGAC CTCACC ATG GGA TGG AGC T GT ATC ATC CTC TTC           53
                            Met Gly Trp Se r Cys Ile Ile Leu Phe
                             1               5

TTG GTA GCA ACA GCT ACA GGT GTC CAC TCC CAG ATC CAA CTA GTG CAA            101
Leu Val Ala Thr Ala Thr Gly Val His Ser Gln Ile Gln Leu Val Gln
 10              15                  20                  25

TCT GGG TCT GAG TTG AAG AAG CCT GGG GCC TCA GTG AAG GTT TCC TGC            149
Ser Gly Ser Glu Leu Lys Lys Pro Gly Ala Ser Val Lys Val Ser Cys
                 30                  35                  40

AAG GCC TCT GGA TAC ACC TTC ACT AAC TAT GGA ATG AAC TGG GTG CGA            197
Lys Ala Ser Gly Tyr Thr Phe Thr Asn Tyr Gly Met Asn Trp Val Arg
                     45                  50                  55

CAG GCC CCT GGA CAA GGG CTC GAG TGG ATG GGA TGG ATA AAC ACC AGA            245
Gln Ala Pro Gly Gln Gly Leu Glu Trp Met Gly Trp Ile Asn Thr Arg
         60                  65                  70

AAT GGA AAG TCA ACA TAT GTT GAT GAC TTC AAG GGA CGG TTT GTC TTC            293
Asn Gly Lys Ser Thr Tyr Val Asp Asp Phe Lys Gly Arg Phe Val Phe

```
                75                    80                    85
TCT CTA GAC ACC TCT GTC AGC ACG GCA TAT CTA CAG ATC AGC AGC CTA      341
Ser Leu Asp Thr Ser Val Ser Thr Ala Tyr Leu Gln Ile Ser Ser Leu
 90                  95                 100                 105

AAG GCT GAG GAC ACT GCA GTG TAT TTC TGT ACG AGA GAA GGG AAT ATG      389
Lys Ala Glu Asp Thr Ala Val Tyr Phe Cys Thr Arg Glu Gly Asn Met
                    110                 115                 120

GAT GGT TAC TTC CCT TTT ACT TAC TGG GGC CAG GGT ACC CTG GTC ACC      437
Asp Gly Tyr Phe Pro Phe Thr Tyr Trp Gly Gln Gly Thr Leu Val Thr
                125                 130                 135

GTC TCC TCT                                                          446
Val Ser Ser
        140
```

(2) INFORMATION FOR SEQ ID NO:89:

(i) SEQUENCE CHARACTERISTICS:
        (A) LENGTH: 140 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTISENSE: NO (v) FRAGMENT TYPE: internal (vi) ORIGINAL SOURCE:

(xi) SEQUENCE DESCRIPTION: SEQ ID NO:89:

```
Met Gly Trp Ser Cys Ile Ile Leu Phe Leu Val Ala Thr Ala Thr Gly
 1               5                  10                  15

Val His Ser Gln Ile Gln Leu Val Gln Ser Gly Ser Glu Leu Lys Lys
                20                  25                  30

Pro Gly Ala Ser Val Lys Val Ser Cys Lys Ala Ser Gly Tyr Thr Phe
            35                  40                  45

Thr Asn Tyr Gly Met Asn Trp Val Arg Gln Ala Pro Gly Gln Gly Leu
        50                  55                  60

Glu Trp Met Gly Trp Ile Asn Thr Arg Asn Gly Lys Ser Thr Tyr Val
65                  70                  75                  80

Asp Asp Phe Lys Gly Arg Phe Val Phe Ser Leu Asp Thr Ser Val Ser
                85                  90                  95

Thr Ala Tyr Leu Gln Ile Ser Ser Leu Lys Ala Glu Asp Thr Ala Val
                100                 105                 110

Tyr Phe Cys Thr Arg Glu Gly Asn Met Asp Gly Tyr Phe Pro Phe Thr
            115                 120                 125

Tyr Trp Gly Gln Gly Thr Leu Val Thr Val Ser Ser
        130                 135                 140
```

(2) INFORMATION FOR SEQ ID NO:90:

(i) SEQUENCE CHARACTERISTICS:
        (A) LENGTH: 90 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(xi) SEQUENCE DESCRIPTION: SEQ ID NO:90:

AGTACTGACA CAGTCTCCAT CCTCCCTGTC TGCATCTGTT GGGGACAGAG TCACCATCAC      60

TTGCAGGGCC AGCTCAAGTG TAAATTACAT                                      90

(2) INFORMATION FOR SEQ ID NO:91:

(i) SEQUENCE CHARACTERISTICS:
        (A) LENGTH: 108 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(xi) SEQUENCE DESCRIPTION: SEQ ID NO:91:

CTTGATGGGA CGCCGCTAGC CAGGTTACTC GTGGCATAGA TCCAGGGCTT GGGAGCTTTG      60

CCAGGTTTCT GTTGGTACCA GTGCATGTAA TTTACACTTG AGCTGGCC                 108

(2) INFORMATION FOR SEQ ID NO:92:

(i) SEQUENCE CHARACTERISTICS:
        (A) LENGTH: 108 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(xi) SEQUENCE DESCRIPTION: SEQ ID NO:92:

TAACCTGGCT AGCGGCGTCC CATCAAGGTT CAGTGGATCC GGGTCTGGGA CAGATTACAC      60

TCTCACGATA TCCAGTCTAC AACCTGAAGA TTTTGCGACT TATTACTG                 108

(2) INFORMATION FOR SEQ ID NO:93:

(i) SEQUENCE CHARACTERISTICS:
        (A) LENGTH: 102 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(xi) SEQUENCE DESCRIPTION: SEQ ID NO:93:

GGCGCCGCCA CAGTTCGTTT GATCTCCAGC TTGGTCCCTC CGCCGAACGT CCGCGGGTTA    60

ATACTCCACT GCTGACAGTA ATAAGTCGCA AAATCTTCAG GT                       102

(2) INFORMATION FOR SEQ ID NO:94:

(i) SEQUENCE CHARACTERISTICS:
        (A) LENGTH: 330 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(ix) FEATURE:

(A) NAME/KEY: Coding S equence
        (B) LOCATION: 2...328
        (D) OTHER INFORMATION:

(xi) SEQUENCE DESCRIPTION: SEQ ID NO:94:

```
A GTA CTG ACA CAG TCT CCA TCC TCC CTG TCT GCA TCT GTT GGG GAC AGA      49
  Val Leu Thr Gln Ser Pro Ser Ser Leu Ser Ala Ser Val Gly Asp Arg
  1               5                  10                  15

GTC ACC ATC ACT TGC AGG GCC AGC TCA AGT GTA AAT TAC ATG CAC TGG         97
Val Thr Ile Thr Cys Arg Ala Ser Ser Ser Val Asn Tyr Met His Trp
             20                  25                  30

TAC CAA CAG AAA CCT GGC AAA GCT CCC AAG CCC TGG ATC TAT GCC ACG        145
Tyr Gln Gln Lys Pro Gly Lys Ala Pro Lys Pro Trp Ile Tyr Ala Thr
         35                  40                  45

AGT AAC CTG GCT AGC GGC GTC CCA TCA AGG TTC AGT GGA TCC GGG TCT        193
Ser Asn Leu Ala Ser Gly Val Pro Ser Arg Phe Ser Gly Ser Gly Ser
     50                  55                  60

GGG ACA GAT TAC ACT CTC ACG ATA TCC AGT CTA CAA CCT GAA GAT TTT        241
Gly Thr Asp Tyr Thr Leu Thr Ile Ser Ser Leu Gln Pro Glu Asp Phe
65                  70                  75                  80

GCG ACT TAT TAC TGT CAG CAG TGG AGT ATT AAC CCG CGG ACG TTC GGC        289
Ala Thr Tyr Tyr Cys Gln Gln Trp Ser Ile Asn Pro Arg Thr Phe Gly
                 85                  90                  95

GGA GGG ACC AAG CTG GAG ATC AAA CGA ACT GTG GCG GCG CC                 330
Gly Gly Thr Lys Leu Glu Ile Lys Arg Thr Val Ala Ala
             100                 105
```

(2) INFORMATION FOR SEQ ID NO:95:

(i) SEQUENCE CHARACTERISTICS:
        (A) LENGTH: 109 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTISENSE: NO (v) FRAGMENT TYPE: internal (vi) ORIGINAL SOURCE:

(xi) SEQUENCE DESCRIPTION: SEQ ID NO:95:

Val Leu Thr Gln Ser Pro Ser Ser Leu Ser Ala Ser Val Gly Asp Arg
1               5                   10                  15

Val Thr Ile Thr Cys Arg Ala Ser Ser Ser Val Asn Tyr Met His Trp
            20                  25                  30

Tyr Gln Gln Lys Pro Gly Lys Ala Pro Lys Pro Trp Ile Tyr Ala Thr
        35                  40                  45

Ser Asn Leu Ala Ser Gly Val Pro Ser Arg Phe Ser Gly Ser Gly Ser
    50                  55                  60

Gly Thr Asp Tyr Thr Leu Thr Ile Ser Ser Leu Gln Pro Glu Asp Phe
65              70                  75                  80

Ala Thr Tyr Tyr Cys Gln Gln Trp Ser Ile Asn Pro Arg Thr Phe Gly
            85                  90                  95

Gly Gly Thr Lys Leu Glu Ile Lys Arg Thr Val Ala Ala
            100                 105

(2) INFORMATION FOR SEQ ID NO:96:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(xi) SEQUENCE DESCRIPTION: SEQ ID NO:96:

CAAGTACTGA CACAGTCTCC ATCCTC                                                    26

(2) INFORMATION FOR SEQ ID NO:97:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(xi) SEQUENCE DESCRIPTION: SEQ ID NO:97:

AGGGCGCCGC CACAGTTCGT TTGATC                                                    26

(2) INFORMATION FOR SEQ ID NO:98:

(i) SEQUENCE CHARACTERISTICS:
        (A) LENGTH: 412 base pairs
        (B) TYPE: nucleic acid
        (C) STRANDEDNESS: single -continued (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(ix) FEATURE:

(A) NAME/KEY: Coding S equence
        (B) LOCATION: 27...412
        (D) OTHER INFORMATION: F9HZLC 3-0

(xi) SEQUENCE DESCRIPTION: SEQ ID NO:98:

```
GAATTCTGAG CACACAGGAC CTCACC ATG GGA TGG AGC T GT ATC ATC CTC TTC        53
                             Met Gly Trp Se r Cys Ile Ile Leu Phe
                              1               5

TTG GTA GCA ACA GCT ACA GGT GTC CAC TCC CAG ATA GTA CTG ACA CAG         101
Leu Val Ala Thr Ala Thr Gly Val His Ser Gln Ile Val Leu Thr Gln
 10              15              20                  25

TCT CCA TCC TCC CTG TCT GCA TCT GTT GGG GAC AGA GTC ACC ATC ACT         149
Ser Pro Ser Ser Leu Ser Ala Ser Val Gly Asp Arg Val Thr Ile Thr
                 30                  35                  40

TGC AGG GCC AGC TCA AGT GTA AAT TAC ATG CAC TGG TAC CAA CAG AAA         197
Cys Arg Ala Ser Ser Ser Val Asn Tyr Met His Trp Tyr Gln Gln Lys
             45                  50                  55

CCT GGC AAA GCT CCC AAG CCC TGG ATC TAT GCC ACG AGT AAC CTG GCT         245
Pro Gly Lys Ala Pro Lys Pro Trp Ile Tyr Ala Thr Ser Asn Leu Ala
         60                  65                  70

AGC GGC GTC CCA TCA AGG TTC AGT GGA TCC GGG TCT GGG ACA GAT TAC         293
Ser Gly Val Pro Ser Arg Phe Ser Gly Ser Gly Ser Gly Thr Asp Tyr
 75                  80                  85

ACT CTC ACG ATA TCC AGT CTA CAA CCT GAA GAT TTT GCG ACT TAT TAC         341
Thr Leu Thr Ile Ser Ser Leu Gln Pro Glu Asp Phe Ala Thr Tyr Tyr
 90                  95                 100                 105

TGT CAG CAG TGG AGT ATT AAC CCG CGG ACG TTC GGC GGA GGG ACC AAG         389
Cys Gln Gln Trp Ser Ile Asn Pro Arg Thr Phe Gly Gly Gly Thr Lys
                110                 115                 120

CTG GAG ATC AAA CGA ACT GTG GC                                          412
Leu Glu Ile Lys Arg Thr Val Val
             125
```

(2) INFORMATION FOR SEQ ID NO:99:

(i) SEQUENCE CHARACTERISTICS:
        (A) LENGTH: 129 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTISENSE: NO (v) FRAGMENT TYPE: internal (vi) ORIGINAL SOURCE:

(xi) SEQUENCE DESCRIPTION: SEQ ID NO:99:

```
Met Gly Trp Ser Cys Ile Ile Leu Phe Leu Val Ala Thr Ala Thr Gly
 1               5                  10                  15
```

```
Val His Ser Gln Ile Val Leu Thr Gln Ser Pro Ser Ser Leu Ser Ala
             20                  25                  30

Ser Val Gly Asp Arg Val Thr Ile Thr Cys Arg Ala Ser Ser Ser Val
         35                  40                  45

Asn Tyr Met His Trp Tyr Gln Gln Lys Pro Gly Lys Ala Pro Lys Pro
     50                  55                  60

Trp Ile Tyr Ala Thr Ser Asn Leu Ala Ser Gly Val Pro Ser Arg Phe
 65                  70                  75                  80

Ser Gly Ser Gly Ser Gly Thr Asp Tyr Thr Leu Thr Ile Ser Ser Leu
                 85                  90                  95

Gln Pro Glu Asp Phe Ala Thr Tyr Tyr Cys Gln Gln Trp Ser Ile Asn
            100                 105                 110

Pro Arg Thr Phe Gly Gly Gly Thr Lys Leu Glu Ile Lys Arg Thr Val
            115                 120                 125

Val
```

(2) INFORMATION FOR SEQ ID NO:100:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(xi) SEQUENCE DESCRIPTION: SEQ ID NO:100 :

CAAATAGTAC TCTCCCAGTC TCCAGC                                    26

(2) INFORMATION FOR SEQ ID NO:101:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(xi) SEQUENCE DESCRIPTION: SEQ ID NO:101 :

GGATAAGCTT GGCGCCGCAA CAGTCGGTTT GATTTCCAGC T                 41

(2) INFORMATION FOR SEQ ID NO:102:

(i) SEQUENCE CHARACTERISTICS:
        (A) LENGTH: 335 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(ix) FEATURE:
 (A) NAME/KEY: Coding S equence
 (B) LOCATION: 1...335
 (D) OTHER INFORMATION:

(xi) SEQUENCE DESCRIPTION: SEQ ID NO:102 :

```
CAG ATA GTA CTC TCC CAG TCT CCA GCA ATC CTG TCT GCA TCT CCA GGG    48
Gln Ile Val Leu Ser Gln Ser Pro Ala Ile Leu Ser Ala Ser Pro Gly
 1               5                  10                  15

GAG AAG GTC ACA ATG ACT TGC AGG GCC AGC TCA AGT GTA AAT TAC ATG    96
Glu Lys Val Thr Met Thr Cys Arg Ala Ser Ser Ser Val Asn Tyr Met
             20                  25                  30

CAC TGG TAC CAG CAG AAG CCA GGA TCC TCC CCC AAA CCC TGG ATT TAT   144
His Trp Tyr Gln Gln Lys Pro Gly Ser Ser Pro Lys Pro Trp Ile Tyr
         35                  40                  45

GCC ACA TCC AAC CTG GCT TCT GGA GTC CCT GCT CGC TTC AGT GGC AGT   192
Ala Thr Ser Asn Leu Ala Ser Gly Val Pro Ala Arg Phe Ser Gly Ser
     50                  55                  60

GGG TCT GGG ACC TCT TAC TCT CTC ACA ATC AGC AGA GTG GAG GCT GAA   240
Gly Ser Gly Thr Ser Tyr Ser Leu Thr Ile Ser Arg Val Glu Ala Glu
65                  70                  75                  80

GAT GCT GCC ACT TAT TAC TGC CAG CAG TGG AGT ATT AAC CCA CGG ACG   288
Asp Ala Ala Thr Tyr Tyr Cys Gln Gln Trp Ser Ile Asn Pro Arg Thr
                 85                  90                  95

TTC GGT GGA GGC ACC AAG CTG GAA ATC AAA CGG ACT GTT GCG GCG CC    335
Phe Gly Gly Gly Thr Lys Leu Glu Ile Lys Arg Thr Val Ala Ala Pro
                100                 105                 110
```

(2) INFORMATION FOR SEQ ID NO:103:

(i) SEQUENCE CHARACTERISTICS:
 (A) LENGTH: 112 amino acids
 (B) TYPE: amino acid
 (C) STRANDEDNESS: single
 (D) TOPOLOGY: linear (ii) MOLECULE TYPE: protein (iii) HYPOTHETICAL: NO (iv) ANTISENSE: NO (v) FRAGMENT TYPE: internal (vi) ORIGINAL SOURCE:

(xi) SEQUENCE DESCRIPTION: SEQ ID NO:103 :

```
Gln Ile Val Leu Ser Gln Ser Pro Ala Ile Leu Ser Ala Ser Pro Gly
 1               5                  10                  15

Glu Lys Val Thr Met Thr Cys Arg Ala Ser Ser Ser Val Asn Tyr Met
             20                  25                  30

His Trp Tyr Gln Gln Lys Pro Gly Ser Ser Pro Lys Pro Trp Ile Tyr
         35                  40                  45

Ala Thr Ser Asn Leu Ala Ser Gly Val Pro Ala Arg Phe Ser Gly Ser
     50                  55                  60
```

```
Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Ile Asn Pro Arg Thr
                85                  90                  95

Phe Gly Gly Gly Thr Lys Leu Glu Ile Lys Arg Thr Val Ala Ala Pro
            100                 105                 110
```

(2) INFORMATION FOR SEQ ID NO:104:

(i) SEQUENCE CHARACTERISTICS:
        (A) LENGTH: 318 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(ix) FEATURE:

(A) NAME/KEY: Coding S equence
        (B) LOCATION: 1...318
        (D) OTHER INFORMATION:

(xi) SEQUENCE DESCRIPTION: SEQ ID NO:104 :

```
CAG ATA GTA CTC TCC CAG TCT CCA GCA ATC CTG TCT GCA TCT CCA GGG     48
Gln Ile Val Leu Ser Gln Ser Pro Ala Ile Leu Ser Ala Ser Pro Gly
1               5                   10                  15

GAG AAG GTC ACA ATG ACT TGC AGG GCC AGC TCA AGT GTA AAT TAC ATG     96
Glu Lys Val Thr Met Thr Cys Arg Ala Ser Ser Ser Val Asn Tyr Met
                20                  25                  30

CAC TGG TAC CAG CAG AAG CCA GGA TCC TCC CCC AAA CCC TGG ATT TAT    144
His Trp Tyr Gln Gln Lys Pro Gly Ser Ser Pro Lys Pro Trp Ile Tyr
            35                  40                  45

GCC ACA TCC AAC CTG GCT TCT GGA GTC CCT GCT CGC TTC AGT GGC AGT    192
Ala Thr Ser Asn Leu Ala Ser Gly Val Pro Ala Arg Phe Ser Gly Ser
50                  55                  60

GGG TCT GGG ACC TCT TAC TCT CTC ACA ATC AGC AGA GTG GAG GCT GAA    240
Gly Ser Gly Thr Ser Tyr Ser Leu Thr Ile Ser Arg Val Glu Ala Glu
65                  70                  75                  80

GAT GCT GCC ACT TAT TAC TGC CAG CAG TGG AGT ATT AAC CCA CGG ACG    288
Asp Ala Ala Thr Tyr Tyr Cys Gln Gln Trp Ser Ile Asn Pro Arg Thr
                85                  90                  95

TTC GGT GGA GGC ACC AAG CTG GAA ATC AAA                            318
Phe Gly Gly Gly Thr Lys Leu Glu Ile Lys
            100                 105
```

(2) INFORMATION FOR SEQ ID NO:105:

(i) SEQUENCE CHARACTERISTICS:
        (A) LENGTH: 106 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTISENSE: NO (v) FRAGMENT TYPE: internal (vi) ORIGINAL SOURCE:

(xi) SEQUENCE DESCRIPTION: SEQ ID NO:105 :

```
Gln Ile Val Leu Ser Gln Ser Pro Ala Ile Leu Ser Ala Ser Pro Gly
 1               5                  10                  15
Glu Lys Val Thr Met Thr Cys Arg Ala Ser Ser Val Asn Tyr Met
            20                  25                  30
His Trp Tyr Gln Gln Lys Pro Gly Ser Ser Pro Lys Pro Trp Ile Tyr
        35                  40                  45
Ala Thr Ser Asn Leu Ala Ser Gly Val Pro Ala Arg Phe Ser Gly Ser
    50                  55                  60
Gly Ser Gly Thr Ser Tyr Ser Leu Thr Ile Ser Arg Val Glu Ala Glu
65                  70                  75                  80
Asp Ala Ala Thr Tyr Tyr Cys Gln Gln Trp Ser Ile Asn Pro Arg Thr
                85                  90                  95
Phe Gly Gly Gly Thr Lys Leu Glu Ile Lys
            100                 105
```

(2) INFORMATION FOR SEQ ID NO:106:

(i) SEQUENCE CHARACTERISTICS:
      (A) LENGTH: 30 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(xi) SEQUENCE DESCRIPTION: SEQ ID NO:106 :

CAGATCCAAC TAGTGCAGTC TGGACCTGAG       30

(2) INFORMATION FOR SEQ ID NO:107:

(i) SEQUENCE CHARACTERISTICS:
      (A) LENGTH: 32 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(xi) SEQUENCE DESCRIPTION: SEQ ID NO:107 :

TTAAGCTTGC TAGCTGCAGA GACAGTGACC AG       32

(2) INFORMATION FOR SEQ ID NO:108:

(i) SEQUENCE CHARACTERISTICS:
      (A) LENGTH: 369 base pairs
      (B) TYPE: nucleic acid (C) STRANDEDNESS: single
         (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(ix) FEATURE:

(A) NAME/KEY: Coding S equence
         (B) LOCATION: 1...369
         (D) OTHER INFORMATION:

(xi) SEQUENCE DESCRIPTION: SEQ ID NO:108 :

```
CAG ATC CAA CTA GTG CAG TCT GGA CCT GAG CTG AAG AAG CCT GGA GAG      48
Gln Ile Gln Leu Val Gln Ser Gly Pro Glu Leu Lys Lys Pro Gly Glu
 1               5                  10                  15

ACA GTC AAG ATC TCC TGC AAG GCT TCT GGG TAC ACC TTC ACA AAC TAT      96
Thr Val Lys Ile Ser Cys Lys Ala Ser Gly Tyr Thr Phe Thr Asn Tyr
             20                  25                  30

GGA ATG AAC TGG GTG AAG CAG GCT CCA GGA AAG GGT TTA AAG TGG ATG     144
Gly Met Asn Trp Val Lys Gln Ala Pro Gly Lys Gly Leu Lys Trp Met
         35                  40                  45

GGC TGG ATA AAC ACC AGA AAT GGA AAG TCA ACA TAT GTT GAT GAC TTC     192
Gly Trp Ile Asn Thr Arg Asn Gly Lys Ser Thr Tyr Val Asp Asp Phe
     50                  55                  60

AAG GGA CGG TTT GCC TTC TCT TTG GAA AGC TCT GCC AGC ACT GCC AAT     240
Lys Gly Arg Phe Ala Phe Ser Leu Glu Ser Ser Ala Ser Thr Ala Asn
 65                  70                  75                  80

TTG CAG ATC GAC AAC CTC AAA GAT GAG GAC ACG GCT ACA TAT TTC TGT     288
Leu Gln Ile Asp Asn Leu Lys Asp Glu Asp Thr Ala Thr Tyr Phe Cys
                 85                  90                  95

ACA AGA GAA GGG AAT ATG GAT GGT TAC TTC CCT TTT ACT TAC TGG GGC     336
Thr Arg Glu Gly Asn Met Asp Gly Tyr Phe Pro Phe Thr Tyr Trp Gly
             100                 105                 110

CAA GGG ACT CTG GTC ACT GTC TCT GCA GCT AGC                         369
Gln Gly Thr Leu Val Thr Val Ser Ala Ala Ser
         115                 120
```

(2) INFORMATION FOR SEQ ID NO:109:

(i) SEQUENCE CHARACTERISTICS:
         (A) LENGTH: 123 amino acids
         (B) TYPE: amino acid
         (C) STRANDEDNESS: single
         (D) TOPOLOGY: linear (ii) MOLECULE TYPE: protein (iii) HYPOTHETICAL: NO (iv) ANTISENSE: NO (v) FRAGMENT TYPE: internal (vi) ORIGINAL SOURCE:

(xi) SEQUENCE DESCRIPTION: SEQ ID NO:109 :

```
Gln Ile Gln Leu Val Gln Ser Gly Pro Glu Leu Lys Lys Pro Gly Glu
 1               5                  10                  15

Thr Val Lys Ile Ser Cys Lys Ala Ser Gly Tyr Thr Phe Thr Asn Tyr
             20                  25                  30
```

```
Gly Met Asn Trp Val Lys Gln Ala Pro Gly Lys Gly Leu Lys Trp Met
        35                  40                  45

Gly Trp Ile Asn Thr Arg Asn Gly Lys Ser Thr Tyr Val Asp Asp Phe
 50                  55                  60

Lys Gly Arg Phe Ala Phe Ser Leu Glu Ser Ser Ala Ser Thr Ala Asn
 65                  70                  75                  80

Leu Gln Ile Asp Asn Leu Lys Asp Glu Asp Thr Ala Thr Tyr Phe Cys
                 85                  90                  95

Thr Arg Glu Gly Asn Met Asp Gly Tyr Phe Pro Phe Thr Tyr Trp Gly
             100                 105                 110

Gln Gly Thr Leu Val Thr Val Ser Ala Ala Ser
         115                 120
```

(2) INFORMATION FOR SEQ ID NO:110:

(i) SEQUENCE CHARACTERISTICS:
        (A) LENGTH: 363 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTISENSE: NO (v) FRAGMENT TYPE:

(vi) ORIGINAL SOURCE:

(ix) FEATURE:

(A) NAME/KEY: Coding S equence
        (B) LOCATION: 1...363
        (D) OTHER INFORMATION:

(xi) SEQUENCE DESCRIPTION: SEQ ID NO:110 :

```
CAG ATC CAA CTA GTG CAG TCT GGA CCT GAG CTG AAG AAG CCT GGA GAG     48
Gln Ile Gln Leu Val Gln Ser Gly Pro Glu Leu Lys Lys Pro Gly Glu
 1               5                  10                  15

ACA GTC AAG ATC TCC TGC AAG GCT TCT GGG TAC ACC TTC ACA AAC TAT     96
Thr Val Lys Ile Ser Cys Lys Ala Ser Gly Tyr Thr Phe Thr Asn Tyr
             20                  25                  30

GGA ATG AAC TGG GTG AAG CAG GCT CCA GGA AAG GGT TTA AAG TGG ATG    144
Gly Met Asn Trp Val Lys Gln Ala Pro Gly Lys Gly Leu Lys Trp Met
         35                  40                  45

GGC TGG ATA AAC ACC AGA AAT GGA AAG TCA ACA TAT GTT GAT GAC TTC    192
Gly Trp Ile Asn Thr Arg Asn Gly Lys Ser Thr Tyr Val Asp Asp Phe
 50                  55                  60

AAG GGA CGG TTT GCC TTC TCT TTG GAA AGC TCT GCC AGC ACT GCC AAT    240
Lys Gly Arg Phe Ala Phe Ser Leu Glu Ser Ser Ala Ser Thr Ala Asn
 65                  70                  75                  80

TTG CAG ATC GAC AAC CTC AAA GAT GAG GAC ACG GCT ACA TAT TTC TGT    288
Leu Gln Ile Asp Asn Leu Lys Asp Glu Asp Thr Ala Thr Tyr Phe Cys
                 85                  90                  95

ACA AGA GAA GGG AAT ATG GAT GGT TAC TTC CCT TTT ACT TAC TGG GGC    336
Thr Arg Glu Gly Asn Met Asp Gly Tyr Phe Pro Phe Thr Tyr Trp Gly
             100                 105                 110

CAA GGG ACT CTG GTC ACT GTC TCT GCA                                363
Gln Gly Thr Leu Val Thr Val Ser Ala
         115                 120
```

-continued (2) INFORMATION FOR SEQ ID NO:111:

(i) SEQUENCE CHARACTERISTICS:
        (A) LENGTH: 121 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTISENSE: NO (v) FRAGMENT TYPE: internal (vi) ORIGINAL SOURCE:

(xi) SEQUENCE DESCRIPTION: SEQ ID NO:111 :

```
Gln Ile Gln Leu Val Gln Ser Gly Pro Glu Leu Lys Lys Pro Gly Glu
 1               5                  10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Arg Asn Gly Lys Ser Thr Tyr Val Asp Asp Phe
    50                  55                  60

Lys Gly Arg Phe Ala Phe Ser Leu Glu Ser Ser Ala Ser Thr Ala Asn
65                  70                  75                  80

Leu Gln Ile Asp Asn Leu Lys Asp Glu Asp Thr Ala Thr Tyr Phe Cys
                85                  90                  95

Thr Arg Glu Gly Asn Met Asp Gly Tyr Phe Pro Phe Thr Tyr Trp Gly
            100                 105                 110

Gln Gly Thr Leu Val Thr Val Ser Ala
            115                 120
```